(12) United States Patent
Reddy et al.

(10) Patent No.: US 8,808,702 B2
(45) Date of Patent: Aug. 19, 2014

(54) SULFIDE, SULFOXIDE AND SULFONE CHALCONE ANALOGUES, DERIVATIVES THEREOF AND THERAPEUTIC USES THEREOF

(75) Inventors: E. Premkumar Reddy, Villanova, PA (US); M. V. Ramana Reddy, Upper Darby, PA (US)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 12/448,098

(22) PCT Filed: Dec. 12, 2007

(86) PCT No.: PCT/US2007/025378
§ 371 (c)(1),
(2), (4) Date: Jun. 8, 2009

(87) PCT Pub. No.: WO2008/076270
PCT Pub. Date: Jun. 26, 2008

(65) Prior Publication Data
US 2010/0028368 A1 Feb. 4, 2010

Related U.S. Application Data

(60) Provisional application No. 60/874,652, filed on Dec. 13, 2006, provisional application No. 60/961,796, filed on Jul. 24, 2007.

(51) Int. Cl.
*A61K 31/395* (2006.01)
*A61K 31/10* (2006.01)
*C12P 21/08* (2006.01)
*C07C 317/14* (2006.01)
*C07C 317/24* (2006.01)

(52) U.S. Cl.
CPC .............. *A61K 31/395* (2013.01); *A61K 31/10* (2013.01); *C07C 317/14* (2013.01); *C07C 317/24* (2013.01)
USPC ..................... 424/178.1; 530/391.7; 514/710; 514/713; 568/30; 568/31; 568/37; 568/42; 568/43

(58) Field of Classification Search
CPC .... C07C 317/24; C07C 317/14; A61K 31/10; A61K 31/395
USPC ........... 424/178.1; 530/391.7; 568/30, 31, 37, 568/42, 43; 514/710, 713
See application file for complete search history.

(56) References Cited

U.S. PATENT DOCUMENTS

| | | | | |
|---|---|---|---|---|
| 5,952,355 A | * | 9/1999 | Ikeda et al. | 514/339 |
| 6,359,013 B1 | | 3/2002 | Reddy et al. | 514/710 |
| 6,548,553 B2 | | 4/2003 | Reddy et al. | 514/710 |
| 6,656,973 B2 | | 12/2003 | Cosenza et al. | 514/710 |
| 6,667,346 B2 | | 12/2003 | Reddy et al. | 514/710 |
| 6,767,926 B1 | | 7/2004 | Cosenza et al. | 514/710 |

FOREIGN PATENT DOCUMENTS

| WO | WO 00/59494 | 10/2000 | ............ A61K 31/10 |
|---|---|---|---|
| WO | WO 01/26645 | 4/2001 | ............ A61K 31/10 |

OTHER PUBLICATIONS

Schaefer et al. Failure is not an option: learning from unsuccessful proof-of-concept trials. Drug Discovery Today, 2008, 13(21/22), pp. 913-916.*
Horig et al. Review: From bench to clinic and back: Perspective on the 1st IQPC Translational Research Conference. Journal of Translational Medicine, 2004, 2(44).*
Burger's Medicinal Chemistry and Drug Discovery, Fifth Edition, vol. I: Principles and Practice, Wiley-Interscience, 1995, pp. 783-802.*
Thibonnet et al. (Tetrahedron Letters, 41, 2000, 3319-3322).*
Thibonnet et al. (Tetrahedron, 58, 2002, 4787-4799).*
Batterjee. Spectral studies and configurational assignments of some 2-propenone derivatives. Phosphorus, Sulfur and Silicon, 2002, 177: 33-44.*
Patani et al. (Chem Rev., 1996, 96, 3146-76).*
Krishna et al. Antimicrobial activity of sulphonylchalcones and sulphonylcyclohexenones. Current Science, Dec. 5, 1988, vol. 57, No. 23.*
Williams et al. (Foye's Principles of Medicinal Chemistry, pp. 59-61, 2002).*
Swenson et al. Synthesis of substituted quinolines using the dianion addition of N-boc-anilines and alpha-tolylsulfonyl-alpha,beta-unsaturated ketones. J. Org. Chem. 2002, 67, 9182-9185.*
Database Registry Chemical Abstracts Service, Columbus, Ohio, Accession No. RN 69248-67-5, RN 69248-66-4, RN 69248-65-3, Entered STN: Nov. 16, 1984, Accession No. RN 344878-28-0, RN 344878-30-4, Entered STN: Jul. 8, 2001, Accession No. RN 344941-61-3, RN 344941-31-7, RN 344941-62-4, Entered STN: Jul. 9, 2001.*

(Continued)

*Primary Examiner* — Samantha Shterengarts
(74) *Attorney, Agent, or Firm* — Drinker Biddle & Reath LLP

(57) ABSTRACT

Compounds useful as antiproliferative agents according to formula (I): wherein $Ar^1$, $Ar^2$, $Ar^3$, m and n are as defined herein, salts, antibody conjugates, pharmaceutical compositions, methods of treatment, and synthetic methods are provided.

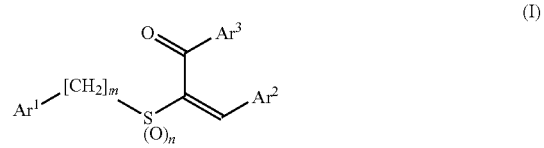

(I)

40 Claims, No Drawings

(56) References Cited

OTHER PUBLICATIONS

Ito et al. [Ito, Nobuyuki. Cancer Science 94(1), (2003) 3-8.*
N.D. Shinde, et al., "Synthesis of Some New Heterocyclic Compounds and Their Antimicrobial Activity", *Oriental J. of Chemistry*, 1995, 11, (No. 2), 169-172.
S.V. Krishna, et al., "Antimicrobial Activity of Sulphonylchalcones and Sulphonylcyclohexenones", *Current Science*, 1988, 57, (No. 23), 1291-1293.
Chemical Abstracts, 111:153696, abstracting Shingare, et al., "Synthesis and Biological Activity of Some New Substituted Pyrazolines and Isoxazolines", *Indian J. of Chemistry*, Section B, 1989, 28B(2), 154-158.
Chemical Abstracts, 95:186784, abstracting Tishchenko, et al., "Condensation of Benzyl Phenacyl Sulfide With Nitrobenzaldehydes", *Vestsi Akademii Navuk BSSR, Seryya Khimichnykh Navuk*, 1981, (4), 64-68.
Chemical Abstracts, 90:86939, abstracting Malashko, et al., "Condensation of p-Methylphenacylbenzylthio Ether With Aromatic Aldehydes", *Vestsi Akademii Navuk BSSR, Seryya Khimichnykh Navuk*, 1978, (6), 97-102.
Chemical Abstracts, 133:192955, abstracting Betts, et al., "Novel Knoevenagel Condensations of a Beta-Keto Sulfone and a Beta-Carboalkoxy Sulfone", *Sulfur Lett.*, 1999, 23(1), 11-31.
Chemical Abstracts, 109:54422, abstracting Reddy, et al., "Facile Method for the Synthesis of 2-(Arylsulfonyl)-1-phenyl-3-aryl-2-propen-1-ones", *Sulfur Lett.*, 1987, 7(2), 43-48.
Chemical Abstracts, 102:59129, abstracting Simon, et al., "Phenoxy and Phenylthiochalcones: Effect of Substitution on Antifungal and Antiprotozoal Activities", *Fr. Annales Pharm. Francaises*, 1984, 42(3), 271-282.
Chemical Abstracts, 83:43125, abstracting Ukai, et al., "Synthesis and Biological Activity of Sulfur Containing Derivatives of Chalcone. IV. Novel Method for the Synthesis of Thioaurones", *Yakugaku Zasshi*, 1975, 95(3), 299-303.
Chemical Abstracts, 82:31079, abstracting Ukai, et al., "Synthesis and Biological Activity of Sulfur Containing Derivatives of Chalcone. III. Diastereomeric Form of an Adduct in the Reaction of Trans-4-nitrochalcone oxide With Thiophenol", *Yakugaku Zasshi*, 1974, 94(10), 1296-1300.
Chemical Abstracts, 77:34207, abstracting Ukai, et al., "Synthesis and Biological Activity of Sulfur Containing Derivatives of Chalcone. II. Reaction of Chalcone Oxides With Thiols", *Yakugaku Zasshi*, 1972, 92(3), 278-283.
Chemical Abstracts, 75:34981, abstracting Baliah, et al., "Dipole Moments of Some Alpha-(Phenylthio)chalcones and Alpha-(Phenylsulfonyl)chalcones", *Indian J. of Chemistry*, 1971, 9(5), 435-438.
Chemical Abstracts, 73:98542, abstracting Baliah, et al., "Synthesis and Configuration of Alpha-(Phenylthio)- and Alpha-(Phenylsulfonyl)chalcones", *Indian J. of Chemistry*, 1970, 8(8), 694-696.
Jurasek, et al., "Synthesis and Properties of β-Ketosulphides and Sulphur Derivatives of Chalcones of 5-Nitrofuran Series", *Tetrahedron*, vol. 34, pp. 1833-1836, 1978.
Chemical Abstracts 97:127484, "Sulfur derivatives of chalcones of the 5-nitrofuran series", 1977.
Chemical Abstracts 121:83000, "New synthesis of polyfunctionally substituted 2-mercaptopyridines and fused pyridines", 1994.
Chemical Abstracts 101:224470, "A study of genetic activity of nitrofuran derivatives", 1984.
Deng, et al., "Syntheis of α-Phenylthioacymethylene Triphenylarsoranes and their Wittig-type Reactions", *J. Chem. Research*, 1999, 144-145.
Chemical Abstracts 127:185438, "Synthesis and antimicrobial activity of .beta.-[(2-benzimidazolyl)thio]-.beta.benzoylstyrene derivatives", 1997.
Chemical Abstracts 138:72927, "Spectral studies and configurational assignments of some 2-propenone derivatives".
Bernard, et al., "Regioselective Synthesis of Trisubstituted 2,3-Dihydrofurans from Donor-Acceptor Cyclopropanes or from Reaction of the Corey Ylide with α-Sulfenyl-, α-Sulfinyl-, or α-Sulfonylenones", *Organic Letters*, vol. 7, No. 21, 4565-4568, 2005.
Chemical Abstratct 97:127484, "Sulfur derivatives of chalcones of the 5-nitrofuran series" (1979).
Chemical Abstracts : I21:83000, "New synthesis of polyfunctionally substituted 2-mercaptopyridines and fused pyridines" (1994).
Chemical Abstracts 101:224470, "A study of genetic activity of nitrofuran derivatives" (1984).
Chemical Abstracts 127:185438, "Synthesis and antimicrobial activity of .beta.-[(2-bensimidazolyl)thio]-.beta.benzoylstyrene derivatives" (1997).
Chemical Abstracts 138:72927, "Spectral studies and configurational assignments of some 2-propenone derivatives" (2002).
Reddy & Reddy, "Synthesis and Spectral Studies of Some (E)-α-[(ARYL) Sulfonyl] Chalcones", *Acta Chimica Hungarica* 120 (4), pp. 275-280 (1985).

* cited by examiner

SULFIDE, SULFOXIDE AND SULFONE CHALCONE ANALOGUES, DERIVATIVES THEREOF AND THERAPEUTIC USES THEREOF

CROSS REFERENCE TO RELATED APPLICATIONS

This application claims the benefit of U.S. Provisional Application No. 60/961,796, filed Jul. 24, 2007, and U.S. Provisional Application No. 60/874,652, filed Dec. 13, 2006, the entire disclosures of which are incorporated herein by reference.

FIELD OF THE INVENTION

The invention relates to compounds, methods for their preparation, compositions including them and methods for the treatment of cellular proliferative disorders, including, but not limited to, cancer.

BACKGROUND OF THE INVENTION

Cellular proliferative disorders such as cancer are among the most common causes of death in developed countries. For diseases for which treatments exist, such as cancer, despite continuing advances, the existing treatments have undesirable side effects and limited efficacy. Identifying new effective drugs for cellular proliferative disorders, including cancer, is a continuing focus of medical research.

SUMMARY OF THE INVENTION

It has been found that certain compounds and compositions are useful for the treatment of cancer and other cellular proliferative disorders. The biologically active compounds of the invention are sulfide, sulfoxide, and sulfone chalcone analogues.

In one aspect, the invention is a compound of formula I, or a salt thereof:

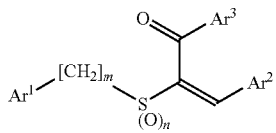

I wherein:

m is 0 or 1;

n is 0, 1, or 2, provided that when m is 0, n is 0 or 1;

$Ar^1$ is selected from the group consisting of unsubstituted aryl, unsubstituted heteroaryl, substituted aryl, and substituted heteroaryl; wherein, when $Ar^1$ is substituted aryl or substituted heteroaryl, said substituted aryl or substituted heteroaryl is aryl or heteroaryl substituted with one or more substituents independently selected from the group consisting of —$R^1$; —$Ar^4$; —$(C_1$-$C_3)$alkylene-$Ar^4$; $(C_2$-$C_6)$alkenyl; $(C_2$-$C_6)$alkynyl; halogen; —NO$_2$; —C(=O)$R^3$; —C(=O)O$R^3$; —C(=O)N$R^4{}_2$; —C(=N$R^3$)N$R^4{}_2$; —O$R^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)N$R^4{}_2$; —N$R^4{}_2$; —N$R^4$C(=O)$R^3$; —N$R^4$C(=O)Ar$^4$; —N$R^4$C(=O)O($C_1$-$C_6$)alkyl; —N$R^4$C(=O)N$R^4{}_2$; —N$R^4$SO$_2$R$^3$; —N$R^4$SO$_2$Ar$^4$; —P(=O)(O$R^3$)$_2$; —OP(=O)(O$R^3$)$_2$; —S(O)$_a$R$^2$; —OSO$_2$($C_1$-$C_6$)alkyl; —OSO$_2$Ar$^4$; —SO$_2$N$R^4{}_2$; and ($C_1$-$C_3$)perfluoroalkyl;

$Ar^2$ is selected from the group consisting of unsubstituted aryl, unsubstituted heteroaryl, substituted aryl, and substituted heteroaryl; wherein, when $Ar^2$ is substituted aryl or substituted heteroaryl, said substituted aryl or substituted heteroaryl is aryl or heteroaryl substituted with one or more substituents independently selected from the group consisting of —$R^1$; —$Ar^4$; —$(C_1$-$C_3)$alkylene-$Ar^4$; $(C_2$-$C_6)$alkenyl; $(C_2$-$C_6)$alkynyl; halogen; —C≡N; —NO$_2$; —C(=O)$R^3$; —C(=O)O$R^3$; —C(=O)N$R^4{}_2$; —C(=N$R^3$)N$R^4{}_2$; —O$R^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)N$R^4{}_2$; —N$R^4{}_2$; —N$R^4$C(=O)$R^3$; —N$R^4$C(=O)Ar$^4$; —N$R^4$C(=O)O($C_1$-$C_6$)alkyl; —N$R^4$C(=O)N$R^4{}_2$; —N$R^4$SO$_2$R$^3$; —N$R^4$SO$_2$Ar$^4$; —P(=O)(O$R^3$)$_2$; —OP(=O)(O$R^3$)$_2$; —S(O)$_a$R$^2$; —OSO$_2$($C_1$-$C_6$)alkyl; —OSO$_2$Ar$^4$; —SO$_2$N$R^4{}_2$; and ($C_1$-$C_3$)perfluoroalkyl;

$Ar^3$ is selected from the group consisting of unsubstituted aryl, unsubstituted heteroaryl, substituted aryl, and substituted heteroaryl; wherein, when $Ar^3$ is substituted aryl or substituted heteroaryl, said substituted aryl or substituted heteroaryl is aryl or heteroaryl substituted with one or more substituents independently selected from the group consisting of —$R^1$; —$Ar^4$; —$(C_1$-$C_3)$alkylene-$Ar^4$; $(C_2$-$C_6)$alkenyl; $(C_2$-$C_6)$alkynyl; halogen; —C≡N; —NO$_2$; —C(=O)$R^3$; —C(=O)O$R^3$; —C(=O)N$R^4{}_2$; —C(=N$R^3$)N$R^4{}_2$; —O$R^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)N$R^4{}_2$; —N$R^4{}_2$; —N$R^4$C(=O)$R^3$; —N$R^4$C(=O)Ar$^4$; —N$R^4$C(=O)O($C_1$-$C_6$)alkyl; —N$R^4$C(=O)N$R^4{}_2$; —N$R^4$SO$_2$R$^3$; —N$R^4$SO$_2$Ar$^4$; —P(=O)(O$R^3$)$_2$; —OP(=O)(O$R^3$)$_2$; —S(O)$_a$R$^2$; —OSO$_2$($C_1$-$C_6$)alkyl; —OSO$_2$Ar$^4$; —SO$_2$N$R^4{}_2$; and ($C_1$-$C_3$)perfluoroalkyl;

each $R^1$ is independently unsubstituted ($C_1$-$C_6$)alkyl or ($C_1$-$C_6$)alkyl substituted with up to five halogen atoms and up to two substituents selected from the group consisting of —C≡N; —C(=O)$R^3$; —C(=O)O$R^3$; —C(=O)N$R^4{}_2$; —O$R^3$; —OC(=O)($C_1$-$C_6$)alkyl; —OC(=O)O($C_1$-$C_6$)alkyl; —OC(=O)N$R^4{}_2$; —N$R^4{}_2$; —N$R^3$C(=O)$R^3$; —N$R^3$C(=O)N$R^4{}_2$; and —S(O)$_a$($C_1$-$C_6$)alkyl;

each $R^2$ is independently selected from the group consisting of hydrogen, $R^1$, $Ar^4$ and ($C_1$-$C_3$)alkylene-$Ar^4$;

each $R^3$ is independently hydrogen or ($C_1$-$C_6$)alkyl;

each $R^4$ is independently hydrogen; ($C_1$-$C_6$)alkyl; —($C_2$-$C_6$)alkylene-O$R^3$; —($C_1$-$C_6$)alkylene-C(=O)O$R^3$; —($C_1$-$C_6$)alkylene-OC(=O)$R^3$; —($C_2$-$C_6$)alkylene-N$R^6{}_2$; —($C_1$-$C_6$)alkylene-C(=O)N$R^6{}_2$; —($C_1$-$C_6$)alkylene-N$R^3$C(=O)$R^3$; —($C_1$-$C_6$)alkylene-N$R^3$C(=O)N$R^6{}_2$; Ar$^4$; or —($C_1$-$C_3$)-alkyleneAr$^4$; or, optionally, within any occurrence of N$R^4{}_2$, independently of any other occurrence of N$R^4{}_2$, the two $R^4$ groups in combination are —(CH$_2$)$_b$— or —(CH$_2$)$_c$A(CH$_2$)$_2$—;

each $R^5$ is independently $Ar^4$ or 1,4-benzoquinon-2-yl optionally substituted with 0, 1, 2, or 3 alkyl groups;

each $R^6$ is independently hydrogen; ($C_1$-$C_6$)alkyl; —($C_2$-$C_6$)alkylene-O$R^3$; —($C_1$-$C_6$)alkylene-C(=O)O$R^3$; —($C_1$-$C_6$)alkylene-OC(=O)$R^3$; ($C_2$-$C_6$)alkylene-N$R^3{}_2$; —($C_1$-$C_6$)alkylene-C(=O)N$R^3{}_2$; —($C_1$-$C_6$)alkylene-N$R^3$C(=O)$R^3$; —($C_1$-$C_6$)alkyleneN$R^3$C(=O)N$R^3{}_2$; —Ar$^4$; or —($C_1$-$C_3$)alkylene-Ar$^4$; or, optionally, within any occurrence of N$R^6{}_2$, independently of any other occurrence of N$R^6{}_2$, the two $R^6$ groups in combination are —(CH$_2$)$_b$— or —(CH$_2$)$_c$A(CH$_2$)$_2$—;

each a is independently selected from the group consisting of 0, 1, and 2;

each b is independently selected from the group consisting of 4, 5, and 6;

each c is independently selected from the group consisting of 2 and 3;

each A is independently selected from the group consisting of O, S, $NR^3$; $NC(=O)R^3$; $NSO_2R^3$; $N(C_2-C_6)$alkylene-$OR^3$; $N(C_1-C_6)$alkylene-$C(=O)OR^3$; $N(C_1-C_6)$alkylene-$OC(=O)R^3$; $N(C_2-C_6)$alkylene-$NR^3_2$; $N(C_1-C_6)$alkylene-$C(=O)NR^3_2$; $N(C_1-C_6)$alkylene-$NR^3C(=O)R^3$; $N(C_1-C_6)$alkylene-$NR^3C(=O)NR^3_2$; $NAr^4$; $N(C_1-C_3)$alkylene-$Ar^4$; and $NC(=O)Ar^4$;

each $Ar^4$ is independently selected from the group consisting of unsubstituted aryl, unsubstituted heteroaryl, and aryl or heteroaryl substituted with one or more substituents independently selected from the group consisting of $(C_1-C_6)$alkyl; $(C_2-C_6)$alkenyl; $(C_2-C_6)$alkynyl; halogen; —C≡N; —$NO_2$; —$C(=O)R^3$; —$C(=O)OR^3$; —$C(=O)NR^3_2$; —$C(=NR^3)NR^3_2$; —$OR^3$; —$OC(=O)(C_1-C_6)$alkyl; —$OC(=O)O(C_1-C_6)$alkyl; —$OC(=O)NR^3_2$; —$NR^3_2$; —$NR^3C(=O)R^3$; —$NR^3C(=O)O(C_1-C_6)$alkyl; —$NR^3C(=O)NR^3_2$; —$P(=O)(OR^3)_2$; —$OP(=O)(OR^3)_2$; —$S(O)_a(C_1-C_6)$alkyl; —$SO_2NR^3_2$; and $(C_1-C_3)$perfluoroalkyl;

with the provisos that:
(i) if $Ar^1$ is substituted phenyl, then $Ar^3$ is other than unsubstituted phenyl or 4-methylphenyl;
(ii) if $Ar^1$ is unsubstituted phenyl and m and n are both zero, then $Ar^3$ is other than 4-nitrophenyl or 4-chlorophenyl;
(iii) if $Ar^1$ is 4-chlorophenyl, $Ar^3$ is unsubstituted phenyl, and m and n are both zero, then $Ar^2$ is other than nitrophenyl or 4-chlorophenyl; and
(iv) if $Ar^2$ and $Ar^3$ are both unsubstituted phenyl, and m and n are both zero, then $Ar^1$ is other than 2-carboxyphenyl.

In another aspect of the invention, there are provided processes for preparing compounds according to formula I, comprising condensing a compound of formula II with an aromatic aldehyde of formula III:

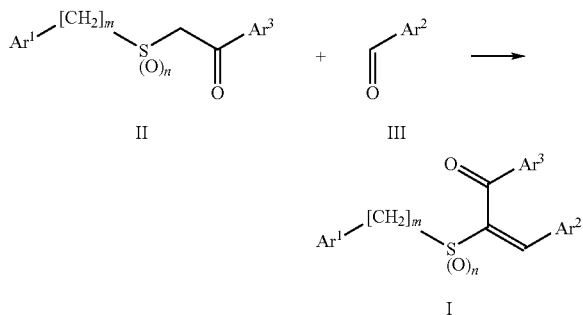

wherein $Ar^1$, $Ar^2$, $Ar^3$, m and n are as defined above for the compounds of formula I.

Another aspect of the invention relates to antibody conjugates of compounds of formula I of the formula I-L-Ab, or a salt thereof, wherein I is a compound of formula I; Ab is an antibody; and -L- is a single bond or a linking group covalently linking said compound of formula I to said antibody.

In another aspect of the invention there are provided pharmaceutical compositions comprising a pharmaceutically acceptable carrier, and a compound according to formula I, or a pharmaceutically acceptable salt thereof. A pharmaceutical composition is additionally provided comprising a pharmaceutically acceptable carrier and at least one conjugate according to formula I-L-Ab, or a pharmaceutically acceptable salt thereof.

According to another embodiment of the invention, a method of treating an individual suffering from a cellular proliferative disorder, particularly cancer, is provided, comprising administering to said individual an effective amount of at least one compound according to formula I, or a pharmaceutically acceptable salt thereof, either alone, or in combination with a pharmaceutically acceptable carrier.

Also provided is a method of inducing apoptosis of cancer cells, preferably tumor cells, in an individual afflicted with cancer is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of treating an individual suffering from a cellular proliferative disorder, particularly cancer, is provided, comprising administering to said individual an effective amount of at least one conjugate of the formula I-L-Ab, either alone, or in combination with a pharmaceutically acceptable carrier.

The invention is also directed to the use in medicine of a compound according to formula I, or a pharmaceutically acceptable salt thereof, or a conjugate according to formula I-L-Ab, or a pharmaceutically acceptable salt thereof.

The invention is also directed to the use of a compound according to formula I, or a pharmaceutically acceptable salt thereof, or a conjugate according to formula I-L-Ab, or a pharmaceutically acceptable salt thereof, in the preparation of a medicament for treatment of a cellular proliferative disorder, particularly cancer, or for inducing apoptosis of tumor cells in an individual affected with cancer.

DETAILED DESCRIPTION OF THE INVENTION

The compounds and compositions of the invention are believed to selectively inhibit proliferation of cancer cells, and kill various tumor cell types without killing (or with reduced killing of) normal cells. Cancer cells are killed at concentrations where normal cells may be temporarily growth-arrested but not killed.

The compounds of the invention are believed to inhibit the proliferation of tumor cells, and for some compounds, induce cell death. Cell death results from the induction of apoptosis. The compounds are believed effective against a broad range of tumor types, including but not limited to the following: ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis and cirrhosis.

I. Definitions

A. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The expression "effective amount", when used to describe therapy to an individual suffering from a cancer or other cellular proliferative disorder, refers to the amount of a compound according to Formula I that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

B. Chemical

In the following paragraphs some of the definitions include examples. The examples are intended to be illustrative, and not limiting.

The term "alkyl", by itself or as part of another substituent means, unless otherwise stated, a straight, branched or cyclic chain hydrocarbon having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "alkenyl" employed alone or in combination with other terms, means, unless otherwise stated, a stable mono-unsaturated or di-unsaturated straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A functional group representing an alkene is exemplified by —CH=CH—$CH_2$—.

"Substituted alkyl" or "substituted alkenyl" means alkyl or alkenyl, as defined above, substituted by one, two or three substituents selected from the group consisting of halogen, —OH, —$NH_2$, —N($CH_3$)$_2$, —C(=O)OH, —C(=O)O($C_1$-$C_4$)alkyl, trifluoromethyl, —C(=O)$NH_2$, —$SO_2NH_2$, —C(=NH)$NH_2$, —C≡N and —$NO_2$, preferably containing one or two substituents selected from halogen, —OH, $NH_2$, —N($CH_3$)$_2$, trifluoromethyl, and —C(=O)OH, more preferably selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "carbamyl" means the group —C(=O)NRR', wherein R and R' are independently selected from hydrogen or a hydrocarbyl functional group, or wherein R and R' combined form a heterocycle. Examples of carbamyl groups include: —C(=O)$NH_2$ and —C(=O)N($CH_3$)$_2$.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

The terms "halo" or "halogen" by themselves or as part of another substituent mean, unless otherwise stated, a fluorine, chlorine, bromine, or iodine atom, preferably, fluorine, chlorine, or bromine, more preferably, fluorine or chlorine.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

The term "phosphonato" means the group —PO(OH)$_2$.

The term "sulfamyl" means the group —$SO_2$NRR', wherein R and R' are independently selected from hydrogen or a hydrocarbyl group, or wherein R and R' combined form a heterocycle. Examples of sulfamyl groups include: —$SO_2NH_2$, —$SO_2$N($CH_3$)$_2$ and —$SO_2$NH($C_6H_5$). Preferred are —$SO_2NH_2$, $SO_2$N($CH_3$)$_2$ and —$SO_2NHCH_3$.

The term "aromatic" refers to a carbocycle or heterocycle having one or more polyunsaturated rings having aromatic character (i.e. having (4n+2) delocalized π (pi) electrons where n is an integer).

The term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-($C_1$-$C_3$)alkyl" means a functional group wherein a one to three carbon alkylene chain is attached to an aryl group, e.g., —CH$_2$CH$_2$-phenyl. Preferred is aryl(CH$_2$)— and aryl(CH(CH$_3$))—. The term "substituted aryl-(C$_1$-C$_3$) alkyl" means an aryl-(C$_1$-C$_3$)alkyl functional group in which the aryl group is substituted. Preferred is substituted aryl (CH$_2$)—. Similarly, the term "heteroaryl(C$_1$-C$_3$)alkyl" means a functional group wherein a one to three carbon alkylene chain is attached to a heteroaryl group, e.g., —CH$_2$CH$_2$-pyridyl. Preferred is heteroaryl(CH$_2$)—. The term "substituted heteroaryl-(C$_1$-C$_3$)alkyl" means a heteroaryl-(C$_1$-C$_3$) alkyl functional group in which the heteroaryl group is substituted. Preferred is substituted heteroaryl(CH$_2$)—.

The term "arylene," by itself or as part of another substituent means, unless otherwise stated, a structure formed by the removal of a hydrogen atom from two carbons in an arene. Preferred are phenyl arylenes, particularly 1,4-phenyl arylenes.

The term "heterocycle" or "heterocyclyl" or "heterocyclic" by itself or as part of another substituent means, unless otherwise stated, an unsubstituted or substituted, stable, mono- or multi-cyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A polycyclic heteroaryl may include one or more rings which are partially saturated. Examples include tetrahydroquinoline and 2,3-dihydrobenzofuryl. For compounds of formula I, the attachment point on ring Ar$^1$, Ar$^2$ or Ar$^3$ is understood to be on an atom which is part of an aromatic monocyclic ring or a ring component of a polycyclic aromatic which is itself an aromatic ring.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

The term "heteroarylene" by itself or as part of another substituent means, unless otherwise stated, an arylene containing at least one hetero atom. Preferred are five- or six-membered monocyclic heteroarylene. More preferred are heteroarylene moieties comprising heteroaryl rings selected from pyridine, piperazine, pyrimidine, pyrazine, furan, thiophene, pyrrole, thiazole, imidazole and oxazole.

For compounds of the present invention, when an aromatic or heteroaromatic ring is attached to a position and the ring comprises a polycyclic ring which is partially saturated, the attachment point on the aromatic or heteroaromatic ring is on a ring atom of an aromatic ring component of the polycyclic ring. For example on the partially saturated heteroaromatic ring, 1,2,3,4-tetrahydroisoquinoline, attachment points would be ring atoms at the 5-, 6-, 7- and 8-positions.

The aforementioned listing of heterocyclyl and heteroaryl moieties is intended to be representative and not limiting.

The term "hydrocarbyl" refers to any moiety comprising only hydrogen and carbon atoms. Preferred hydrocarbyl groups are (C$_1$-C$_{12}$)hydrocarbyl, more preferred are (C$_1$-C$_7$) hydrocarbyl, and most preferred are benzyl and (C$_1$-C$_6$) alkyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

The term "antibody" is intended to encompass not only intact antigen-binding immunoglobulin molecules, but also to include antigen-binding fragments thereof such as Fab, Fab' and F(ab')$_2$ fragments, or any other fragment retaining the antigen-binding ability of an intact antibody.

The term "monospecific polyclonal antibody" means an antibody preparation comprising multiple antibody species having specificity for a single antigen.

The term "peptidyl group" refers to a peptide functional group. Such a functional group has a chemical structure that varies from the structure of the corresponding peptide in that the structural component of the peptide, i.e., an alpha amino group, a side chain amino group, an alpha carboxyl group or a side chain carboxyl group, will form a different functionality when bonded to the molecule of which it is to be a substituent. For example, for a peptide as shown below:

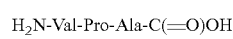

which is a substituent on a compound of formula I, the peptide is coupled to the compound of formula I such that a carboxyl moiety of said peptide is coupled to a free amine moiety on the formula I compound. Elimination of water results in the formation of an amide bond. As a practical result, the corresponding monovalent peptidyl substituent is shown to the left of the dotted line in the depiction below of the aforementioned peptide bonded to a compound of formula I:

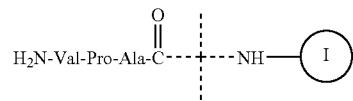

The monovalent peptide group may be attached via either an alpha- or a side chain amino group, or an alpha or side chain carboxyl group. The attachment point on the peptide group will depend on the functionality at the terminus of the group by which the peptide group is connected to the compound of formula I or an antibody.

Specifically, the peptidyl group may be coupled to a connecting group via an alpha amino or a side chain amino group when a connecting group terminates in, for example:

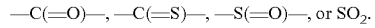

Likewise, the peptidyl group may be coupled to a connecting group via an alpha carboxy or a side chain carboxy group when the connecting group terminates in:

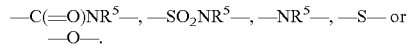

II. Compounds of the Invention

In one aspect, the invention is a compound of formula I, or a salt thereof:

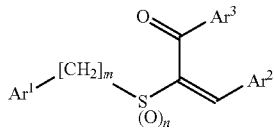

I wherein:

m is 0 or 1;

n is 0, 1, or 2, provided that when m is 0, n is 0 or 1;

$Ar^1$ is selected from the group consisting of unsubstituted aryl, unsubstituted heteroaryl, substituted aryl, and substituted heteroaryl; wherein, when $Ar^1$ is substituted aryl or substituted heteroaryl, said substituted aryl or substituted heteroaryl is aryl or heteroaryl substituted with one or more substituents independently selected from the group consisting of —$R^1$; —$Ar^4$; —($C_1$-$C_3$)alkylene-$Ar^4$; ($C_2$-$C_6$)alkenyl; ($C_2$-$C_6$)alkynyl; halogen; —C≡N; —$NO_2$; —C(=O)$R^3$; —C(=O)$OR^3$; —C(=O)$NR^4_2$; —C(=$NR^3$)$NR^4_2$; —$OR^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)$NR^4_2$; —$NR^4_2$; —$NR^4$C(=O)$R^3$; —$NR^4$C(=O)$Ar^4$; —$NR^4$C(=O)O($C_1$-$C_6$)alkyl; —$NR^4$C(=O)$NR^4_2$; —$NR^4$$SO_2$$R^3$; —$NR^4$$SO_2$$Ar^4$; —P(=O)($OR^3$)$_2$; —OP(=O)($OR^3$)$_2$; —S(O)$_a$$R^2$; —$OSO_2$($C_1$-$C_6$)alkyl; —$OSO_2$$Ar^4$; —$SO_2$$NR^4_2$; and ($C_1$-$C_3$)perfluoroalkyl;

$Ar^2$ is selected from the group consisting of unsubstituted aryl, unsubstituted heteroaryl, substituted aryl, and substituted heteroaryl; wherein, when $Ar^2$ is substituted aryl or substituted heteroaryl, said substituted aryl or substituted heteroaryl is aryl or heteroaryl substituted with one or more substituents independently selected from the group consisting of —$R^1$; —$Ar^4$; —($C_1$-$C_3$)alkylene-$Ar^4$; ($C_2$-$C_6$)alkenyl; ($C_2$-$C_6$)alkynyl; halogen; —C≡N; —$NO_2$; —C(=O)$R^3$; —C(=O)$OR^3$; —C(=O)$NR^4_2$; —C(=$NR^3$)$NR^4_2$; —$OR^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)$NR^4_2$; —$NR^4_2$; —$NR^4$C(=O)$R^3$; —$NR^4$C(=O)$Ar^4$; —$NR^4$C(=O)O($C_1$-$C_6$)alkyl; —$NR^4$C(=O)$NR^4_2$; —$NR^4$$SO_2$$R^3$; —$NR^4$$SO_2$$Ar^4$; —P(=O)($OR^3$)$_2$; —OP(=O)($OR^3$)$_2$; —S(O)$_a$$R^2$; —$OSO_2$($C_1$-$C_6$)alkyl; —$OSO_2$$Ar^4$; —$SO_2$$NR^4_2$; and ($C_1$-$C_3$)perfluoroalkyl;

$Ar^3$ is selected from the group consisting of unsubstituted aryl, unsubstituted heteroaryl, substituted aryl, and substituted heteroaryl; wherein, when $Ar^3$ is substituted aryl or substituted heteroaryl, said substituted aryl or substituted heteroaryl is aryl or heteroaryl substituted with one or more substituents independently selected from the group consisting of —$R^1$; —$Ar^4$; —($C_1$-$C_3$)alkylene-$Ar^4$; ($C_2$-$C_6$)alkenyl; ($C_2$-$C_6$)alkynyl; halogen; —C≡N; —$NO_2$; —C(=O)$R^3$; —C(=O)$OR^3$; —C(=O)$NR^4_2$; —C(=$NR^3$)$NR^4_2$; —$OR^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)$NR^4_2$; —$NR^4_2$; —$NR^4$C(=O)$R^3$; —$NR^4$C(=O)$Ar^4$; —$NR^4$C(=O)O($C_1$-$C_6$)alkyl; —$NR^4$C(=O)$NR^4_2$; —$NR^4$$SO_2$$R^3$; —$NR^4$$SO_2$$Ar^4$; —P(=O)($OR^3$)$_2$; —OP(=O)($OR^3$)$_2$; —S(O)$_a$$R^2$; —$OSO_2$($C_1$-$C_6$)alkyl; —$OSO_2$$Ar^4$; —$SO_2$$NR^4_2$; and ($C_1$-$C_3$)perfluoroalkyl;

each $R^1$ is independently unsubstituted ($C_1$-$C_6$)alkyl or ($C_1$-$C_6$)alkyl substituted with up to five halogen atoms and up to two substituents selected from the group consisting of —C≡N; —C(=O)$R^3$; —C(=O)$OR^3$; —C(=O)$NR^4_2$; —$OR^3$; —OC(=O)($C_1$-$C_6$)alkyl; —OC(=O)O($C_1$-$C_6$)alkyl; —OC(=O)$NR^4_2$; —$NR^4_2$; —$NR^3$C(=O)$R^3$; —$NR^3$C(=O)$NR^4_2$; and —S(O)$_a$($C_1$-$C_6$)alkyl;

each $R^2$ is independently selected from the group consisting of hydrogen, $R^1$, $Ar^4$ and ($C_1$-$C_3$)alkylene-$Ar^4$.

each $R^3$ is independently hydrogen or ($C_1$-$C_6$)alkyl;

each $R^4$ is independently hydrogen; ($C_1$-$C_6$)alkyl; —($C_2$-$C_6$)alkylene-$OR^3$; —($C_1$-$C_6$)alkylene-C(=O)$OR^3$; —($C_1$-$C_6$)alkylene-OC(=O)$R^3$; —($C_2$-$C_6$)alkylene-$NR^6_2$; —($C_1$-$C_6$)alkylene-C(=O)$NR^6_2$; —($C_1$-$C_6$)alkylene-$NR^3$C(=O)$R^3$; —($C_1$-$C_6$)alkylene-$NR^3$C(=O)$NR^6_2$; $Ar^4$; or —($C_1$-$C_3$)-alkyleneAr$^4$; or, optionally, within any occurrence of $NR^4_2$, independently of any other occurrence of $NR^4_2$, the two $R^4$ groups in combination are —($CH_2$)$_b$— or —($CH_2$)$_c$A($CH_2$)$_2$—;

each $R^5$ is independently $Ar^4$ or 1,4-benzoquinon-2-yl optionally substituted with 0, 1, 2, or 3 alkyl groups;

each $R^6$ is independently hydrogen; ($C_1$-$C_6$)alkyl; —($C_2$-$C_6$)alkylene-$OR^3$; —($C_1$-$C_6$)alkylene-C(=O)$OR^3$; —($C_1$-$C_6$)alkylene-OC(=O)$R^3$; ($C_2$-$C_6$)alkylene-$NR^3_2$; —($C_1$-$C_6$)alkylene-C(=O)$NR^3_2$; —($C_1$-$C_6$)alkylene-$NR^3$C(=O)$R^3$; —($C_1$-$C_6$)alkylene$NR^3$C(=O)$NR^3_2$; —$Ar^4$; or —($C_1$-$C_3$)alkylene-$Ar^4$; or, optionally, within any occurrence of $NR^6_2$, independently of any other occurrence of $NR^6_2$, the two $R^6$ groups in combination are —($CH_2$)$_b$— or —($CH_2$)$_c$A($CH_2$)$_2$—;

each a is independently selected from the group consisting of 0, 1, and 2;

each b is independently selected from the group consisting of 4, 5, and 6;

each c is independently selected from the group consisting of 2 and 3;

each A is independently selected from the group consisting of O, S, $NR^3$; NC(=O)$R^3$; $NSO_2$$R^3$; N($C_2$-$C_6$)alkylene-$OR^3$; N($C_1$-$C_6$)alkylene-C(=O)$OR^3$; N($C_1$-$C_6$)alkylene-OC(=O)$R^3$; N($C_2$-$C_6$)alkylene-$NR^3_2$; N($C_1$-$C_6$)alkylene-C(=O)$NR^3_2$; N($C_1$-$C_6$)alkylene-$NR^3$C(=O)$R^3$; N($C_1$-$C_6$)alkylene-$NR^3$C(=O)$NR^3_2$; $NAr^4$; N($C_1$-$C_3$)alkylene-$Ar^4$; and NC(=O)$Ar^4$;

each $Ar^4$ is independently selected from the group consisting of unsubstituted aryl, unsubstituted heteroaryl, and aryl or heteroaryl substituted with one or more substituents independently selected from the group consisting of ($C_1$-$C_6$)alkyl; ($C_2$-$C_6$)alkenyl; ($C_2$-$C_6$)alkynyl; halogen; —C≡N; —$NO_2$; —C(=O)$R^3$; —C(=O)$OR^3$; —C(=O)$NR^3_2$; —C(=$NR^3$)$NR^3_2$; —$OR^3$; —OC(=O)($C_1$-$C_6$)alkyl; —OC(=O)O($C_1$-$C_6$)alkyl; —OC(=O)$NR^3_2$; —$NR^3_2$; —$NR^3$C(=O)$R^3$; —$NR^3$C(=O)O($C_1$-$C_6$)alkyl; —$NR^3$C(=O)$NR^3_2$;

—P(=O)(OR$^3$)$_2$; —OP(=O)(OR$^3$)$_2$; —S(O)$_a$(C$_1$-C$_6$)alkyl; —SO$_2$NR$^3$$_2$; and (C$_1$-C$_3$)perfluoroalkyl;

with the provisos that:
(i) if Ar$^1$ is substituted phenyl, then Ar$^3$ is other than unsubstituted phenyl or 4-methylphenyl;
(ii) if Ar$^1$ is unsubstituted phenyl and m and n are both zero, then Ar$^3$ is other than 4-nitrophenyl or 4-chlorophenyl;
(iii) if Ar$^1$ is 4-chlorophenyl, Ar$^3$ is unsubstituted phenyl, and m and n are both zero, then Ar$^2$ is other than nitrophenyl or 4-chlorophenyl; and
(iv) if Ar$^2$ and Ar$^3$ are both unsubstituted phenyl, and m and n are both zero, then Ar$^1$ is other than 2-carboxyphenyl.

Particular embodiments of the invention are compounds according to formula I wherein:

m is 0 or 1;
n is 0, 1, or 2, provided that when m is 0, n is 0 or 1;
Ar$^1$, Ar$^2$, and Ar$^3$ are independently selected from the group consisting of unsubstituted aryl, unsubstituted heteroaryl, substituted aryl, and substituted heteroaryl;
wherein, when Ar$^1$, Ar$^2$, or Ar$^3$ is substituted aryl or substituted heteroaryl, said substituted aryl or substituted heteroaryl is aryl or heteroaryl substituted with one or more substituents independently selected from the group consisting of —R$^1$; (C$_2$-C$_6$)alkenyl; (C$_2$-C$_6$)alkynyl; halogen; —C≡N; —NO$_2$; —C(=O)R$^3$; —C(=O)OR$^3$; —C(=O)NR$^4$$_2$; —C(=NR$^3$)NR$^4$$_2$; —OR$^2$; —OC(=O)(C$_1$-C$_6$)alkyl; —OC(=O)O(C$_1$-C$_6$)alkyl; —OC(=O)NR$^4$$_2$; —NR$^4$$_2$; —NR$^3$C(=O)R$^3$; —NR$^3$C(=O)Ar$^4$; —NR$^3$C(=O)O(C$_1$-C$_6$)alkyl; —NR$^3$C(=O)NR$^4$$_2$; —P(=O)(OR$^3$)$_2$; —OP(=O)(OR$^3$)$_2$; —S(O)$_a$(C$_1$-C$_6$)alkyl; —SO$_2$NR$^4$$_2$; and (C$_1$-C$_3$)perfluoroalkyl;
each R$^1$ is independently unsubstituted (C$_1$-C$_6$)alkyl or (C$_1$-C$_6$)alkyl substituted with up to five halogen atoms and up to two substituents selected from the group consisting of —C≡N; —C(=O)R$^3$; —C(=O)OR$^3$; —C(=O)NR$^4$$_2$; —OR$^3$; —OC(=O)(C$_1$-C$_6$)alkyl; —OC(=O)O(C$_1$-C$_6$)alkyl; —OC(=O)NR$^4$$_2$; —NR$^4$$_2$; —NR$^3$C(=O)R$^3$; —NR$^3$C(=O)NR$^4$$_2$; and S(O)$_a$(C$_1$-C$_6$)alkyl;
each R$^2$ is independently selected from the group consisting of hydrogen, R$^1$, Ar$^4$ and (C$_1$-C$_3$)alkylene-Ar$^4$;
each R$^3$ is independently hydrogen or (C$_1$-C$_6$)alkyl;
each R$^4$ is independently hydrogen or (C$_1$-C$_6$)alkyl; or, optionally, within any occurrence of NR$^4$$_2$, independently of any other occurrence of NR$^4$$_2$, the two R$^4$ groups in combination are —(CH$_2$)$_b$— or —(CH$_2$)$_c$A(CH$_2$)$_2$—;
each a is independently selected from the group consisting of 0, 1, and 2;
each b is independently selected from the group consisting of 4, 5, and 6;
each c is independently selected from the group consisting of 2 and 3;
each A is independently selected from the group consisting of O, S, NR$^3$; and NC(=O)R$^3$; and
each Ar$^4$ is independently selected from the group consisting of unsubstituted aryl, unsubstituted heteroaryl, and aryl or heteroaryl substituted with one or more substituents independently selected from the group consisting of (C$_1$-C$_6$)alkyl; (C$_2$-C$_6$)alkenyl; (C$_2$-C$_6$)alkynyl; halogen; —CN; —NO$_2$; —C(=O)R$^3$; —C(=O)OR$^3$; —C(=O)NR$^4$$_2$; —C(=NR$^3$)NR$^4$$_2$; —OR$^3$; —OC(=O)(C$_1$-C$_6$)alkyl; —OC(=O)O(C$_1$-C$_6$)alkyl; —OC(=O)NR$^4$$_2$; —NR$^4$$_2$; —NR$^3$C(=O)R$^3$; —NR$^3$C(=O)O(C$_1$-C$_6$)alkyl; —NR$^3$C(=O)NR$^4$$_2$; —P(=O)(OR$^3$)$_2$; —OP(=O)(OR$^3$)$_2$; —S(O)$_a$(C$_1$-C$_6$)alkyl; —SO$_2$NR$^4$$_2$; and (C$_1$-C$_3$)perfluoroalkyl;

with the provisos that:
(i) if Ar$^1$ is substituted phenyl, then Ar$^3$ is other than unsubstituted phenyl or 4-methylphenyl;
(ii) if Ar$^1$ is unsubstituted phenyl and m and n are both zero, then Ar$^3$ is other than 4-nitrophenyl or 4-chlorophenyl;
(iii) if Ar$^1$ is 4-chlorophenyl, Ar$^3$ is unsubstituted phenyl, and m and n are both zero, then Ar$^2$ is other than nitrophenyl or 4-chlorophenyl; and
(iv) if Ar$^2$ and Ar$^3$ are both unsubstituted phenyl, and m and n are both zero, then Ar$^1$ is other than 2-carboxyphenyl.

In the compounds of the invention, the stereochemistry of the S—C=C—Ar$^2$ double bond is E.

In other particular embodiments of the invention, Ar$^1$ and Ar$^3$ are independently selected from the group consisting of unsubstituted and substituted phenyl, preferably substituted phenyl.

In particular embodiments of the invention, Ar$^1$ is mono- or di-substituted phenyl. In particular embodiments, Ar$^1$ is 2-, 3- or 4-monosubstituted, or 2,3-, 2,4-, 2,5-, 2,6-, 3,4- or 3,5-disubstituted. In particular embodiments, Ar$^1$ is substituted phenyl wherein the phenyl substituents are selected from the group consisting of (C$_1$-C$_6$)alkyl, halogen, and (C$_1$-C$_6$)alkoxy. In other particular embodiments, Ar$^1$ is monosubstituted phenyl, for example 4-monosubstituted phenyl, for example 4-(C$_1$-C$_6$)alkyl, 4-halogen, and 4-(C$_1$-C$_6$)alkoxy, such as 4-methylphenyl, 4-fluorophenyl, 4-chlorophenyl, and 4-bromophenyl. In other embodiments, Ar$^1$ is pentahalophenyl, for example pentafluorophenyl.

In particular embodiments of the invention, Ar$^3$ is mono- or di-substituted phenyl. In particular embodiments, Ar$^3$ is 2-, 3- or 4-monosubstituted, or 2,3-, 2,4-, 2,5-, 2,6-, 3,4- or 3,5-disubstituted. In particular embodiments, Ar$^3$ is substituted phenyl wherein the phenyl substituents are selected from the group consisting of (C$_1$-C$_6$)alkyl, halogen, (C$_1$-C$_6$)alkoxy, —C≡N; —NO$_2$; or —C(=O)OH. In other particular embodiments, Ar$^3$ is monosubstituted phenyl, for example 4-monosubstituted phenyl, for example 4-(C$_1$-C$_6$)alkyl, 4-halo, and 4-(C$_1$-C$_6$)alkoxy, 4-cyano, 4-nitro; or 4-carboxy, such as 4-methylphenyl, 4-fluorophenyl, 4-chlorophenyl, 4-bromophenyl, 4-methoxyphenyl, 4-cyanophenyl, 4-nitrophenyl, or 4-carboxyphenyl. In other embodiments, Ar$^3$ is pentahalophenyl, for example pentafluorophenyl. Preferred embodiments include those wherein Ar$^3$ is phenyl substituted, preferably at the 4-position, with —C(=O)OH, and preferably monosubstituted, preferably at the 4-position with —C(=O)OH.

In other particular embodiments of the invention, Ar$^2$ is selected from the group consisting of unsubstituted and substituted phenyl; unsubstituted and substituted biphenyl; unsubstituted and substituted indolyl; unsubstituted and substituted pyrrolyl; and unsubstituted and substituted thiophenyl.

In particular embodiments of the invention, Ar$^2$ is mono-, di- or tri-substituted phenyl. In particular embodiments, Ar$^3$ is 2-, 3- or 4-monosubstituted, 2,3-, 2,4-, 2,5-, 2,6-, 3,4- or 3,5-disubstituted, or 2,3,4-, 2,3,5-, 2,3,6-, 2,4,5-, 2,4,6- or 3,4,5-trisubstituted. In particular embodiments, Ar$^2$ is substituted phenyl wherein the phenyl substituents are selected from the group consisting of (C$_1$-C$_6$)alkyl; phenyl; —(C$_1$-C$_3$)alkylene-Ph; halogen; —C≡N; —NO$_2$; —C(=O)R$^3$; —C(=O)OR$^3$, particularly —C(=O)OH or —C(=O)O(C$_1$-C$_6$)alkyl; —C(=O)NR$^4$$_2$, —OR$^2$ particularly —OH or —C(=O)O(C$_1$-C$_6$)alkyl; —O(C$_1$-C$_6$)alkyl; —OC(=O)(C$_1$-C$_6$)alkyl; —OC(=O)NR$^4$$_2$, —NR$^4$$_2$ particularly NH$_2$, NH(C$_1$-C$_6$)alkyl, or N((C$_1$-C$_6$)alkyl)$_2$, or those embodiments wherein the two R$^4$ groups in combination comprise a piperazine ring; —NR$^4$C(=O)R$^3$; —NR$^4$C(=O)Ar$^4$; —NR$^4$C —C(=O)O(C$_1$-C$_6$)alkyl; —NR$^4$C(=O)NR$^4$$_2$; —NR$^4$SO$_2$R$^3$; —NR$^4$SO$_2$Ar$^4$; —P(=O)(OR$^3$)$_2$; —OP(=O)(OR$^3$)$_2$; —S(O)$_a$R$^2$; —OSO$_2$(C$_1$-C$_6$)alkyl; —OSO$_2$Ar$^4$; —SO$_2$NR$^4$$_2$; and (C$_1$-C$_3$)perfluoroalkyl. In other particular embodiments, Ar$^3$ is monosubstituted phenyl, for example 4-monosubstituted phenyl, for example 4-(C$_1$-C$_6$)alkyl, 4-halo, and 4-(C$_1$-C$_6$)alkoxy, 4-cyano, 4-nitro; or 4-carboxy, such as 4-methylphenyl, 4-fluorophenyl, 4-chlorophenyl, 4-bromophenyl, 4-methoxyphenyl, 4-cyanophenyl, 4-nitrophenyl, or 4-carboxyphenyl. In other particular embodiments, Ar$^2$ is disubstituted phenyl, for example 3,4-disubstituted phenyl, for example phenyl substituted at the 3-position with nitro and at the 4-position with, for example, halogen, particularly fluorine, NH$_2$, NH(C$_1$-C$_6$)alkyl, or N((C$_1$-C$_6$)alkyl)$_2$, or those embodiments wherein the two R4 groups in combination comprise a piperazine ring. In other embodiments, Ar$^2$ is pentahalophenyl, for example pentafluorophenyl. In particular embodiments wherein Ar$^2$ is heteroaryl, Ar$^2$ is either unsubstituted or is substituted, preferably monosubstituted, with halogen, —C(=O)OR$^3$ or —C(=O)NR$^4$$_2$.

In particular embodiments of the invention, each of Ar$^1$, Ar$^2$, or Ar$^3$ is other than unsubstituted phenyl. In particular embodiments thereof, each of Ar$^1$ and Ar$^3$ is substituted phenyl and or Ar$^2$ is either substituted phenyl or unsubstituted or substituted heteroaryl. In particular embodiments, each of Ar$^1$, Ar$^2$, and Ar$^3$ is substituted phenyl.

In some embodiments of the invention, m is 0.

In some embodiments of the invention, both m and n are 0. Particular embodiments of the invention wherein both m and n are 0 are those wherein Ar$^1$, Ar$^2$, and Ar$^3$ are as in the particular embodiments of the compounds of formula I described above.

In some embodiments of the invention, m is 0 and n is 1. Particular embodiments of the invention wherein m is 0 and n is 1 are those wherein Ar$^1$, Ar$^2$, and Ar$^3$ are as in the particular embodiments of the compounds of formula I described above.

In some embodiments of the invention m is 1.

In some embodiments of the invention, m is 1 and n is 0. Particular embodiments of the invention wherein m is 1 and n is 0 are those wherein Ar$^1$, Ar$^2$, and Ar$^3$ are as in the particular embodiments of the compounds of formula I described above.

In some embodiments of the invention, m and n are both 1. Particular embodiments of the invention wherein m and n are both 1 are those wherein Ar$^1$, Ar$^2$, and Ar$^3$ are as in the particular embodiments of the compounds of formula I described above.

In some embodiments of the invention, m is 1 and n is 2. Particular embodiments of the invention wherein m is 1 and n is 2 are those wherein Ar$^1$, Ar$^2$, and Ar$^3$ are as in the particular embodiments of the compounds of formula I described above.

Particular compounds that are embodiments of the invention wherein m and n are both 0 include (E)-1-(4-bromophenyl)-2-(2-bromophenylsulfenyl)-3-(4-bromophenyl)prop-2-en-1-one; (E)-1-(4-bromophenyl)-2-(4-bromophenylsulfenyl)-3-(2,4-dichlorophenyl)prop-2-en-1-one; (E)-1-(4-bromophenyl)-2-(4-bromophenylsulfenyl)-3-(2,4-difluorophenyl)prop-2-en-1-one; (E)-1-(4-chlorophenyl)-2-(4-bromophenylsulfenyl)-3-(2,4-difluorophenyl)prop-2-en-1-one; (E)-1-(4-bromophenyl)-2-(4-bromophenylsulfenyl)-3-(2-chloro-4-fluorophenyl)prop-2-en-1-one; (E)-1-(2,3,4,5,6-pentafluorophenyl)-2-(4-bromophenylsulfenyl)-3-(3-bromo-4-hydroxyphenyl)prop-2-en-1-one; (E)-1-(2,3,4,5,6-pentafluorophenyl)-2-(4-bromophenylsulfenyl)-3-(3-hydroxy-4-nitrophenyl)prop-2-en-1-one; (E)-1-(4-bromophenyl)-2-(4-bromophenylsulfenyl)-3-(3-indolyl)prop-2-en-1-one; (E)-1-(4-bromophenyl)-2-(4-bromophenylsulfenyl)-3-(4-bromo-3-hydroxyphenyl)prop-2-en-1-one; (E)-1-(4-bromophenyl)-2-(4-bromophenylsulfenyl)-3-(4-bromo-3-nitrophenyl)prop-2-en-1-one; (E)-1-(4-bromophenyl)-2-(4-bromophenylsulfenyl)-3-(4-bromophenyl)prop-2-en-1-one; (E)-1-(4-chlorophenyl)-2-(4-bromophenylsulfenyl)-3-(4-bromophenyl)prop-2-en-1-one; (E)-1-(4-bromophenyl)-2-(4-bromophenylsulfenyl)-3-(4-chloro-3-nitrophenyl)prop-2-en-1-one; (E)-1-(4-bromophenyl)-2-(4-bromophenylsulfenyl)-3-(4-chlorophenyl)prop-2-en-1-one; (E)-1-(4-bromophenyl)-2-(4-bromophenylsulfenyl)-3-(4-hydroxy-3-methoxyphenyl)prop-2-en-1-one; (E)-1-(2,3,4,5,6-pentafluorophenyl)-2-(4-bromophenylsulfenyl)-3-(4-hydroxy-3-nitrophenyl)prop-2-en-1-one; (E)-1-(4-bromophenyl)-2-(4-bromophenylsulfenyl)-3-(4-hydroxy-3-nitrophenyl)prop-2-en-1-one; (E)-1-(4-bromophenyl)-2-(4-bromophenylsulfenyl)-3-(4-iodophenyl)prop-2-en-1-one; (E)-1-(4-bromophenyl)-2-(4-bromophenylsulfenyl)-3-(4-trifluoromethoxyphenyl)prop-2-en-1-one; (E)-1-(4-bromophenyl)-2-(4-bromophenylsulfenyl)-3-(5-methoxy-3-indolyl)prop-2-en-1-one; (E)-1-(4-chlorophenyl)-2-(4-chlorophenylsulfenyl)-3-(4-chlorophenyl)prop-2-en-1-one; (E)-1-(4-chlorophenyl)-2-(4-fluorophenylsulfenyl)-3-(2-benzyloxyphenyl)prop-2-en-1-one; (E)-1-(4-bromophenyl)-2-(4-methoxyphenylsulfenyl)-3-(2,4-dichlorophenyl)prop-2-en-1-one; (E)-1-(4-chlorophenyl)-2-(4-methoxyphenylsulfenyl)-3-(2-benzyloxyphenyl)prop-2-en-1-one; (E)-1-(4-chlorophenyl)-2-(4-methylphenylsulfenyl)-3-(3-hydroxy-4-methoxyphenyl)prop-2-en-1-one; (E)-1-(4-chlorophenyl)-2-(4-methylphenylsulfenyl)-3-(4-methoxyphenyl)prop-2-en-1-one; (E)-1-(4-chlorophenyl)-2-(4-methylphenylsulfenyl)-3-(5-bromo-3-indolyl)prop-2-en-1-one; (E)-1-(4-bromophenyl)-2-(4-methylphenylsulfenyl)-3-(5-chloro-3-indolyl)prop-2-en-1-one; (E)-1-(4-chlorophenyl)-2-(4-methylphenylsulfenyl)-3-(5-chloro-3-indolyl)prop-2-en-1-one; (E)-1-(4-bromophenyl)-2-(2,3,4,5,6-pentafluorophenylsulfenyl)-3-(3-hydroxy-4-nitrophenyl)prop-2-en-1-one; (E)-1-(4-bromophenyl)-2-(2-bromophenylsulfenyl)-3-(4-hydroxy-3-nitrophenyl)prop-2-en-1-one; (E)-1-(4-bromophenyl)-2-(4-bromophenylsulfenyl)-3-(2-fluoro-4-methoxyphenyl)prop-2-en-1-one; (E)-1-(4-chlorophenyl)-2-(4-bromophenylsulfenyl)-3-(2-fluorophenyl)prop-2-en-1-one; (E)-1-(4-chlorophenyl)-2-(4-bromophenylsulfenyl)-3-(3,5-dimethylphenyl)prop-2-en-1-one; (E)-1-(4-bromophenyl)-2-(4-bromophenylsulfenyl)-3-(4-fluoro-3-methoxyphenyl)prop-2-en-1-one; (E)-1-(4-bromophenyl)-2-(4-bromophenylsulfenyl)-3-(4-fluorophenyl)prop-2-en-1-one; (E)-1-(4-chlorophenyl)-2-(4-bromophenylsulfenyl)-3-(4-methanesulfenylphenyl)prop-2-en-1-one; (E)-1-(4-methoxyphenyl)-2-(4-fluorophenylsulfenyl)-3-(3-hydroxy-4-methoxyphenyl)prop-2-en-1-one; (E)-1-(4-chlorophenyl)-2-(4-methylphenylsulfenyl)-3-(2-fluoro-5-nitrophenyl)prop-2-en-1-one; E-1-(4-chlorophenyl)-2-(4-methylphenylsulfenyl)-3-(3-indolyl)prop-2-en-1-one; (E)-1-(4-chlorophenyl)-2-(4-methylphenylsulfenyl)-3-(4-acetoxyphenyl)prop-2-en-1-one; (E)-1-(4-bromophenyl)-2-(4-methylphenylsulfenyl)-3-(4-chlorophenyl)prop-2-en-1-one; (E)-1-(4-bromophenyl)-2-(4-methylphenylsulfenyl)-3-(4-phenoxyphenyl)prop-2-en-1-one; (E)-1-(4-bromophenyl)-2-(4-methylphenylsulfenyl)-3-(5-bromo-3-indolyl)prop-2-en-1-one; (E)-1-(4-bromophenyl)-2-(2,3,4,5,6-pentafluorophenylsulfenyl)-3-(4-hydroxy-3-nitrophenyl)prop-2-en-1-one; (E)-1-(4-chlorophenyl)-2-(4-bromophenylsulfenyl)-3-(2,5-dimethylphenyl)prop-2-en-1- one; (E)-1-(4-chlorophenyl)-2-(4-bromophenylsulfenyl)-3-(2-benzyloxyphenyl)prop-2-en-1-one; (E)-1-(4-chlorophenyl)-2-(4-bromophenylsulfenyl)-3-(2-methoxyphenyl)prop-2-en-1-one; (E)-1-(4-bromophenyl)-2-(4-bromophenylsulfenyl)-3-(4-methoxyphenyl)prop-2-en-1-one; (E)-1-(4-methoxyphenyl)-2-(4-fluorophenylsulfenyl)-3-(4-methoxyphenyl)prop-2-en-1-one; (E)-1-(4-bromophenyl)-2-(4-methoxyphenylsulfenyl)-3-(4-bromophenyl)prop-2-en-1-one; (E)-1-(4-chlorophenyl)-2-(4-methylphenylsulfenyl)-3-(2,4-dichlorophenyl)prop-2-en-1-one; (E)-1-(4-chlorophenyl)-2-(4-methylphenylsulfenyl)-3-(2-pyrrolyl)prop-2-en-1-one; (E)-1-(4-bromophenyl)-2-(4-methylphenylsulfenyl)-3-(3-indolyl)prop-2-en-1-one; (E)-1-(4-chlorophenyl)-2-(4-methylphenylsulfenyl)-3-(4-chlorophenyl)prop-2-en-1-one; (E)-1-(4-bromophenyl)-2-(4-methylphenylsulfenyl)-3-(4-fluoro-3-methylphenyl)prop-2-en-1-one; (E)-1-(4-bromophenyl)-2-(4-methylphenylsulfenyl)-3-(4-methanesulfenylphenyl)prop-2-en-1-one; (E)-1-(4-chlorophenyl)-2-(4-methylphenylsulfenyl)-3-(4-phenoxyphenyl)prop-2-en-1-one; (E)-1-(4-chlorophenyl)-2-(2-bromophenylsulfenyl)-3-(4-hydroxy-3-nitrophenyl)prop-2-en-1-one; (E)-1-(4-chlorophenyl)-2-(4-bromophenylsulfenyl)-3-(4-methoxyphenyl)prop-2-en-1-one; (E)-1-(4-chlorophenyl)-2-(4-methylphenylsulfenyl)-3-(2-methoxyphenyl)prop-2-en-1-one; (E)-1-(4-chlorophenyl)-2-(4-methylphenylsulfenyl)-3-(4-ethoxy-3-methoxyphenyl)prop-2-en-1-one; (E)-1-(4-chlorophenyl)-2-(4-methylphenylsulfenyl)-3-(4-hydroxy-3-nitrophenyl)prop-2-en-1-one; (E)-1-(4-bromophenyl)-2-(4-methylphenylsulfenyl)-3-(4-methanesulfenylphenyl)prop-2-en-1-one; (E)-1-(2,3,4,5,6-pentafluorophenyl)-2-(4-bromophenylsulfenyl)-3-(3-carboxy-4-hydroxyphenyl)prop-2-en-1-one; (E)-1-(4-bromophenyl)-2-(4-bromophenylsulfenyl)-3-(4-hydroxy-3-nitrophenyl)prop-2-en-1-one; (E)-1-(4-chlorophenyl)-2-(4-fluorophenylsulfenyl)-3-(5-methylthiophen-2-yl)prop-2-en-1-one; (E)-1-(4-chlorophenyl)-2-(4-methylphenylsulfenyl)-3-(2,3,4,5,6-pentafluorophenyl)prop-2-en-1-one; (E)-1-(4-bromophenyl)-2-(4-methylphenylsulfenyl)-3-(4-fluoro-2-trifluoromethoxyphenyl)prop-2-en-1-one; and (E)-1-(4-bromophenyl)-2-(4-methylphenylsulfenyl)-3-(4-methoxyphenyl)prop-2-en-1-one; and salts thereof.

Other particular compounds that are embodiments of the invention wherein m is 0 and n is 0 include (E)-1-(4-bromophenyl)-2-(4-methylphenylsulfenyl)-3-(4-fluoro-3-nitrophenyl)prop-2-en-1-one; and (E)-1-(4-carboxyphenyl)-2-(2,3,4,5,6-pentafluorophenylsulfenyl)-3-(4-fluoro-3-nitrophenyl)prop-2-en-1-one and salts thereof.

Particular compounds that are embodiments of the invention wherein m is 1 and n is 0 include (E)-1-(4-carboxyphenyl)-2-(4-bromophenylmethylsulfenyl)-3-(4-chloro-3-nitrophenyl)prop-2-en-1-one; (E)-1-(4-carboxyphenyl)-2-(4-chlorophenylmethylsulfenyl)-3-(4-bromo-3-nitrophenyl)prop-2-en-1-one; (E)-1-(4-carboxyphenyl)-2-(4-chlorophenylmethylsulfenyl)-3-(4-chloro-3-nitrophenyl)prop-2-en-1-one; (E)-1-(4-carboxyphenyl)-2-(4-fluorophenylmethylsulfenyl)-3-(4-bromo-3-nitrophenyl)prop-2-en-1-one; (E)-1-(4-carboxyphenyl)-2-(4-fluorophenylmethylsulfenyl)-3-(4-chloro-3-nitrophenyl)prop-2-en-1-one; (E)-1-(4-carboxyphenyl)-2-(4-methylphenylmethylsulfenyl)-3-(4-chloro-3-nitrophenyl)prop-2-en-1-one; (E)-1-(4-chlorophenyl)-2-(4-chlorophenylmethylsulfenyl)-3-(3-hydroxy-4-methoxyphenyl)prop-2-en-1-one; (E)-1-(2-chlorophenyl)-2-(2-chlorophenylmethylsulfenyl)-3-(4-benzyloxyphenyl)prop-2-en-1-one; (E)-1-(3,4,5-trimethoxyphenyl)-2-(4-bromophenylmethylsulfenyl)-3-(4-hydroxy-3-nitrophenyl)prop-2-en-1-one; (E)-1-(3-chloro-4-nitrophenyl)-2-(4-bromophenylmethylsulfenyl)-3-(3-hydroxy-4-nitrophenyl)prop-2-en-1-one; (E)-1-(3-chloro-4-nitrophenyl)-2-(4-bromophenylmethylsulfenyl)-3-(4-hydroxy-3-nitrophenyl)prop-2-en-1-one; (E)-1-(4-bromophenyl)-2-(3-chlorophenylmethylsulfenyl)-3-(4-benzyloxyphenyl)prop-2-en-1-one; (E)-1-(4-bromophenyl)-2-(4-bromophenylmethylsulfenyl)-3-(4-(2-(N,N-diethylamino)ethylcarbamoyl)-3,5-dimethyl-1H-pyrrol-2-yl)prop-2-en-1-one; (E)-1-(4-bromophenyl)-2-(4-bromophenylmethylsulfenyl)-3-(4-hydroxy-3,5-diiodophenyl)prop-2-en-1-one; (E)-1-(4-bromophenyl)-2-(4-chlorophenylmethylsulfenyl)-3-(2,3,5-trichlorophenyl)prop-2-en-1-one; (E)-1-(4-bromophenyl)-2-(4-chlorophenylmethylsulfenyl)-3-(3-hydroxy-4-methoxyphenyl)prop-2-en-1-one; (E)-1-(4-bromophenyl)-2-(4-chlorophenylmethylsulfenyl)-3-(4-bromophenyl)prop-2-en-1-one; (E)-1-(4-bromophenyl)-2-(4-fluorophenylmethylsulfenyl)-3-(2,4,6-trimethoxyphenyl)prop-2-en-1-one; (E)-1-(4-bromophenyl)-2-(4-fluorophenylmethylsulfenyl)-3-(2-benzyloxyphenyl)prop-2-en-1-one; (E)-1-(4-bromophenyl)-2-(4-fluorophenylmethylsulfenyl)-3-(5-chloro-3-indolyl)prop-2-en-1-one; (E)-1-(4-carboxyphenyl)-2-(4-bromophenylmethylsulfenyl)-3-(4-bromo-3-nitrophenyl)prop-2-en-1-one; (E)-1-(4-carboxyphenyl)-2-(4-bromophenylmethylsulfenyl)-3-(4-bromophenyl)prop-2-en-1-one; (E)-1-(4-carboxyphenyl)-2-(4-bromophenylmethylsulfenyl)-3-(4-fluoro-3-nitrophenyl)prop-2-en-1-one; (E)-1-(4-carboxyphenyl)-2-(4-chlorophenylmethylsulfenyl)-3-(4-(N,N-dimethylamino)phenyl)prop-2-en-1-one; (E)-1-(4-chlorophenyl)-2-(2,4-dichlorophenylmethylsulfenyl)-3-(2,3-dichlorophenyl)prop-2-en-1-one; (E)-1-(4-chlorophenyl)-2-(3,4-dichlorophenylmethylsulfenyl)-3-(4-hydroxyphenyl)prop-2-en-1-one; (E)-1-(4-chlorophenyl)-2-(4-chlorophenylmethylsulfenyl)-3-(2-methoxyphenyl)prop-2-en-1-one; (E)-1-(4-chlorophenyl)-2-(4-chlorophenylmethylsulfenyl)-3-(4-bromophenyl)prop-2-en-1-one; (E)-1-(4-chlorophenyl)-2-(4-methylphenylmethylsulfenyl)-3-(2-benzyloxyphenyl)prop-2-en-1-one; (E)-1-(4-chlorophenyl)-2-(4-methylphenylmethylsulfenyl)-3-(2-fluoro-5-nitrophenyl)prop-2-en-1-one; (E)-1-(4-chlorophenyl)-2-(4-methylphenylmethylsulfenyl)-3-(5-bromo-3-indolyl)prop-2-en-1-one; (E)-1-(4-chlorophenyl)-2-(4-methylphenylmethylsulfenyl)-3-(5-chloro-3-indolyl)prop-2-en-1-one; (E)-1-(4-chlorophenyl)-2-(4-methylphenylmethylsulfenyl)-3-(5-chloro-3-indolyl)prop-2-en-1-one; (E)-1-(4-cyanophenyl)-2-(4-bromophenylmethylsulfenyl)-3-(3-hydroxy-4-nitrophenyl)prop-2-en-1-one; (E)-1-(4-nitrophenyl)-2-(4-bromophenylmethylsulfenyl)-3-(3-hydroxy-4-nitrophenyl)prop-2-en-1-one; (E)-1-(4-trifluoromethylphenyl)-2-(4-bromophenylmethylsulfenyl)-3-(3-hydroxy-4-nitrophenyl)prop-2-en-1-one; (E)-1-(2,3,4,5,6-pentafluorophenyl)-2-(4-bromophenylmethylsulfenyl)-3-(3-hydroxy-4-nitrophenyl)prop-2-en-1-one; (E)-1-(2,4-dichlorophenyl)-2-(4-bromophenylmethylsulfenyl)-3-(4-hydroxy-3-nitrophenyl)prop-2-en-1-one; (E)-1-(4-bromophenyl)-2-(4-bromophenylmethylsulfenyl)-3-(3,5-dibromo-4-hydroxyphenyl)prop-2-en-1-one; (E)-1-(4-bromophenyl)-2-(4-bromophenylmethylsulfenyl)-3-(3-hydroxy-4-nitrophenyl)prop-2-en-1-one; (E)-1-(4-bromophenyl)-2-(4-chlorophenylmethylsulfenyl)-3-(2,4,6-trimethoxyphenyl)prop-2-en-1-one; (E)-1-(4-bromophenyl)-2-(4-chlorophenylmethylsulfenyl)-3-(2-methoxyphenyl)prop-2- en-1-one; (E)-1-(4-bromophenyl)-2-(4-chlorophenylmethylsulfenyl)-3-(4-(N,N-dimethylamino)phenyl)prop-2-en-1-one; (E)-1-(4-bromophenyl)-2-(4-chlorophenylmethylsulfenyl)-3-(4-chlorophenyl)prop-2-en-1-one; (E)-1-(4-bromophenyl)-2-(4-chlorophenylmethylsulfenyl)-3-(4-hydroxyphenyl)prop-2-en-1-one; (E)-1-(4-bromophenyl)-2-(4-chlorophenylmethylsulfenyl)-3-(4-methoxyphenyl)prop-2-en-1-one; (E)-1-(4-bromophenyl)-2-(4-fluorophenylmethylsulfenyl)-3-(3,5-dimethylphenyl)prop-2-en-1-one; (E)-1-(4-bromophenyl)-2-(4-methylphenylmethylsulfenyl)-3-(2-fluorophenyl)prop-2-en-1-one; (E)-1-(4-carboxyphenyl)-2-(4-bromophenylmethylsulfenyl)-3-(3-hydroxy-4-nitrophenyl)prop-2-en-1-one; (E)-1-(4-carboxyphenyl)-2-(4-fluorophenylmethylsulfenyl)-3-(3-hydroxy-4-methoxyphenyl)prop-2-en-1-one; (E)-1-(4-chlorophenyl)-2-(2,4-dichlorophenylmethylsulfenyl)-3-(3-ethoxy-4-hydroxyphenyl)prop-2-en-1-one; (E)-1-(4-chlorophenyl)-2-(2,4-dichlorophenylmethylsulfenyl)-3-(4-benzyloxyphenyl)prop-2-en-1-one; (E)-1-(4-chlorophenyl)-2-(2,4-dichlorophenylmethylsulfenyl)-3-(4-chlorophenyl)prop-2-en-1-one; (E)-1-(4-chlorophenyl)-2-(2,4-dichlorophenylmethylsulfenyl)-3-(5-bromo-3-indolyl)prop-2-en-1-one; (E)-1-(4-chlorophenyl)-2-(2-chlorophenylmethylsulfenyl)-3-(2,3,4-trimethoxyphenyl)prop-2-en-1-one; (E)-1-(4-chlorophenyl)-2-(2-chlorophenylmethylsulfenyl)-3-(4-bromophenyl)prop-2-en-1-one; (E)-1-(4-chlorophenyl)-2-(2-chlorophenylmethylsulfenyl)-3-(4-chlorophenyl)prop-2-en-1-one; (E)-1-(4-chlorophenyl)-2-(2-fluorophenylmethylsulfenyl)-3-(2-methoxyphenyl)prop-2-en-1-one; (E)-1-(4-chlorophenyl)-2-(4-chlorophenylmethylsulfenyl)-3-(2,3-dichlorophenyl)prop-2-en-1-one; (E)-1-(4-chlorophenyl)-2-(4-chlorophenylmethylsulfenyl)-3-(4-benzyloxyphenyl)prop-2-en-1-one; (E)-1-(4-chlorophenyl)-2-(4-chlorophenylmethylsulfenyl)-3-(4-hydroxyphenyl)prop-2-en-1-one; (E)-1-(4-chlorophenyl)-2-(4-chlorophenylmethylsulfenyl)-3-(4-methoxyphenyl)prop-2-en-1-one; (E)-1-(4-chlorophenyl)-2-(4-fluorophenylmethylsulfenyl)-3-(2-methoxyphenyl)prop-2-en-1-one; (E)-1-(4-chlorophenyl)-2-(4-fluorophenylmethylsulfenyl)-3-(4-bromophenyl)prop-2-en-1-one; (E)-1-(4-chlorophenyl)-2-(4-fluorophenylmethylsulfenyl)-3-(4-chlorophenyl)prop-2-en-1-one; (E)-1-(4-chlorophenyl)-2-(4-methylphenylmethylsulfenyl)-3-(4-bromophenyl)prop-2-en-1-one; (E)-1-(4-chlorophenyl)-2-(4-methylphenylmethylsulfenyl)-3-(4-chlorophenyl)prop-2-en-1-one; (E)-1-(4-chlorophenyl)-2-(4-methylphenylmethylsulfenyl)-3-(4-hydroxyphenyl)prop-2-en-1-one; (E)-1-(4-nitrophenyl)-2-(4-chlorophenylmethylsulfenyl)-3-(2-methoxyphenyl)prop-2-en-1-one; (E)-1-(4-trifluoromethylphenyl)-2-(4-bromophenylmethylsulfenyl)-3-(4-hydroxy-3-nitrophenyl)prop-2-en-1-one; (E)-1-(2,3,4,5,6-pentafluorophenyl)-2-(4-bromophenylmethylsulfenyl)-3-(4-hydroxy-3-nitrophenyl)prop-2-en-1-one; (E)-1-(2-chlorophenyl)-2-(4-bromophenylmethylsulfenyl)-3-(4-chlorophenyl)prop-2-en-1-one; (E)-1-(4-bromophenyl)-2-(4-bromophenylmethylsulfenyl)-3-(3,5-dichloro-4-hydroxyphenyl)prop-2-en-1-one; (E)-1-(4-bromophenyl)-2-(4-chlorophenylmethylsulfenyl)-3-(2,3-dichlorophenyl)prop-2-en-1-one; (E)-1-(4-bromophenyl)-2-(4-chlorophenylmethylsulfenyl)-3-(4-methoxyphenyl)prop-2-en-1-one; (E)-1-(4-bromophenyl)-2-(4-fluorophenylmethylsulfenyl)-3-(4-(N,N-dimethylamino)phenyl)prop-2-en-1-one; (E)-1-(4-bromophenyl)-2-(4-fluorophenylmethylsulfenyl)-3-(4-bromophenyl)prop-2-en-1-one; (E)-1-(4-bromophenyl)-2-(4-fluorophenylmethylsulfenyl)-3-(4-fluoro-2-trifluoromethylphenyl)prop-2-en-1-one; (E)-1-(4-bromophenyl)-2-(4-fluorophenylmethylsulfenyl)-3-(4-methoxyphenyl)prop-2-en-1-one; (E)-1-(4-chlorophenyl)-2-(2,4-dichlorophenylmethylsulfenyl)-3-(2,4,6-trimethoxyphenyl)prop-2-en-1-one; (E)-1-(4-chlorophenyl)-2-(2,4-dichlorophenylmethylsulfenyl)-3-(3-indolyl)prop-2-en-1-one; (E)-1-(4-chlorophenyl)-2-(2-chlorophenylmethylsulfenyl)-3-(4-hydroxy-3-nitrophenyl)prop-2-en-1-one; (E)-1-(4-chlorophenyl)-2-(3,4-dichlorophenylmethylsulfenyl)-3-(2,4,6-trimethoxyphenyl)prop-2-en-1-one; (E)-1-(4-chlorophenyl)-2-(3,4-dichlorophenylmethylsulfenyl)-3-(2,5-dimethoxyphenyl)prop-2-en-1-one; (E)-1-(4-chlorophenyl)-2-(3,4-dichlorophenylmethylsulfenyl)-3-(2-benzyloxyphenyl)prop-2-en-1-one; (E)-1-(4-chlorophenyl)-2-(3,4-dichlorophenylmethylsulfenyl)-3-(2-methoxyphenyl)prop-2-en-1-one; (E)-1-(4-chlorophenyl)-2-(3,4-dichlorophenylmethylsulfenyl)-3-(4-ethoxy-3-methoxyphenyl)prop-2-en-1-one; (E)-1-(4-chlorophenyl)-2-(4-bromophenylmethylsulfenyl)-3-(3,5-dimethylphenyl)prop-2-en-1-one; (E)-1-(4-chlorophenyl)-2-(4-chlorophenylmethylsulfenyl)-3-(2,5-dimethylphenyl)prop-2-en-1-one; (E)-1-(4-chlorophenyl)-2-(4-chlorophenylmethylsulfenyl)-3-(3,5-dimethylphenyl)prop-2-en-1-one; (E)-1-(4-chlorophenyl)-2-(4-chlorophenylmethylsulfenyl)-3-(4-hydroxy-3-nitrophenyl)prop-2-en-1-one; (E)-1-(4-chlorophenyl)-2-(4-chlorophenylmethylsulfenyl)-3-(4-methanesulfenylphenyl)prop-2-en-1-one; (E)-1-(4-chlorophenyl)-2-(4-fluorophenylmethylsulfenyl)-3-(2,4,6-trimethoxyphenyl)prop-2-en-1-one; (E)-1-(4-chlorophenyl)-2-(4-methylphenylmethylsulfenyl)-3-(2,5-dimethylphenyl)prop-2-en-1-one; (E)-1-(4-chlorophenyl)-2-(4-methylphenylmethylsulfenyl)-3-(2-methoxyphenyl)prop-2-en-1-one; (E)-1-(4-chlorophenyl)-2-(4-methylphenylmethylsulfenyl)-3-(2-pyrrolyl)prop-2-en-1-one; (E)-1-(4-chlorophenyl)-2-(4-methylphenylmethylsulfenyl)-3-(3,5-dichlorophenyl)prop-2-en-1-one; (E)-1-(4-chlorophenyl)-2-(4-methylphenylmethylsulfenyl)-3-(3-methylthiophen-2-yl)prop-2-en-1-one; (E)-1-(4-chlorophenyl)-2-(4-methylphenylmethylsulfenyl)-3-(4-(N,N-dimethylamino)phenyl)prop-2-en-1-one; (E)-1-(4-cyanophenyl)-2-(4-bromophenylmethylsulfenyl)-3-(4-hydroxy-3-nitrophenyl)prop-2-en-1-one; (E)-1-(4-methoxyphenyl)-2-(4-bromophenylmethylsulfenyl)-3-(4-hydroxy-3-nitrophenyl)prop-2-en-1-one; (E)-1-(4-nitrophenyl)-2-(4-bromophenylmethylsulfenyl)-3-(4-hydroxy-3-nitrophenyl)prop-2-en-1-one; (E)-1-(5-chloro-2-hydroxy-phenyl)-2-(4-bromophenylmethylsulfenyl)-3-(3-hydroxy-4-nitrophenyl)prop-2-en-1-one; (E)-1-(2-chlorophenyl)-2-(4-chlorophenylmethylsulfenyl)-3-(4-chlorophenyl)prop-2-en-1-one; (E)-1-(4-bromophenyl)-2-(4-bromophenylmethylsulfenyl)-3-(3-carboxy-4-hydroxyphenyl)prop-2-en-1-one; (E)-1-(4-bromophenyl)-2-(4-fluorophenylmethylsulfenyl)-3-(2,5-dimethylphenyl)prop-2-en-1-one; (E)-1-(4-bromophenyl)-2-(4-fluorophenylmethylsulfenyl)-3-(4-ethoxy-3-methoxyphenyl)prop-2-en-1-one; (E)-1-(4-carboxyphenyl)-2-(4-fluorophenylmethylsulfenyl)-3-(4-(N,N-dimethylamino)phenyl)prop-2-en-1-one; (E)-1-(4-chlorophenyl)-2-(2-chlorophenylmethylsulfenyl)-3-(4- ethoxy-3-methoxyphenyl)prop-2-en-1-one; (E)-1-(4-chlorophenyl)-2-(4-chlorophenylmethylsulfenyl)-3-(2-pyrrolyl)prop-2-en-1-one; (E)-1-(4-chlorophenyl)-2-(4-methylphenylmethylsulfenyl)-3-(4-fluoro-3-methylphenyl) prop-2-en-1-one; (E)-1-(4-chlorophenyl)-2-(4-methylphenylmethylsulfenyl)-3-(4-methanesulfenylphenyl) prop-2-en-1-one; and (E)-1-(5-chloro-2-hydroxy-phenyl)-2-(4-bromophenylmethylsulfenyl)-3-(4-hydroxy-3-nitrophenyl)prop-2-en-1-one; and salts thereof.

Other particular compounds that are embodiments of the invention wherein m is 1 and n is 0 include (E)-1-(4-carboxyphenyl)-2-(2,4-dichlorophenylmethylsulfenyl)-3-(4-bromo-3-nitrophenyl)prop-2-en-1-one; (E)-1-(4-carboxyphenyl)-2-(2,4-dichlorophenylmethylsulfenyl)-3-(4-chloro-3-nitrophenyl)prop-2-en-1-one; (E)-1-(4-carboxyphenyl)-2-(2,4-dichlorophenylmethylsulfenyl)-3-(4-fluoro-3-nitrophenyl)prop-2-en-1-one; (E)-1-(4-carboxyphenyl)-2-(2-chlorophenylmethylsulfenyl)-3-(4-bromo-3-nitrophenyl)prop-2-en-1-one; (E)-1-(4-carboxyphenyl)-2-(2-chlorophenylmethylsulfenyl)-3-(4-fluoro-3-nitrophenyl)prop-2-en-1-one; (E)-1-(4-carboxyphenyl)-2-(2-fluorophenylmethylsulfenyl)-3-(4-chloro-3-nitrophenyl)prop-2-en-1-one; (E)-1-(4-nitrophenyl)-2-(4-bromophenylmethylsulfenyl)-3-(2,4,5-trimethoxyphenyl)prop-2-en-1-one; (E)-1-(4-carboxyphenyl)-2-(4-bromophenylmethylsulfenyl)-3-(2-fluorophenyl)prop-2-en-1-one; (E)-1-(4-bromophenyl)-2-(4-bromophenylmethylsulfenyl)-3-(3-(3-(2,5-dimethyl-3,6-dioxocyclohexa-1,4-dienyl)-3-methylbutanoyloxy)-4-nitrophenyl)prop-2-en-1-one; (E)-1-(4-carboxyphenyl)-2-(4-bromophenylmethylsulfenyl)-3-(4-(4-methylpiperazin-1-yl)-3-nitrophenyl)prop-2-en-1-one; (E)-1-(2,3,4,5,6-pentafluorophenyl)-2-(4-bromophenylmethylsulfenyl)-3-(4-fluoro-3-nitrophenyl)prop-2-en-1-one; (E)-1-(4-(2-(4-methylpiperazin-1-yl)ethylcarbamoyl)phenyl)-2-(4-bromophenylmethylsulfenyl)-3-(4-fluoro-3-nitrophenyl) prop-2-en-1-one; (E)-1-(4-(2-(morpholin-4-yl) ethylcarbamoyl)phenyl)-2-(4-bromophenylmethylsulfenyl)-3-(4-fluoro-3-nitrophenyl)prop-2-en-1-one; (E)-1-(4-(2-(N,N-diethylamino)ethylcarbamoyl)phenyl)-2-(4-bromophenylmethylsulfenyl)-3-(4-fluoro-3-nitrophenyl) prop-2-en-1-one; (E)-1-(4-(3-(4-methylpiperazin-1-yl)propylcarbamoyl)phenyl)-2-(4-bromophenylmethylsulfenyl)-3-(4-fluoro-3-nitrophenyl) prop-2-en-1-one; (E)-1-(4-(4-(5-(trifluoromethyl)pyridin-2-yl)piperazine-1-carbonyl)phenyl)-2-(4-bromophenylmethylsulfenyl)-3-(4-fluoro-3-nitrophenyl) prop-2-en-1-one; (E)-1-(4-[4-(2-hydroxyethyl)piperazine-1-carbonyl]phenyl)-2-(4-bromophenylmethylsulfenyl)-3-(4-fluoro-3-nitrophenyl)prop-2-en-1-one; (E)-1-(4-fluorophenyl)-2-(4-bromophenylmethylsulfenyl)-3-(4-fluoro-3-nitrophenyl)prop-2-en-1-one; (E)-1-(4-bromophenyl)-2-(4-bromophenylmethylsulfenyl)-3-(4-nitrophenyl)prop-2-en-1-one; (E)-1-(4-bromophenyl)-2-(4-chlorophenylmethylsulfenyl)-3-(3-pyridinyl)prop-2-en-1-one; (E)-1-(4-chlorophenyl)-2-(4-chlorophenylmethylsulfenyl)-3-(3-pyridinyl)prop-2-en-1-one; (E)-1-(4-chlorophenyl)-2-(4-chlorophenylmethylsulfenyl)-3-(4-chlorophenyl)prop-2-en-1-one; (E)-1-(4-chlorophenyl)-2-(4-chlorophenylmethylsulfenyl)-3-(4-methoxyphenyl)prop-2-en-1-one; (E)-1-(4-chlorophenyl)-2-(4-chlorophenylmethylsulfenyl)-3-(4-nitrophenyl)prop-2-en-1-one; (E)-1-(4-chlorophenyl)-2-(4-chlorophenylmethylsulfenyl)-3-(4-trifluoromethylphenyl) prop-2-en-1-one; (E)-1-(4-carboxyphenyl)-2-(4-fluorophenylmethylsulfenyl)-3-(3-nitro-4-(4-(phenylmethyl)piperazin-1-yl)phenyl)prop-2-en-1-one; (E)-1-(4-fluorophenyl)-2-(4-fluorophenylmethylsulfenyl)-3-(4-(2-(4-methylpiperazin-1-yl)ethylamino)-3-nitrophenyl) prop-2-en-1-one; (E)-1-(4-fluorophenyl)-2-(4-fluorophenylmethylsulfenyl)-3-(4-(4-(2-hydroxyethyl) piperazin-1-yl)-3-nitrophenyl)prop-2-en-1-one; (E)-1-(4-fluoro-3-nitrophenyl)-2-(4-fluorophenylmethylsulfenyl)-3-(4-[4-(2-hydroxyethyl)piperazine-1-carbonyl]phenyl)prop-2-en-1-one; (E)-1-(4-carboxyphenyl)-2-(4-fluorophenylmethylsulfenyl)-3-(4-acetamido-3-nitrophenyl) prop-2-en-1-one; (E)-1-(4-carboxyphenyl)-2-(4-fluorophenylmethylsulfenyl)-3-(4-amino-3-nitrophenyl) prop-2-en-1-one; (E)-1-(4-((4-fluorophenyl) methylsulfenyl)-3-nitrophenyl)-2-(4-fluorophenylmethylsulfenyl)-3-(4-fluoro-3-nitrophenyl) prop-2-en-1-one; (E)-1-(4-((4-methylphenyl)sulfonyloxy) phenyl)-2-(4-fluorophenylmethylsulfenyl)-3-(4-fluoro-3-nitrophenyl)prop-2-en-1-one; (E)-1-(4-(2-(4-methylpiperazin-1-yl)ethylcarbamoyl)phenyl)-2-(4-fluorophenylmethylsulfenyl)-3-(4-fluoro-3-nitrophenyl) prop-2-en-1-one; (E)-1-(4-(2-(N,N-diethylamino)ethoxy) phenyl)-2-(4-fluorophenylmethylsulfenyl)-3-(4-fluoro-3-nitrophenyl)prop-2-en-1-one; (E)-1-(4-(3-(2,5-dimethyl-3,6-dioxocyclohexa-1,4-dienyl)-3-methylbutanoyloxy) phenyl)-2-(4-fluorophenylmethylsulfenyl)-3-(4-fluoro-3-nitrophenyl)prop-2-en-1-one; (E)-1-(4-(3-(morpholin-4-yl) propoxy)phenyl)-2-(4-fluorophenylmethylsulfenyl)-3-(4-fluoro-3-nitrophenyl)prop-2-en-1-one; (E)-1-(4-fluorophenyl)-2-(4-fluorophenylmethylsulfenyl)-3-(4-fluoro-3-nitrophenyl)prop-2-en-1-one; (E)-1-(4-hydroxyphenyl)-2-(4-fluorophenylmethylsulfenyl)-3-(4-fluoro-3-nitrophenyl)prop-2-en-1-one; (E)-1-(4-sulfamoylphenyl)-2-(4-fluorophenylmethylsulfenyl)-3-(4-fluoro-3-nitrophenyl)prop-2-en-1-one; (E)-1-(phenyl)-2-(4-fluorophenylmethylsulfenyl)-3-(4-fluoro-3-nitrophenyl) prop-2-en-1-one; (E)-1-(4-chlorophenyl)-2-(4-methoxyphenylmethylsulfenyl)-3-(4-fluorophenyl)prop-2-en-1-one; (E)-1-(4-chlorophenyl)-2-(4-methoxyphenylmethylsulfenyl)-3-(4-methoxyphenyl)prop-2-en-1-one; (E)-1-(4-carboxyphenyl)-2-(4-methylphenylmethylsulfenyl)-3-(4-fluoro-3-nitrophenyl) prop-2-en-1-one; (E)-1-(4-carboxyphenyl)-2-(4-methylphenylmethylsulfenyl)-3-(4-fluoro-3-nitrophenyl) prop-2-en-1-one; (E)-1-(4-chloro-3-nitrophenyl)-2-(4-methylphenylmethylsulfenyl)-3-(4-fluoro-3-nitrophenyl) prop-2-en-1-one; (E)-1-(4-carboxyphenyl)-2-(4-trifluoromethylphenylmethylsulfenyl)-3-(4-chloro-3-nitrophenyl)prop-2-en-1-one; (E)-1-(4-carboxyphenyl)-2-(4-trifluoromethylphenylmethylsulfenyl)-3-(4-fluoro-3-nitrophenyl)prop-2-en-1-one; (E)-1-(4-carboxyphenyl)-2-(6-bromo-1H-benzo[d]imidazol-2-ylmethylsulfenyl)-3-(4-fluoro-3-nitrophenyl)prop-2-en-1-one; (E)-1-(4-carboxyphenyl)-2-(phenylmethylsulfenyl)-3-(4-fluoro-3-nitrophenyl)prop-2-en-1-one and (E)-methyl-4-(2-(4-bromobenzylthio)-3-(4-fluoro-3-nitrophenyl)acryloyl) benzoate; and salts thereof.

Particular compounds that are embodiments of the invention wherein m is 1 and n is 1 include (E)-1-(4-chlorophenyl)-2-(2-chlorophenylmethylsulfinyl)-3-(2,4,6-trimethoxyphenyl)prop-2-en-1-one and (E)-1-(4-chlorophenyl)-2-(4-chlorophenylmethylsulfinyl)-3-(4-fluoro-2-trifluoromethylphenyl)prop-2-en-1-one.

Particular compounds that are embodiments of the invention wherein m is 1 and n is 2 include (E)-1-(4-bromophenyl)-2-(4-fluorophenylmethylsulfonyl)-3-(2,5-dimethylphenyl) prop-2-en-1-one; (E)-1-(4-chlorophenyl)-2-(2-chlorophenylmethylsulfonyl)-3-(2-benzyloxyphenyl)prop- 2-en-1-one; (E)-1-(4-chlorophenyl)-2-(3,4-dichlorophenylmethylsulfonyl)-3-(2-methoxyphenyl)prop-2-en-1-one; (E)-1-(4-chlorophenyl)-2-(4-chlorophenylmethylsulfonyl)-3-(3,5-dimethylphenyl)prop-2-en-1-one; (E)-1-(4-chlorophenyl)-2-(4-chlorophenylmethylsulfonyl)-3-(4-benzyloxyphenyl)prop-2-en-1-one; (E)-1-(4-chlorophenyl)-2-(4-chlorophenylmethylsulfonyl)-3-(5-methylthiophen-2-yl)prop-2-en-1-one; (E)-1-(4-chlorophenyl)-2-(4-methylphenylmethylsulfonyl)-3-(2,3-dichlorophenyl)prop-2-en-1-one; (E)-1-(4-chlorophenyl)-2-(4-methylphenylmethylsulfonyl)-3-(2,5-dimethylphenyl)prop-2-en-1-one; (E)-1-(4-chlorophenyl)-2-(4-methylphenylmethylsulfonyl)-3-(2-benzyloxyphenyl)prop-2-en-1-one; (E)-1-(4-methoxyphenyl)-2-(4-bromophenylmethylsulfonyl)-3-(4-bromophenyl)prop-2-en-1-one; (E)-1-(4-nitrophenyl)-2-(4-chlorophenylmethylsulfonyl)-3-(3-methylthiophen-2-yl)prop-2-en-1-one; (E)-1-(4-bromophenyl)-2-(4-bromophenylmethylsulfonyl)-3-(4-hydroxy-3-nitrophenyl)prop-2-en-1-one; (E)-1-(4-bromophenyl)-2-(4-chlorophenylmethylsulfonyl)-3-(2-benzyloxyphenyl)prop-2-en-1-one; (E)-1-(4-bromophenyl)-2-(4-methylphenylmethylsulfonyl)-3-(4-methanesulfonylphenyl)prop-2-en-1-one; (E)-1-(4-chlorophenyl)-2-(4-chlorophenylmethylsulfonyl)-3-(2,3,4-trimethoxyphenyl)prop-2-en-1-one; (E)-1-(4-chlorophenyl)-2-(4-fluorophenylmethylsulfonyl)-3-(3-methylthiophen-2-yl)prop-2-en-1-one; (E)-1-(4-bromophenyl)-2-(4-chlorophenylmethylsulfonyl)-3-(2-hydroxy-4-methoxyphenyl)prop-2-en-1-one; (E)-1-(4-bromophenyl)-2-(4-fluorophenylmethylsulfonyl)-3-(3,5-dimethylphenyl)prop-2-en-1-one; (E)-1-(4-bromophenyl)-2-(4-methylphenylmethylsulfonyl)-3-(4-methanesulfenylphenyl)prop-2-en-1-one; (E)-1-(4-chlorophenyl)-2-(2-chlorophenylmethylsulfonyl)-3-(4-ethoxy-3-methoxyphenyl)prop-2-en-1-one; (E)-1-(4-chlorophenyl)-2-(3,4-dichlorophenylmethylsulfonyl)-3-(4-hydroxyphenyl)prop-2-en-1-one; (E)-1-(4-chlorophenyl)-2-(4-chlorophenylmethylsulfonyl)-3-(2,5-dimethylphenyl)prop-2-en-1-one; (E)-1-(4-chlorophenyl)-2-(4-chlorophenylmethylsulfonyl)-3-(3-ethoxy-4-hydroxyphenyl)prop-2-en-1-one; (E)-1-(4-chlorophenyl)-2-(4-chlorophenylmethylsulfonyl)-3-(4-bromophenyl)prop-2-en-1-one; (E)-1-(4-chlorophenyl)-2-(4-chlorophenylmethylsulfonyl)-3-(4-methanesulfenylphenyl)prop-2-en-1-one; (E)-1-(4-chlorophenyl)-2-(4-fluorophenylmethylsulfonyl)-3-(2,4,6-trimethoxyphenyl)prop-2-en-1-one; (E)-1-(4-chlorophenyl)-2-(4-methylphenylmethylsulfonyl)-3-(2-methoxyphenyl)prop-2-en-1-one; (E)-1-(4-chlorophenyl)-2-(4-methylphenylmethylsulfonyl)-3-(3,5-dimethylphenyl)prop-2-en-1-one; (E)-1-(4-chlorophenyl)-2-(4-methylphenylmethylsulfonyl)-3-(4-ethoxy-3-methoxyphenyl)prop-2-en-1-one; (E)-1-(4-chlorophenyl)-2-(4-methylphenylmethylsulfonyl)-3-(5-bromo-3-indolyl)prop-2-en-1-one; (E)-1-(4-nitrophenyl)-2-(4-chlorophenylmethylsulfonyl)-3-(2,4,6-trimethoxyphenyl)prop-2-en-1-one; (E)-1-(4-nitrophenyl)-2-(4-chlorophenylmethylsulfonyl)-3-(2-methoxyphenyl)prop-2-en-1-one; (E)-1-(4-bromophenyl)-2-(4-chlorophenylmethylsulfonyl)-3-(4-methoxyphenyl)prop-2-en-1-one; (E)-1-(4-bromophenyl)-2-(4-fluorophenylmethylsulfonyl)-3-(4-bromophenyl)prop-2-en-1-one; (E)-1-(4-chlorophenyl)-2-(2,4-dichlorophenylmethylsulfonyl)-3-(5-methylthiophen-2-yl)prop-2-en-1-one; (E)-1-(4-chlorophenyl)-2-(4-methylphenylmethylsulfonyl)-3-(4-bromophenyl)prop-2-en-1-one; (E)-1-(4-chlorophenyl)-2-(4-methylphenylmethylsulfonyl)-3-(4-methanesulfenylphenyl)prop-2-en-1-one; (E)-1-(4-nitrophenyl)-2-(4-chlorophenylmethylsulfonyl)-3-(5-methylthiophen-2-yl)prop-2-en-1-one; (E)-1-(4-bromophenyl)-2-(4-bromophenylmethylsulfonyl)-3-(3,5-dibromo-4-hydroxyphenyl)prop-2-en-1-one; (E)-1-(4-bromophenyl)-2-(4-bromophenylmethylsulfonyl)-3-(3,5-dichloro-4-hydroxyphenyl)prop-2-en-1-one; (E)-1-(4-bromophenyl)-2-(4-chlorophenylmethylsulfonyl)-3-(2,4,6-trimethoxyphenyl)prop-2-en-1-one; (E)-1-(4-carboxyphenyl)-2-(4-bromophenylmethylsulfonyl)-3-(4-chloro-3-nitrophenyl)prop-2-en-1-one; (E)-1-(4-chlorophenyl)-2-(2-chlorophenylmethylsulfonyl)-3-(4-bromophenyl)prop-2-en-1-one; (E)-1-(4-chlorophenyl)-2-(4-chlorophenylmethylsulfonyl)-3-(2-methoxyphenyl)prop-2-en-1-one; (E)-1-(4-chlorophenyl)-2-(4-chlorophenylmethylsulfonyl)-3-(3-methylthiophen-2-yl)prop-2-en-1-one; (E)-1-(4-chlorophenyl)-2-(4-chlorophenylmethylsulfonyl)-3-(4-hydroxy-3-nitrophenyl)prop-2-en-1-one; (E)-1-(4-chlorophenyl)-2-(4-chlorophenylmethylsulfonyl)-3-(biphenyl-4-yl)prop-2-en-1-one; (E)-1-(4-chlorophenyl)-2-(4-methylphenylmethylsulfonyl)-3-(3-methylthiophen-2-yl)prop-2-en-1-one; (E)-1-(4-chlorophenyl)-2-(4-methylphenylmethylsulfonyl)-3-(4-chlorophenyl)prop-2-en-1-one; (E)-1-(4-chlorophenyl)-2-(4-methylphenylmethylsulfonyl)-3-(5-methylthiophen-2-yl)prop-2-en-1-one; and (E)-1-(4-iodophenyl)-2-(4-iodophenylmethylsulfonyl)-3-(4-bromophenyl)prop-2-en-1-one; and salts thereof.

It is to be understood that other particular and preferred embodiments of the compounds of the invention will combine the features of the particular and preferred embodiments of the invention explicitly described above. Embodiments defined by such combinations are contemplated as particular embodiments of the invention.

In other preferred embodiments the compound of formula I, or any of the embodiments thereof, is an isolated compound. In other preferred embodiments, the compound of formula I, and compositions containing the compound, including pharmaceutical compositions, are substantially free of pharmaceutically unacceptable contaminants. A pharmaceutically unacceptable contaminant is a substance which, if present in more than an insubstantial amount, would render the compound or composition unsuitable for use as a pharmaceutical for therapeutic administration. Examples include toxic materials such as halogenated solvents and heavy metals, and potentially infectious materials such as bacteria, fungi, viruses, and bacterial and fungal spores.

III. Methods for Preparing Compounds of the Invention and Intermediates Useful in the Synthesis of Compounds of the Invention There are provided processes for preparing compounds according to formula I, intermediates that are useful in the preparation of such compounds, and processes for preparing such intermediates.

In the text, formulae and schemes that follow, unless otherwise indicated $Ar^1$, $Ar^2$, $Ar^3$, m, and n are as defined above for formula I.

Compounds according to formula I may be prepared by a process comprising condensing a compound of formula II with an aromatic aldehyde of formula III.

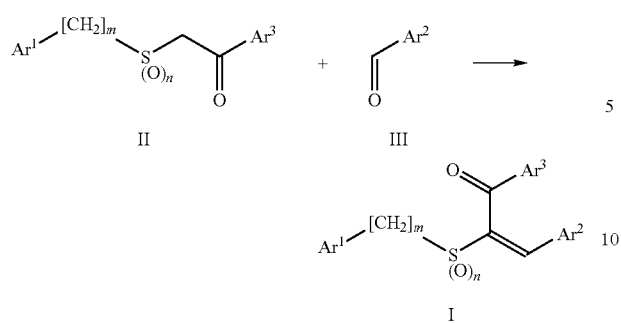

The condensation may be achieved by treatment with acid or base catalysts or reagents. The reaction is preferably carried out in an appropriate solvent. The reactions are typically carried out at a temperature between 0° C. and the reflux temperature of the solvent, which is typically about 100° C. Depending on the substrates, heating the reaction mixture, and/or removal of water may be beneficial. For example, particularly when n is 2, a preferred method of carrying out the reaction is by heating in toluene in the presence of catalytic amounts of piperidine and a carboxylic acid with removal of water using a Dean Stark trap.

Compounds according to formula I may be prepared by a process comprising the oxidation of other compounds of formula I, and intermediate compounds of formula II may be prepared by a process comprising the oxidation of other compounds of formula II.

Compounds according to formula I wherein n is 2 may be prepared by a process comprising oxidizing a corresponding compound of formula I wherein n is 0 or 1.

Compounds according to formula I wherein n is 1 may be prepared by a process comprising oxidizing a corresponding compound of formula I wherein n is 0.

Compounds according to formula II wherein n is 1 may be prepared by a process comprising oxidizing a corresponding compound of formula II wherein n is 0.

Compounds according to formula II wherein n is 2 may be prepared by a process comprising oxidizing a corresponding compound of formula II wherein n is 0 or 1.

Compounds according to formula II wherein n is 1 may be prepared by a process comprising oxidizing a corresponding compound of formula II wherein n is 0.

The aforementioned oxidation processes are carried out by reacting the starting material with an appropriate oxidizing agent in a suitable solvent at an appropriate temperature. Suitable solvents for such oxidation processes typically include alcohols, for example methanol or ethanol, carboxylic acids, for example acetic acid, or chlorinated solvents, for example dichloromethane or chloroform. Suitable oxidizing agents typically include hydrogen peroxide, carboxylic peracids, such as m-chloroperoxybenzoic acid, or persulfate salts, such as potassium peroxymonosulfate. In the case of inorganic oxidizing agents such as potassium peroxymonosulfate, hydroxylic solvents such as alcohols are preferred, and the solvent typically contains water in an amount sufficient to cause the oxidizing agent to remain in solution. The reactions are typically carried out at a temperature between 0° C. and the reflux temperature of the solvent, which is typically about 100° C. The person skilled in the art will know how to select suitable oxidizing agents and reaction conditions. For example, under mild conditions such as low temperature and using a limiting amount of oxidizing agent, selective oxidation of thioethers to sulfoxides can often be achieved, whereas under more forcing conditions such as using excess oxidizing agent, higher temperature, or prolonged reaction times oxidation of thioethers or sulfoxides to sulfones can be achieved. Certain reagents (e.g. sodium periodate) are known to oxidize thioethers selectively to sulfoxides.

Compounds according to formula II wherein n is 0 may be prepared by a process comprising coupling a mercaptan of formula IV with a compound of formula V, wherein X is leaving group.

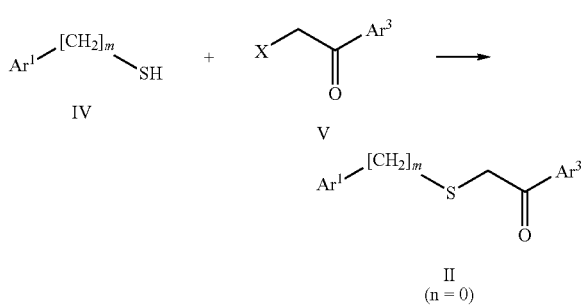

Compounds according to formula II wherein m is 1 and n is 0, may be prepared by a process comprising coupling a compound of formula VI, wherein X is leaving group, with a mercaptan of formula VII, wherein X is leaving group.

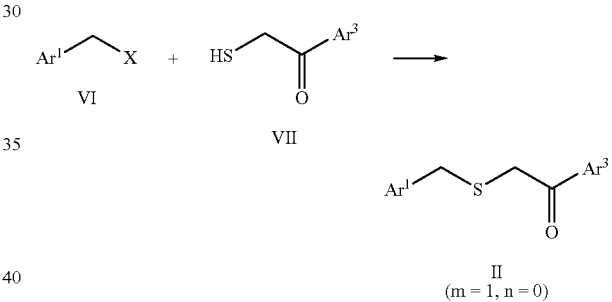

Suitable leaving groups X in the compounds of formula V and VII include halogen, particularly chlorine, bromine, and iodine, and sulfonate groups, particularly methanesulfonate, p-toluenesulfonate, and trifluoromethanesulfonate. The coupling reactions are typically performed using a basic catalyst or reagent in a suitable solvent at a suitable temperature. Suitable bases include alkali metal hydroxide or alkoxide salts such as sodium hydroxide or methoxide, and tertiary amines such as triethylamine or N,N-diisopropylethylamine. Suitable solvents include alcohols, such as methanol, or chlorinated solvents such as dichloromethane. The reactions are typically carried out at a temperature between 0° C. and the reflux temperature of the solvent, which is typically about 100° C. For example, in a typical procedure, the reactions would be conducted by treatment of the mercaptan with a solution of sodium hydroxide in methanol followed by addition of the compound V or VII. The reaction is preferably carried out in an anaerobic environment to minimize the oxidation of the thiolate anion.

Compounds of formula III are either commercially available, known in the literature, or may be prepared by methods known to one skilled in the art. Methods used for the formation of aromatic aldehydes include, for example, formylation of aromatic compounds, including electrophilic formylation, organometallically-catalyzed formylation using carbon monoxide, or lithiation followed by reaction with an N,N-dialkylformamide and hydrolysis. See, e.g., the reactions referenced for the formation of aldehydes in *Advanced Organic Chemistry*, by Jerry March (3$^{rd}$ Edition, John Wiley & Sons, 1985), p. 1147-1148.

Mercaptans of formula IV are either commercially available, known in the literature, or may be prepared by methods known to one skilled in the art. For example, mercaptans can be produced by the reduction of sulfonic acid or sulfonyl chlorides, which, in the case of aromatic sulfonyl halides (m=0), can be produced by electrophilic sulfonation or chlorosulfonation of aromatic rings. Other methods include nucleophilic substitution of compounds with a suitable leaving group such as halides (i.e. compounds of formula VI) with a suitable divalent sulfur compound. The reaction is typically performed with compounds such as thiolacetic acid or thiourea, which perform the substitution to give initially a protected intermediate (such as a thiolacetate, or thiouronium salt) which can be subsequently converted to the mercaptan, for example by hydrolysis. The nucleophilic substitution is in general particularly facile with benzylic-type compounds where the substitution occurs at a position alpha to an aromatic ring (i.e. with compounds VI where m is 1). See, e.g., the reactions referenced for the formation of mercaptans in *Advanced Organic Chemistry*, by Jerry March (3$^{rd}$ Edition, John Wiley & Sons, 1985), p. 1168; *The Chemistry of the Thiol Group*, by S. Patai, Ed. (Wiley-Interscience, New York, 1974).

Mercaptans of formula VII are likewise commercially available, known in the literature, or may be prepared by methods known to one skilled in the art. For example, the mercaptans of formula VII can be prepared from compounds of formula V by nucleophilic substitution of the leaving group X with thiolacetic acid or thiourea followed by hydrolysis of the resulting protected intermediate.

Compounds of formula V are commercially available, known in the literature, or may be prepared by methods known to one skilled in the art. For example, the compounds of formula V may be prepared by halogenation, for example bromination, of a ketone of formula VIII. The reaction may be performed by reaction of the ketone of formula VIII with the elemental halogen or N-haloimide, most preferably an N-halosuccinimide. The preferred halogen is bromine, and the preferred halogenating agents are elemental bromine, and N-bromosuccinimide. In order to limit the halogenation to monohalogenation, it is preferable to perform the reaction under neutral or acidic conditions. The reaction is preferably carried out at a temperature in the range from about –20° C. to about 80° C., preferably about –10° C. to about 35° C., most preferably at about 0° C. to about 5° C. Preferred solvents for conducting the reaction include halogenated solvents, for example chloroform or dichloromethane, carboxylic acids, for example acetic acid. In particular cases it may be advantageous for the halogenation to be performed upon a derivative of the ketone such as an enolate, enol ether, enol silane, or enol ester.

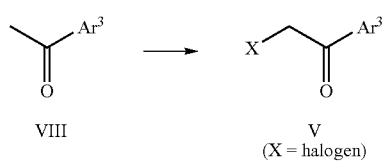

Compounds of formula VI are likewise commercially available, known in the literature, or may be prepared by methods known to one skilled in the art. For example, —CH$_2$— groups alpha to an aromatic ring can be readily halogenated under free radical conditions. Alternatively, appropriate X groups could be introduced by conversion of the corresponding alcohol (by conversion of OH to halogen, or treatment with a sulfonyl chloride such as p-toluenesulfonyl chloride), which can be prepared by a variety of methods, for example via formylation of an aromatic ring followed by reduction, as illustrated in the scheme below:

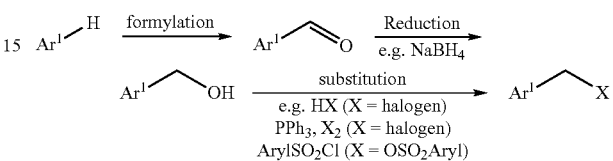

Acyl aromatic compounds of formula VIII are also commercially available, known in the literature, or may be prepared by methods known to one skilled in the art. Classically such compounds are available via Friedel Crafts acylation of the aromatic ring starting from an arene compound of formula IX. The reaction is typically formed by reacting the arene compound of formula IX with acetyl chloride in the presence of a Lewis acid catalyst, for example aluminium trichloride.

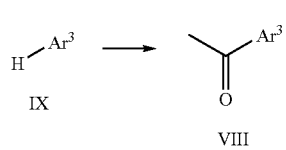

Acylation of the Ar$^3$ aromatic ring can also be performed by reaction of an organometallic Ar$^3$-metal species with an appropriate acylating agent. Such reactions may be performed by treating Ar$^3$—H with a strong base such as an alkyllithium or a lithium amide base (such as lithium diethylamide, lithium diisopropylamide, or lithium hexamethyldisilazide). Such an approach is feasible where the Ar$^3$—H bond is sufficiently acidic, either due to the electronic properties of the Ar$^3$ ring, or the presence of a group "ortho" to the Ar$^3$—H bond to direct metallation to the site of interest. Alternatively metallation may be performed by converting an Ar$^3$-Halogen bond (such as Ar$^3$—Br) to the Ar$^3$-metal species, for example by treatment with an alkyllithium (such as t-butyllithium) or magnesium metal (Grignard agent formation). Once the Ar$^3$-metal species is formed, acylation can be performed by quenching with a suitable acyl cation equivalent, for example acetic anhydride, ethyl acetate, or acetonitrile. These methods, however, are only illustrative of the wide variety of methods for the synthesis of aryl methyl ketones.

In the compounds described above, some functional groups on the aromatic rings, in particular aromatic amine nitrogens, are further derivatizeable. Derivatives of aromatic amino groups which are useful in the present invention include, for example: acylation to form carboxamide, carbamate, and urea derivatives; sulfonylation to form sulfonamides, sulfonyl ureas, and sulfamoyl esters; imine formation for formation of imines and for alkylation or arylation (or heteroarylation) via reductive animation; alkylation to form mono- or di-alkylamino derivatives, palladium catalyzed cross coupling to form N-aryl (or N-heteroaryl) derivatives by coupling with aromatic halides or aromatic pseudo halides such as aromatic triflates. Derivatives may also include conjugates to biological molecules such as antibodies to yield macro molecules capable of being directed to a desired site of action thereby reducing or precluding side effects associated with interaction of a drug prepared from a compound of the present invention with tissues and cells which are not proliferating abnormally.

The above-described reactions, unless otherwise noted, are usually conducted at a pressure of about one to about three atmospheres, preferably at ambient pressure (about one atmosphere).

The present invention further embraces isolated compounds according to formula I. The expression "isolated compound" refers to a preparation of a compound of formula I, or a mixture of compounds according to formula I, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula I or a mixture of compounds according to formula I, which contains the named compound or mixture of compounds according to formula I in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC. The preferred method for purification of the compounds according to formula I or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Preferred solvents for crystallization include water, alcohols, particularly alcohols containing up to four carbon atoms such as methanol, ethanol, isopropanol, and butan-1-ol, butan-2-ol, and 2-methyl-2-propanol, ethers, for example diethyl ether, diisopropyl ether, t-butyl methyl ether, 1,2-dimethoxyethane, tetrahydrofuran and 1,4-dioxane, carboxylic acids, for example formic acid and acetic acid, and hydrocarbon solvents, for example pentane, hexane, toluene, and mixtures thereof, particularly aqueous mixtures such as aqueous ethanol. Pure solvents, preferably at least analytical grade, and more preferably pharmaceutical grade are preferably used. In a preferred embodiment of the processes of the invention, the products are so isolated. In the compounds of the invention according to formula I or salt thereof, and pharmaceutical compositions thereof, the compound according to formula I or salt thereof is preferably in or prepared from a crystalline form, preferably prepared according to such a process.

The synthetic methods described above reflect a convergent synthesis strategy. Thus the $Ar^1$ and $Ar^2$ components may be synthesized and elaborated separately prior to coupling the two components to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the coupling reactions described.

It will be appreciated by one skilled in the art that certain aromatic substituents in the compounds of the invention, intermediates used in the processes described above, or precursors thereto, may be introduced by employing aromatic substitution reactions to introduce or replace a substituent, or by using functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected". Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts, John Wiley & Sons Ltd., the entire disclosure of which is incorporated herein by reference.

In addition to use of a protecting group, sensitive functional groups may be introduced as synthetic precursors to the functional group desired in the intermediate or final product. An example of this is an aromatic nitro ($—NO_2$) group. The aromatic nitro group goes not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, 2$^{nd}$ Edition, 2004), *Comprehensive Heterocyclic Chemistry*, Ed. A. R. Katritzky and C. W. Rees (Pergamon Press, 1984), and *Comprehensive Heterocyclic Chemistry II*, Ed. A. R. Katritzky, C. W. Rees, and E. F. V. Scriven (Pergamon Press, 1996).

IV. Antibody Conjugates

Another aspect of the invention relates to antibody conjugates of compounds of formula I of the formula I-L-Ab, or a salt thereof, wherein I is a compound of formula I; Ab is an antibody; and -L- is a single bond or a linking group covalently linking said compound of formula I to said antibody.

In a preferred sub-embodiment of the aforesaid conjugates of the formula I-L-Ab, said antibody (Ab) is a monoclonal antibody or a monospecific polyclonal antibody.

In a more preferred sub-embodiment of the aforesaid conjugates of the formulae I-L-Ab, the aforesaid antibody (Ab) is a tumor-specific antibody.

Antibodies, preferably monoclonal antibodies and monospecific polyclonal antibodies, and most preferably tumor-specific antibodies, may be covalently linked to compounds of the present invention. A "tumor-specific antibody" is an antibody which specifically binds to a tumor antigen, e.g., an antigen on a tumor cell.

The covalent linker between a compound of formula I and an antibody may, in its simplest form, comprise a single covalent bond connecting the compound of formula I to the antibody. More commonly the compound of formula I is attached to the antibody using a suitable bifunctional linking reagent. The term "bifunctional linking reagent" refers generally to a molecule that comprises two reactive moieties which are connected by a spacer element. The term "reactive moieties", in this context, refers to chemical functional groups capable of coupling with an antibody or a compound of formula I by reacting with functional groups on the antibody and the compound of formula I.

An example of a covalent bond formed as a linker between a compound of formula I and an antibody is a disulfide bond formed by the oxidation of an antibody and a compound of formula I, wherein a linking group is used that contains one or more cysteine amino acids. The cysteine residues can be oxidized to form disulfide links by dissolving 1 mg of the a suitable compound of formula I and 0.5 equivalents of the desired antibody in 1.5 ml of 0.1% (v/v) 17.5 mM acetic acid, pH 8.4, followed by flushing with nitrogen and then 0.01 M K$_2$Fe(CN)$_6$. After incubation for one hour at room temperature, the adduct peptide is purified by HPLC.

Another example of a suitable covalent bond formed as a linker between a compound of formula I and an antibody is an amide bond formed by reacting an amino group on a compound of the invention with a carboxylic acid group which forms part of the primary structure of the antibody (Ab) (such as, for example a glutamic or aspartic amino acid residue). Alternately, an amide bond could be formed if the reacting moieties were reversed, i.e., the compound of formula I could contain a carboxylic acid functionality and react with an amino functionality within the Ab structure.

Alternatively, a compound of formula I and an antibody Ab may be covalently linked using a bifunctional linking reagent.

For example, adducts can be prepared by first preparing S—(—N-hexylsuccinimido)-modified derivatives of an antibody and of a compound of formula I, according to the method of Cheronis et al., *J. Med. Chem.* 37: 348 (1994) (the entire disclosure of which is incorporated herein by reference). N-hexylmaleimide, a precursor for the modified antibody and compound of formula I, is prepared from N-(methoxycarbonyl)maleimide and N-hexylamine by mixing the two compounds in saturated NaHCO$_3$ at 0° C. according to the procedure of Bodanszky and Bodanszky, *The Practice of Peptide Synthesis*; Springer-Verlag, New York, pp. 29-31 (1984) (the entire disclosure of which is incorporated herein by reference). The product of the resulting reaction mixture is isolated by extraction into ethyl acetate, followed by washing with water, dried over Na$_2$SO$_4$, and is then concentrated in vacuo to produce N-hexylmaleimide as a light yellow oil. S—(N-Hexylsuccinimido)-modified antibody and formula I compound are then prepared from a cysteine-containing peptide and N-hexylmaleimide by mixing one part peptide with 1.5 parts N-hexylmaleimide in N,N-dimethylformamide (3.3 mL/mM peptide) followed by addition to 30 volumes of 0.1 M ammonium bicarbonate, pH 7.5. The S-alkylation reaction carried out in this manner is complete in 30 minutes. The resulting S—(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is attached to the formula I compound) may be prepared according to the method of Cheronis et al., supra from cysteine-substituted peptides. A mixture of one part bismaleimidohexane is made with two parts peptide monomer in N,N-dimethylformamide (3.3 mL/mM peptide) followed by addition to 0.1 ammonium bicarbonate, pH 7.5. The reaction mixture is stirred at room temperature and is usually completed within 30 minutes. The resulting bis-succinimidohexane peptide dimer is purified by preparative reverse-phase HPLC. After lyophilization the material is a fluffy, white powder.

Covalently linked adducts of the general formula I-L-Ab of the present invention may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH").

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For hetero-bifunctional linking, a compound of formula I is derivatized with, for example, the N-hydroxysuccinimidyl portion of the bifunctional reagent, and the resulting derivatized compound is purified by chromatography. Next, a suitable tumor-specific Mab is reacted with the second functional group of the bifunctional linking reagent, assuring a directed sequence of binding between components of the desired adduct.

Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the Mab or the formula I compound are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include, for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either a Mab or to a formula I compound wherein with an attached peptidyl group, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyridyldithio)-propionate (SPDP), 2-iminothiolane (2-IT), 3-(4-carboxamidophenyldithio)propionthioimidate (CDPT), N-succinimidyl-acetylthioacetate (SATA), ethyl-S-acetyl-propionthioimidate (AMPT) and N-succinimidyl-3-(4-carboxamidophenyldithio)propionate (SCDP). Procedures for preparation of immunoconjugates using these linkers is detailed in Cattel, et al, "Toxin-Targeted Design for Anticancer Therapy II: Preparation and Biological Comparison of Different Chemically Linked Gelonin-Antibody Conjugates", *J. Pharm. Sci.*, 1993, 82, 699-704, the entire disclosure of which is incorporated herein by reference.

V. Treatment of Cellular Proliferative Disorders Using Compounds of the Invention According to another embodiment of the invention, a method of treating an individual suffering from a cellular proliferative disorder, particularly cancer, is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of treating an individual suffering from a cellular proliferative disorder, particularly cancer, is provided, comprising administering to said individual an effective amount of at least one conjugate of the formula I-L-Ab, either alone, or in combination with a pharmaceutically acceptable carrier.

The invention is also directed to the use in medicine of a compound according to formula I, or a pharmaceutically acceptable salt thereof, or a conjugate according to formula I-L-Ab, or a pharmaceutically acceptable salt thereof.

The invention is also directed to the use of a compound according to formula I, or a pharmaceutically acceptable salt thereof, or a conjugate according to formula I-L-Ab, or a pharmaceutically acceptable salt thereof, in the preparation of a medicament for treatment of a cellular proliferative disorder, particularly cancer, or for inducing apoptosis of tumor cells in an individual affected with cancer.

Particular and preferred embodiments of this aspect of the invention are those wherein the compound of formula I used in the method of treatment, either alone or as part of a composition, or as a component of the antibody conjugate, is a particular or preferred embodiment of the compound of formula I in the description of the compounds and compositions of the invention as provided herein.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

VI. Salts of Compounds According to the Invention

The compounds of the present invention may take the form of salts. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VII. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VIII. Routes of Administration of Compounds and Compositions of the Invention The compounds may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

IX. Isomerism in Compounds of the Invention

A. Geometrical Isomerism

The compounds of the invention possess an olefinic double bond. The stereochemistry of compounds possessing an olefinic double bond is designated using the nomenclature using E and Z designations. The compounds are named according to the Cahn-Ingold-Prelog system, described in the IUPAC 1974 Recommendations, Section E: Stereochemistry, in *Nomenclature of Organic Chemistry*, John Wiley & Sons, Inc., New York, N.Y., 4$^{th}$ ed., 1992, pp. 127-38, the entire contents of which is incorporated herein by reference. Using this system of nomenclature, the four groups about a double bond are prioritized according to a series of rules wherein various functional groups are ranked. The isomer with the two higher ranking groups on the same side of the double bond is designated Z and the other isomer, in which the two higher ranking groups are on opposite sides of the double bond, is designated E. This is illustrated schematically in Scheme 1, where the Cahn-Ingold-Prelog system priority of the double bond substituents A is greater than that of B, and the priority of A' is greater than that of B'. The configuration of the S—C=C—Ar² bond in the compounds of the invention is designated as E under this system of nomenclature.

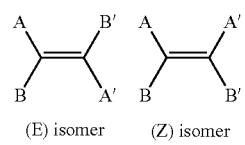

Scheme 1

(E) isomer    (Z) isomer

B. Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention which are biologically active in the treatment of cancer or other proliferative disease states.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 2, the Cahn-Ingold-Prelog ranking is A>B>C>D. The lowest ranking atom, D is oriented away from the viewer.

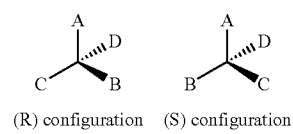

Scheme 2

(R) configuration    (S) configuration

Chiral centers in the compounds of the invention may occur, for example in the substituents attached to the aryl or heteroaryl groups Ar¹, Ar², Ar³, and/or Ar⁴. In addition, compounds wherein n is 1 (sulfoxides) are chiral, having two possible configurations at the sulfur atom, as shown in Scheme 3.

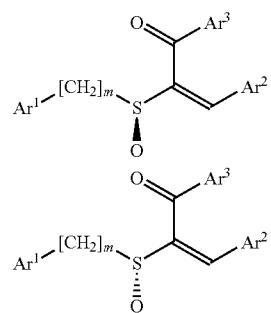

Scheme 3

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

C. Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (Scheme 4). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula I which are biologically active in the treatment of cancer or other proliferative disease states.

Scheme 4

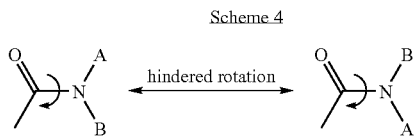

D. Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below (Scheme 5).

Scheme 5

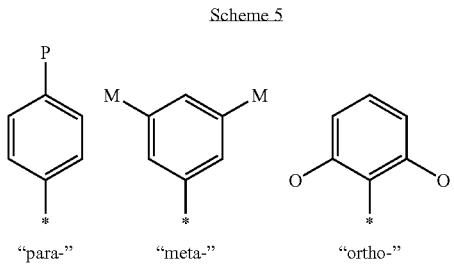

Examples

The following non-limiting examples are provided to illustrate the invention. In the synthetic pathways and methods that follow, reference to the term "aryl" is intended to include substituted and unsubstituted aryl, and also substituted and unsubstituted heteroaryl. The illustrated synthetic pathways are applicable to other embodiments of the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallisation from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and Advanced Practical Organic Chemistry, by J. Leonard, et al. ($2^{nd}$ Edition, CRC Press 1994).

Synthesis Examples

Synthesis Example 1

General Method for the Synthesis of (E)-1-aryl-2-arylthio-3-arylprop-2-en-1-ones

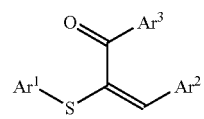

A. Synthesis of 2-Bromo-1-arylethanone

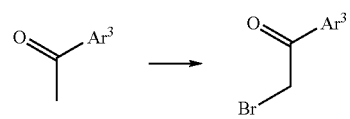

Bromine (1 eq.) or N-bromosuccinamide (1 eq.) in 10 mL of chloroform is added dropwise to a solution of a 1-arylethanone (acetophenone) (1 eq.) in chloroform (40 mL) stirred at 0° C. After the addition is completed, the solution is stirred for a further 2 hours and chloroform is then removed under vacuum to produce, typically, a quantitative yield of the 2-bromo-1-arylethanone.

B. Synthesis of 1-Aryl-2-arylthioethanone

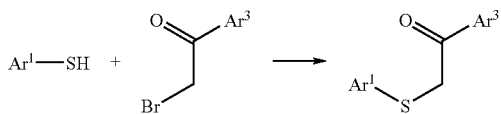

An aryl thiol (1 eq.) is added to a solution of a 2-bromo-1-arylethanone (1 eq.) in ethanol (20 mL), and the reaction mixture is heated under reflux for 6 to 8 hours. The product which separates on cooling is filtered off and washed several times with water to remove sodium bromide. The product is then recrystallized from an appropriate solvent to yield a pure 1-aryl-2-arylthioethanone.

C. Synthesis of (E)-1-aryl-2-arylthio-3-arylprop-2-en-1-ones

Two alternative methods for the synthesis of (E)-1-aryl-2-arylthio-3-arylprop-2-en-1-ones are described in detail below.

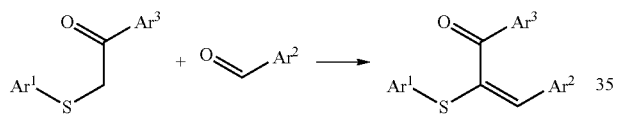

Method A:

A solution of a 1-aryl-2-arylthioethanone (1 eq.) in acetic acid (10 mL) is mixed with an aryl aldehyde (1 eq.) and benzylamine (0.5 mL) and heated under reflux for 3 to 5 hours. The solution is allowed to cool and ether is added. The ethereal solution is washed successively with dilute hydrochloric acid, aqueous 10% sodium hydroxide, saturated sodium hydrogensulfate and water, then dried (MgSO$_4$) and filtered. Evaporation of the dried ethereal layer typically produces a solid. Recrystallization or column chromatographic purification of the solid gives the pure (E)-1-aryl-2-arylthio-3-aryl-prop-2-en-1-one.

Method B:

A solution of a 1-aryl-2-arylthioethanone (1 eq.) in toluene (10 mL) is mixed with an aryl aldehyde (1 eq.), piperidine (0.13 eq.), and benzoic acid (0.15 eq.) is heated under reflux for 3 to 5 hours using a Dean-Stark apparatus. The solution is allowed to cool and toluene is removed under vacuum in a rotavapor. The resulting solid is taken in ether and the ethereal solution was washed successively with aqueous 10% sodium hydroxide, saturated sodium hydrogensulfate and water, then dried (MgSO$_4$), and filtered. Evaporation of the dried ethereal layer typically produces a solid. Recrystallization or column chromatographic purification of the solid gives the pure (E)-1-aryl-2-arylthio-3-aryl-prop-2-en-1-one.

Synthesis Example 2

Synthesis of (E)-1-(4-bromophenyl)-2-(4-bromophenylthio)-3-(2,4,6-trimethoxyphenyl)-prop-2-en-1-one

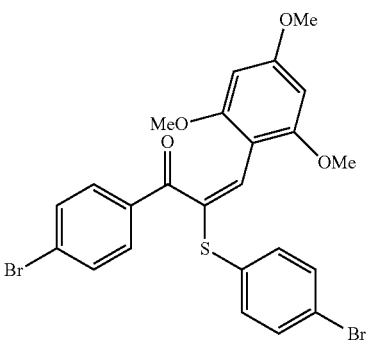 [SMILES: COc1cc(OC)c(/C=C(/Sc2ccc(Br)cc2)C(=O)c2ccc(Br)cc2)c(OC)c1]

The title compound is prepared by the methods described in Synthesis Example 1. A solution of 1-(4-bromophenyl)-2-(4-bromophenylthio)ethanone (10 mmol) and 2,4,6-trimethoxybenzaldehyde (10 mmol) was subjected to the procedure described as Method B in part C of Synthesis Example 1 and the product obtained was purified by column chromatography. m.p 130-132° C.

Synthesis Example 3

Synthesis of (E)-1-(4-bromophenyl)-2-(4-bromophenylthio)-3-(4-Iodophenyl)-prop-2-en-1-one

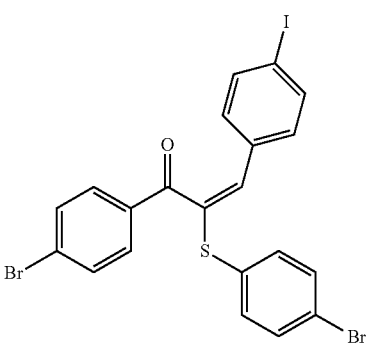 [SMILES: O=C(/C(=C\c1ccc(I)cc1)Sc1ccc(Br)cc1)c1ccc(Br)cc1]

The title compound is prepared by the methods described in Synthesis Example 1. A solution of 1-(4-bromophenyl)-2-(4-bromophenylthio)ethanone (10 mmol) and 4-iodobenzaldehyde (10 mmol) was subjected to the procedure described as Method B in part C of Synthesis Example 1 and the product obtained was purified by column chromatography. m.p. 128-130° C.

Synthesis Example 4

Synthesis of (E)-1-(2-Bromophenyl)-2-(4-bromophenylthio)-3-(4-bromophenyl)-prop-2-en-1-one

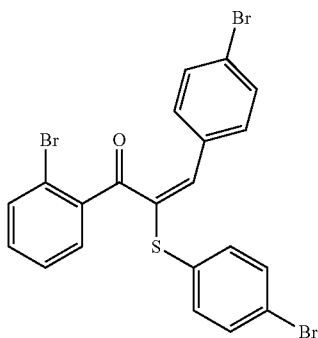 [SMILES: O=C(/C(=C\c1ccc(Br)cc1)Sc1ccc(Br)cc1)c1ccccc1Br]

The title compound is prepared by the methods described in Synthesis Example 1. A solution of 1-(2-bromophenyl)-2-(4-bromophenylthio)ethanone (10 mmol) and 4-bromobenzaldehyde (10 mmol) was subjected to the procedure described as Method B in part C of Synthesis Example 1 and the product obtained was purified by column chromatography.

Synthesis Example 5

Synthesis of (E)-1-(4-Bromophenyl)-2-(4-bromophenylthio)-3-(2,4-dichlorophenyl)-prop-2-en-1-one

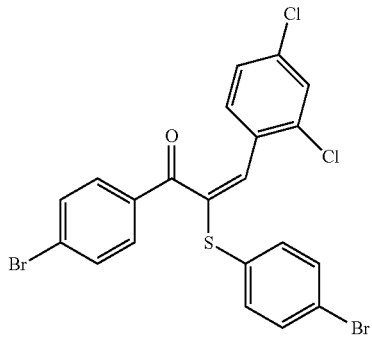 [SMILES: O=C(/C(=C\c1ccc(Cl)cc1Cl)Sc1ccc(Br)cc1)c1ccc(Br)cc1]

The title compound is prepared by the methods described in Synthesis Example 1. A solution of 1-(4-bromophenyl)-2-(4-bromophenylthio)ethanone (10 mmol) and 2,4-dichlorobenzaldehyde (10 mmol) was subjected to the procedure described as Method B in part C of Synthesis Example 1 and the product obtained was purified by column chromatography.

Synthesis Example 6

Synthesis of (E)-1-(4-methoxyphenyl)-2-(4-bromophenylthio)-3-(4-bromophenyl)prop-2-en-1-one

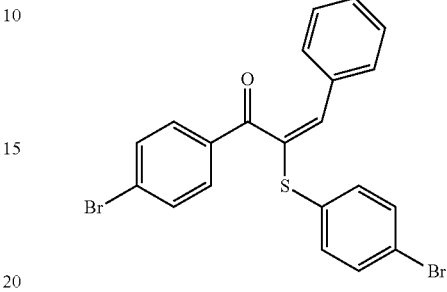

The title compound is prepared by the methods described in Synthesis Example 1. A solution of 1-(4-methoxyphenyl)-2-(4-bromophenylthio)ethanone (10 mmol) and 4-bromobenzaldehyde (10 mmol) was subjected to the procedure described as Method B in part C of Synthesis Example 1 and the product obtained was purified by column chromatography.

Synthesis Example 7

General Method for the Synthesis of (E)-1-aryl-2-arylsulfinyl-3-arylprop-2-en-1-ones

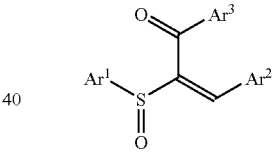

A. Synthesis of 1-aryl-2-arylsulfinylethanone

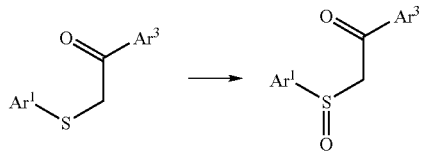

To a vigorously stirred solution of sodium hydroxide (76 mmol) in deionized water (150 mL) is added 1-aryl-2-arylthioethanone (4) (58 mmol). The resulting suspension is stirred for 10 min at room temperature. Sodium bicarbonate (467 mmol) and acetone (49 mL) are added and the solution is cooled to 1° C. A solution of potassium peroxymonosulfate triple salt (2KHSO$_5$.KHSO$_4$.K$_2$SO$_4$) (OXONE®) (38 mmol in 123 mL of EDTA) is added over 10 min keeping the reaction below 5° C. The suspension is stirred for 5 min and immediately quenched at 2° C. with aqueous sodium bisulfite (14.7 g in 30 mL water). Ethyl acetate (75 mL) is added and the solution is acidified with 6N hydrochloric acid (88 mL).

The layers are separated and sodium chloride (73.6 g) is added to the aqueous phase which is then re-extracted with ethyl acetate (75 mL). The organic layers are combined, then washed with deionized water (50 mL) and brine (50 mL), dried over anhydrous magnesium sulfate, filtered and concentrated on a rotary evaporator. The 1-aryl-2-arylsulfinyl-ethanone is typically isolated as a solid after evaporation of the solvent and is dried under vacuum.

B. Synthesis of (E)-1-aryl-2-arylsulfinyl-3-arylprop-2-en-1-ones

Two alternative methods for the synthesis of (E)-1-aryl-2-arylsulfinyl-3-arylprop-2-en-1-ones are described in detail below.

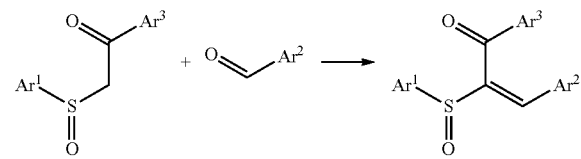

Method A:

A solution of a 1-aryl-2-arylsulfinylethanone (1 eq.) in acetic acid (10 mL) is mixed with an aryl aldehyde (1 eq.) and benzylamine (0.5 mL) and heated under reflux for 3 to 5 hours. The solution is allowed to cool and ether is added. The ethereal solution is washed successively with dilute hydrochloric acid, aqueous 10% sodium hydroxide, saturated sodium hydrogensulfate and water, then dried ($MgSO_4$) and filtered. Evaporation of the dried ethereal layer typically produces a solid. Recrystallization or column chromatographic purification of the solid gives the pure (E)-1-aryl-2-arylsulfinyl-3-aryl-prop-2-en-1-one.

Method B:

A solution of a 1-aryl-2-arylsulfinylethanone (1 eq.) in toluene (10 mL) is mixed with an aryl aldehyde (1 eq.), piperidine (0.13 eq.), and benzoic acid (0.15 eq.) is heated under reflux for 3 to 5 hours using a Dean-Stark apparatus. The solution is allowed to cool and toluene is removed under vacuum in a rotavapor. The resulting solid is taken in ether and the ethereal solution was washed successively with aqueous 10% sodium hydroxide, saturated sodium hydrogensulfate and water, then dried ($MgSO_4$), and filtered. Evaporation of the dried ethereal layer typically produces a solid. Recrystallization or column chromatographic purification of the solid gives the pure (E)-1-aryl-2-arylsulfinyl-3-aryl-prop-2-en-1-one.

Synthesis Example 8

General Method for the Synthesis of (E)-1-aryl-2-arylmethanethio-3-arylprop-2-en-1-ones

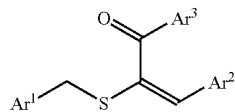

A. Synthesis of 1-aryl-2-arylmethanethioethanones

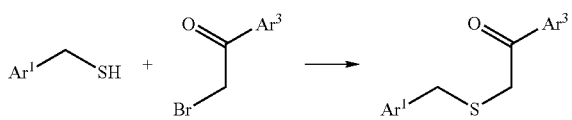

An arylmethane thiol (1 eq.) is added to a solution of a 2-bromo-1-arylethanone (1 eq.) in ethanol (20 mL), and the reaction mixture is heated under reflux for 6 to 8 hours. The product which separates on cooling is filtered off and washed several times with water to remove sodium bromide. The product is then recrystallized from an appropriate solvent to yield a pure 1-aryl-2-arylmethanethioethanone.

B. Synthesis of (E)-1-aryl-2-arylmethanethio-3-arylprop-2-en-1-ones

Two alternative methods for the synthesis of (E)-1-aryl-2-arylmethanethio-3-arylprop-2-en-1-ones are described in detail below.

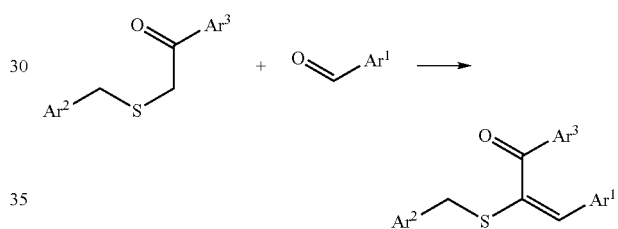

Method A:

A solution of a 1-aryl-2-arylmethanethioethanone (1 eq.) in acetic acid (10 mL) is mixed with an aryl aldehyde (1 eq.) and benzylamine (0.5 mL) and heated under reflux for 3 to 5 hours. The solution is allowed to cool and ether is added. The ethereal solution is washed successively with dilute hydrochloric acid, aqueous 10% sodium hydroxide, saturated sodium hydrogensulfate and water, then dried ($MgSO_4$) and filtered. Evaporation of the dried ethereal layer typically produces a solid. Recrystallization or column chromatographic purification of the solid gives the pure (E)-1-aryl-2-arylmethanethio-3-aryl-prop-2-en-1-one.

Method B:

A solution of a 1-aryl-2-arylmethanethioethanone (1 eq.) in toluene (10 mL) is mixed with an aryl aldehyde (1 eq.), piperidine (0.13 eq.), and benzoic acid (0.15 eq.) is heated under reflux for 3 to 5 hours using a Dean-Stark apparatus. The solution is allowed to cool and toluene is removed under vacuum in a rotavapor. The resulting solid is taken in ether and the ethereal solution was washed successively with aqueous 10% sodium hydroxide, saturated sodium hydrogensulfate and water, then dried ($MgSO_4$), and filtered. Evaporation of the dried ethereal layer typically produces a solid. Recrystallization or column chromatographic purification of the solid gives the pure (E)-1-aryl-2-arylmethanethio-3-aryl-prop-2-en-1-one.

Synthesis Example 9

General Method for the Synthesis of (E)-1-aryl-2-arylmethanesulfinyl-3-arylprop-2-en-1-ones

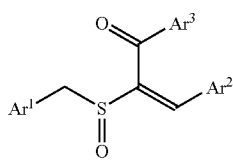

A. Oxidation of 1-aryl-2-arylmethanethioethanones

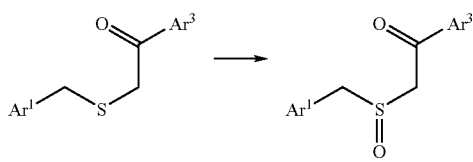

To a vigorously stirred solution of sodium hydroxide (76 mmol) in deionized water (150 mL) is added 1-aryl-2-arylmethanethioethanone (4) (58 mmol). The resulting suspension is stirred for 10 min at room temperature. Sodium bicarbonate (467 mmol) and acetone (49 mL) are added and the solution is cooled to 1° C. A solution of potassium peroxymonosulfate triple salt ($2KHSO_5 \cdot KHSO_4 \cdot K_2SO_4$) (OXONE®) (38 mmol in 123 mL of EDTA) is added over 10 min keeping the reaction below 5° C. The suspension is stirred for 5 min and immediately quenched at 2° C. with aqueous sodium bisulfite (14.7 g in 30 mL water). Ethyl acetate (75 mL) is added and the solution is acidified with 6N hydrochloric acid (88 mL). The layers are separated and sodium chloride (73.6 g) is added to the aqueous phase which is then re-extracted with ethyl acetate (75 mL). The organic layers are combined, then washed with deionized water (50 mL) and brine (50 mL), dried over anhydrous magnesium sulfate, filtered and concentrated on a rotary evaporator. The 1-aryl-2-arylmethanesulfinyl-ethanone is typically isolated as a solid after evaporation of the solvent and is dried under vacuum.

B. Synthesis of (E)-1-aryl-2-arylmethanesulfinyl-3-arylprop-2-en-1-ones

Two alternative methods are available for the synthesis of (E)-1-aryl-2-arylmethanesulfinyl-3-arylprop-2-en-1-ones, as described in detail below.

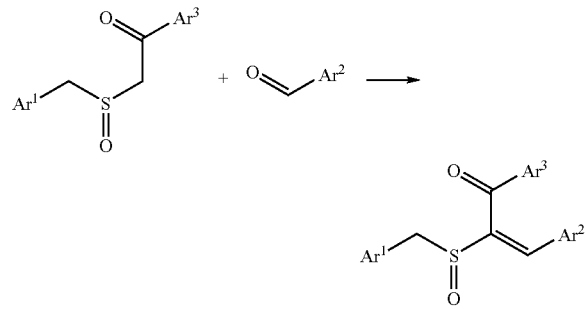

Method A:

A solution of a 1-aryl-2-arylmethanesulfinylethanone (1 eq.) in acetic acid (10 mL) is mixed with an aryl aldehyde (1 eq.) and benzylamine (0.5 mL) and heated under reflux for 3 to 5 hours. The solution is allowed to cool and ether is added. The ethereal solution is washed successively with dilute hydrochloric acid, aqueous 10% sodium hydroxide, saturated sodium hydrogensulfate and water, then dried ($MgSO_4$) and filtered. Evaporation of the dried ethereal layer typically produces a solid. Recrystallization or column chromatographic purification of the solid gives the pure (E)-1-aryl-2-arylmethanesulfinyl-3-aryl-prop-2-en-1-one.

Method B:

A solution of a 1-aryl-2-arylmethanesulfinylethanone (1 eq.) in toluene (10 mL) is mixed with an aryl aldehyde (1 eq.), piperidine (0.13 eq.), and benzoic acid (0.15 eq.) is heated under reflux for 3 to 5 hours using a Dean-Stark apparatus. The solution is allowed to cool and toluene is removed under vacuum in a rotavapor. The resulting solid is taken in ether and the ethereal solution was washed successively with aqueous 10% sodium hydroxide, saturated sodium hydrogensulfate and water, then dried ($MgSO_4$), and filtered. Evaporation of the dried ethereal layer typically produces a solid. Recrystallization or column chromatographic purification of the solid gives the pure (E)-1-aryl-2-arylmethanesulfinyl-3-aryl-prop-2-en-1-one.

Synthesis Example 10

General method for the synthesis of (E)-1-aryl-2-arylmethanesulfonyl-3-arylprop-2-en-1-ones

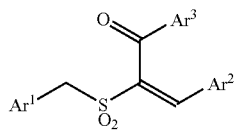

A. Oxidation of 1-aryl-2-arylmethanethioethanones

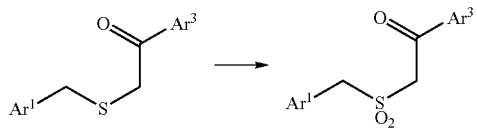

Hydrogen peroxide (30%, 2 mL) was added slowly to a solution of 1-aryl-2-arylmethanethioethanone (1 g) in glacial acetic acid (5 mL) at 0° C. After the addition is complete, the solution is heated under reflux for 1 hour, cooled and poured on to crushed ice (200 g). Typically, a solid separates and is then collected by filtration, then washed and recrystallized from an appropriate solvent to give the pure 1-aryl-2-arylmethanesulfonyl-ethanone.

B. Synthesis of (E)-1-aryl-2-arylmethanesulfonyl-3-arylprop-2-en-1-ones

Two alternative methods for the synthesis of (E)-1-aryl-2-arylmethanesulfonyl-3-arylprop-2-en-1-ones are described in detail below.

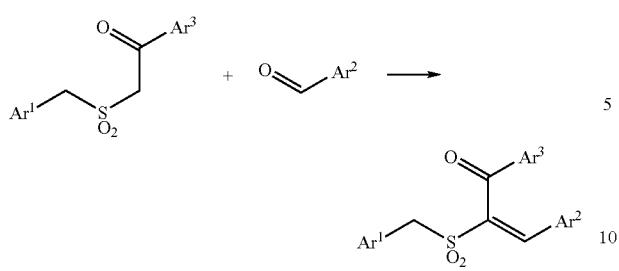

Method A:

A solution of a 1-aryl-2-arylmethanesulfonylethanone (1 eq.) in acetic acid (10 mL) is mixed with an aryl aldehyde (1 eq.) and benzylamine (0.5 mL) and heated under reflux for 3 to 5 hours. The solution is allowed to cool and ether is added. The ethereal solution is washed successively with dilute hydrochloric acid, aqueous 10% sodium hydroxide, saturated sodium hydrogensulfate and water, then dried (MgSO$_4$) and filtered. Evaporation of the dried ethereal layer typically produces a solid. Recrystallization or column chromatographic purification of the solid gives the pure (E)-1-aryl-2-aryl-methanesulfonyl-3-aryl-prop-2-en-1-one.

Method B:

A solution of a 1-aryl-2-arylmethanesulfonylethanone (1 eq.) in toluene (10 mL) is mixed with an aryl aldehyde (1 eq.), piperidine (0.13 eq.), and benzoic acid (0.15 eq.) is heated under reflux for 3 to 5 hours using a Dean-Stark apparatus. The solution is allowed to cool and toluene is removed under vacuum in a rotavapor. The resulting solid is taken in ether and the ethereal solution was washed successively with aqueous 10% sodium hydroxide, saturated sodium hydrogensulfate and water, then dried (MgSO$_4$), and filtered. Evaporation of the dried ethereal layer typically produces a solid. Recrystallization or column chromatographic purification of the solid gives the pure (E)-1-aryl-2-arylmethanesulfonyl-3-aryl-prop-2-en-1-one.

Synthesis Example 11

Synthesis of (E)-1-(4-methoxyphenyl)-2-(4-methoxybenzylsulfonyl)-3-(2,4,6-trimethoxyphenyl)-prop-2-en-1-one

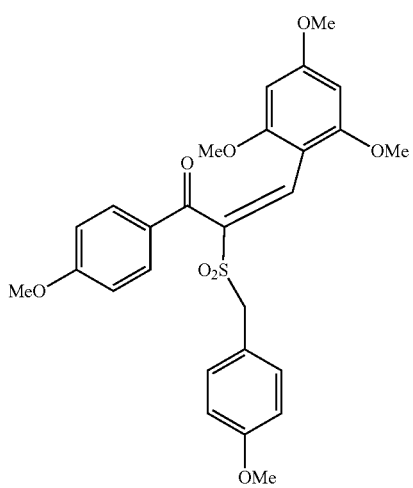 [SMILES: COc1ccc(CS(=O)(=O)/C(=C/c2c(OC)cc(OC)cc2OC)C(=O)c2ccc(OC)cc2)cc1]

The title compound is prepared by the methods described in Synthesis Example 10. A solution of 1-(4-methoxyphenyl)-2-(4-methoxybenzylsulfonyl)ethanone (10 mmol) and 2,4,6-trimethoxybenzaldehyde (10 mmol) was subjected to the procedure described as Method A in part C of Synthesis Example 10 and the product obtained was purified by column chromatography. m.p. 60-62° C.

Synthesis Example 12

Synthesis of (E)-1-(4-bromophenyl)-2-(4-methoxybenzylsulfonyl)-3-(4-bromophenyl)-prop-2-en-1-one

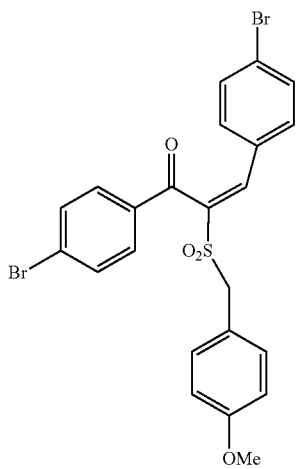 [SMILES: COc1ccc(CS(=O)(=O)/C(=C/c2ccc(Br)cc2)C(=O)c2ccc(Br)cc2)cc1]

The title compound is prepared by the methods described in Synthesis Example 10. A solution of 1-(4-bromophenyl)-2-(4-methoxybenzylsulfonyl)ethanone (10 mmol) and 4-bromobenzaldehyde (10 mmol) was subjected to the procedure described as Method A in part C of Synthesis Example 10 and the product obtained was purified by column chromatography. m.p. 146-150° C.

Synthesis Example 13

Synthesis of (E)-1-(4-iodophenyl)-2-(4-iodobenzylsulfonyl)-3-(4-iodophenyl)-prop-2-en-1-one

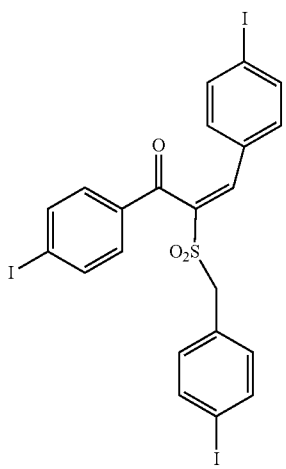 [SMILES: O=C(/C(=C\c1ccc(I)cc1)S(=O)(=O)Cc1ccc(I)cc1)c1ccc(I)cc1]

The title compound is prepared by the methods described in Synthesis Example 10. A solution of 1-(4-iodophenyl)-2-(4-iodobenzylsulfonyl)ethanone (10 mmol) and 4-iodobenzaldehyde (10 mmol) was subjected to the procedure described as Method A in part C of Synthesis Example 10 and the product obtained was purified by column chromatography.

Synthesis Example 14

Synthesis of (E)-1-(4-bromophenyl)-2-(4-iodobenzylsulfonyl)-3-(4-iodophenyl)-prop-2-en-1-one

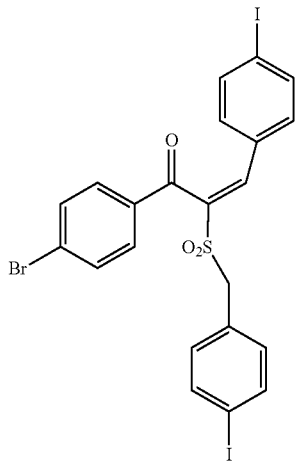 [SMILES: O=C(/C(=C\c1ccc(I)cc1)S(=O)(=O)Cc1ccc(I)cc1)c1ccc(Br)cc1]

The title compound is prepared by the methods described in Synthesis Example 10. A solution of 1-(4-iodophenyl)-2-(4-iodobenzylsulfonyl)ethanone (10 mmol) and 4-bromobenzaldehyde (10 mmol) was subjected to the procedure described as Method A in part C of Synthesis Example 10 and the product obtained was purified by column chromatography.

Synthesis Example 15

Synthesis of (E)-1-(4-Iodophenyl)-2-(4-iodobenzylsulfonyl)-3-(4-bromophenyl)prop-2-en-1-one

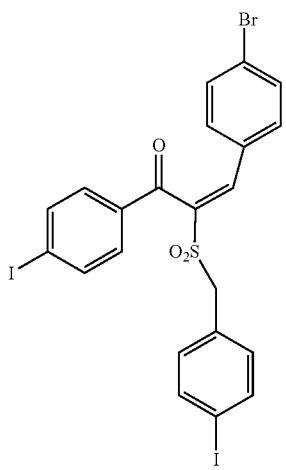 [SMILES: O=C(/C(=C\c1ccc(Br)cc1)S(=O)(=O)Cc1ccc(I)cc1)c1ccc(I)cc1]

The title compound is prepared by the methods described in Synthesis Example 10. A solution of 1-(4-iodophenyl)-2-(4-iodobenzylsulfonyl)ethanone (10 mmol) and 4-bromobenzaldehyde (10 mmol) was subjected to the procedure described as Method A in in part C of Synthesis Example 10 and the product obtained was purified by column chromatography.

Biology Example

Biology Example. Determining the Effect of the Compounds of the Invention on Tumor Cell Lines The effect of the compounds of the invention on tumor cells was determined by the assay described by Latham et al., *Oncogene* 12:827-837 (1996). Tumor cells K562 (chronic myelogenous leukaemia) or DU145 (prostate cancer) were plated in 12-well dishes at a cell density of $2.5 \times 10^4$ cells well. The plated cells were treated 24 hours later with a compound of the invention dissolved in DMSO at multiple concentrations ranging from 1 μM to 100 μM. The plates were examined 96 hours later under an inverted microscope, Olympus CK-2 using an 10× objective, and compound activity was noted by physical observation. When necessary, the total number of viable cells was determined by trypsinizing the wells and counting the number of viable cells, as determined by trypan blue exclusion, using a hemacytometer.

Compound Examples

The representative compounds listed in Tables 1-5 are shown by way of illustration, and are not intended to limit the scope of the invention. The compounds are prepared and tested by methods based on those described above, except that the compound of Table 5 was dissolved in DMSO at multiple concentrations ranging from 0.1 μM to 100 μM

TABLE 1

Compound Examples

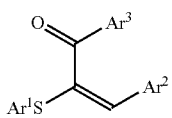

| Example | $Ar^1$ | $Ar^2$ | $Ar^3$ | m.p. (° C.) | K 562 | DU 145 |
|---|---|---|---|---|---|---|
| 1 | 2,3,4,5,6-pentafluorophenyl | 3-hydroxy-4-nitrophenyl | 4-bromophenyl | N/D | ++++ | +++ |
| 2 | 2,3,4,5,6-pentafluorophenyl | 4-hydroxy-3-nitrophenyl | 4-bromophenyl | N/D | +++ | +++ |
| 3 | 2-bromophenyl | 2,3,5-trichlorophenyl | 4-chlorophenyl | 101-107 | + | ++ |
| 4 | 2-bromophenyl | 2,4,6-trihydroxyphenyl | 4-bromophenyl | 101-108 | − | − |

TABLE 1-continued

Compound Examples $$\text{Ar}^1\text{S}-\underset{\text{Ar}^2}{\underset{|}{\text{C}}}=\text{C}-\overset{\text{O}}{\underset{|}{\text{C}}}-\text{Ar}^3$$

| Example | Ar¹ | Ar² | Ar³ | m.p. (° C.) | K 562 | DU 145 |
|---|---|---|---|---|---|---|
| 5 | 2-bromophenyl | 2,4,6-trihydroxyphenyl | 4-chlorophenyl | 92-102 | − | − |
| 6 | 2-bromophenyl | 2,4-dihydroxyphenyl | 4-bromophenyl | 99-107 | + | + |
| 7 | 2-bromophenyl | 2,4-dihydroxyphenyl | 4-chlorophenyl | 102-113 | + | + |
| 8 | 2-bromophenyl | 2-hydroxyphenyl | 4-bromophenyl | 95-105 | + | + |
| 9 | 2-bromophenyl | 4-bromophenyl | 4-bromophenyl | N/D | ++++ | ++++ |
| 10 | 2-bromophenyl | 4-hydroxy-3-nitrophenyl | 4-bromophenyl | N/D | +++ | ++++ |
| 11 | 2-bromophenyl | 4-hydroxy-3-nitrophenyl | 4-chlorophenyl | 113-121 | +++ | ++ |
| 12 | 2-bromophenyl | 4-N,N-dimethylaminophenyl | 4-bromophenyl | 136-145 | − | − |
| 13 | 4-bromophenyl | 2,4,6-trihydroxyphenyl | 4-chlorophenyl | 117-129 | + | ++ |
| 14 | 4-bromophenyl | 2,4,6-trimethoxyphenyl | 4-chlorophenyl | 138-142 | + | + |
| 15 | 4-bromophenyl | 2,4-dichlorophenyl | 4-bromophenyl | N/D | ++++ | ++++ |
| 16 | 4-bromophenyl | 2,4-dihydroxyphenyl | 4-chlorophenyl | 111-128 | ++ | + |
| 17 | 4-bromophenyl | 2,4-difluorophenyl | 4-bromophenyl | N/D | ++++ | ++++ |
| 18 | 4-bromophenyl | 2,4-difluorophenyl | 4-chlorophenyl | 100-108 | ++++ | ++++ |
| 19 | 4-bromophenyl | 2,5-dimethylphenyl | 4-chlorophenyl | 102-109 | +++ | +++ |
| 20 | 4-bromophenyl | 2-amino-3,5-dibromophenyl | 4-bromophenyl | N/D | − | − |
| 21 | 4-bromophenyl | 2-benzyloxyphenyl | 4-chlorophenyl | 116-124 | +++ | +++ |
| 22 | 4-bromophenyl | 2-chloro-4-fluorophenyl | 4-chlorophenyl | N/D | ++++ | ++++ |
| 23 | 4-bromophenyl | 2-fluoro-4-methoxyphenyl | 4-bromophenyl | N/D | ++++ | +++ |
| 24 | 4-bromophenyl | 2-fluorophenyl | 4-chlorophenyl | 100-108 | ++++ | +++ |
| 25 | 4-bromophenyl | 2-methoxyphenyl | 4-chlorophenyl | 105-111 | +++ | +++ |
| 26 | 4-bromophenyl | 3,5-dimethylphenyl | 4-chlorophenyl | 97-107 | ++++ | +++ |
| 27 | 4-bromophenyl | 3-bromo-4-hydroxyphenyl | 2,3,4,5,6-pentafluorophenyl | N/D | ++++ | ++++ |
| 28 | 4-bromophenyl | 3-carboxy-4-hydroxyphenyl | 2,3,4,5,6-pentafluorophenyl | N/D | ++ | ++ |
| 29 | 4-bromophenyl | 3-hydroxy-4-methoxyphenyl | 4-chlorophenyl | 125-129 | N/D | N/D |
| 30 | 4-bromophenyl | 3-hydroxy-4-nitrophenyl | 2,3,4,5,6-pentafluorophenyl | N/D | ++++ | ++++ |
| 31 | 4-bromophenyl | 3-indolyl | 4-bromophenyl | N/D | ++++ | ++++ |
| 32 | 4-bromophenyl | 4-bromo-3-hydroxyphenyl | 4-bromophenyl | N/D | ++++ | ++++ |
| 33 | 4-bromophenyl | 4-bromo-3-hydroxyphenyl | 4-bromophenyl | N/D | + | + |
| 34 | 4-bromophenyl | 4-bromo-3-nitrophenyl | 4-bromophenyl | N/D | ++++ | ++++ |
| 35 | 4-bromophenyl | 4-bromophenyl | 4-bromophenyl | 130-132 | ++++ | ++++ |
| 36 | 4-bromophenyl | 4-bromophenyl | 4-chlorophenyl | N/D | ++++ | ++++ |
| 37 | 4-bromophenyl | 4-chloro-3-nitrophenyl | 4-bromophenyl | N/D | ++++ | ++++ |
| 38 | 4-bromophenyl | 4-chlorophenyl | 4-bromophenyl | N/D | ++++ | ++++ |
| 39 | 4-bromophenyl | 4-fluoro-3-methoxyphenyl | 4-bromophenyl | N/D | ++++ | ++++ |
| 40 | 4-bromophenyl | 4-fluorophenyl | 4-bromophenyl | N/D | ++++ | +++ |
| 41 | 4-bromophenyl | 4-hydroxy-3-methoxyphenyl | 4-bromophenyl | N/D | ++++ | ++++ |
| 42 | 4-bromophenyl | 4-hydroxy-3-nitrophenyl | 2,3,4,5,6-pentafluorophenyl | N/D | ++++ | ++++ |
| 43 | 4-bromophenyl | 4-hydroxy-3-nitrophenyl | 4-bromophenyl | N/D | ++++ | ++++ |
| 44 | 4-bromophenyl | 4-hydroxy-3-nitrophenyl | 4-bromophenyl | N/D | ++ | ++ |
| 45 | 4-bromophenyl | 4-iodophenyl | 4-bromophenyl | 128-130 | ++++ | ++++ |
| 46 | 4-bromophenyl | 4-methanesulfenylphenyl | 4-chlorophenyl | 85-90 | ++++ | ++++ |
| 47 | 4-bromophenyl | 4-methoxyphenyl | 4-bromophenyl | N/D | ++++ | ++ |
| 48 | 4-bromophenyl | 4-methoxyphenyl | 4-chlorophenyl | 139-143 | ++++ | + |
| 49 | 4-bromophenyl | 4-N,N-dimehylaminophenyl | 4-chlorophenyl | 135-148 | − | − |
| 50 | 4-bromophenyl | 4-phenoxyphenyl | 4-chlorophenyl | 123-126 | + | + |
| 51 | 4-bromophenyl | 4-trifluoromethoxyphenyl | 4-bromophenyl | N/D | ++++ | ++++ |
| 52 | 4-bromophenyl | 5-methoxy-3-indolyl | 4-bromophenyl | N/D | ++++ | ++++ |
| 53 | 4-chlorophenyl | 4-chlorophenyl | 4-chlorophenyl | N/D | ++++ | ++++ |
| 54 | 4-fluorophenyl | 2,4,6-trimethoxyphenyl | 4-methoxyphenyl | N/D | + | + |
| 55 | 4-fluorophenyl | 2-benzyloxyphenyl | 4-chlorophenyl | 92-98 | ++++ | ++++ |
| 56 | 4-fluorophenyl | 3-hydroxy-4-methoxyphenyl | 4-methoxyphenyl | N/D | ++++ | +++ |
| 57 | 4-fluorophenyl | 4-bromophenyl | 4-methoxyphenyl | N/D | − | − |
| 58 | 4-fluorophenyl | 4-chlorophenyl | 4-methoxyphenyl | N/D | − | − |
| 59 | 4-fluorophenyl | 4-methoxyphenyl | 4-methoxyphenyl | N/D | ++++ | ++ |
| 60 | 4-fluorophenyl | 5-methylthiophen-2-yl | 4-chlorophenyl | 134-139 | ++ | ++ |
| 61 | 4-methoxyphenyl | 2,4-dichlorophenyl | 4-bromophenyl | N/D | ++++ | ++++ |
| 62 | 4-methoxyphenyl | 2-benzyloxyphenyl | 4-chlorophenyl | 89-92 | ++++ | ++++ |
| 63 | 4-methoxyphenyl | 4-bromophenyl | 4-chlorophenyl | N/D | ++++ | ++ |
| 64 | 4-methoxyphenyl | 5-methylthiophen-2-yl | 4-chlorophenyl | 89-96 | + | + |
| 65 | 4-methylphenyl | 2,3,4,5,6-pentafluorophenyl | 4-chlorophenyl | 84-93 | ++ | ++ |
| 66 | 4-methylphenyl | 2,3,5-trichlorophenyl | 4-chlorophenyl | 103-105 | N/D | N/D |
| 67 | 4-methylphenyl | 2,4,6-trihydroxyphenyl | 4-bromophenyl | 114-116 | + | − |
| 68 | 4-methylphenyl | 2,4,6-trihydroxyphenyl | 4-chlorophenyl | 106-110 | − | − |
| 69 | 4-methylphenyl | 2,4,6-trimethoxyphenyl | 4-chlorophenyl | 123-129 | N/D | N/D |
| 70 | 4-methylphenyl | 2,4,6-trimethoxyphenyl | 4-chlorophenyl | 115-123 | ++ | − |
| 71 | 4-methylphenyl | 2,4-dichlorophenyl | 4-chlorophenyl | 153-156 | ++ | +++ |
| 72 | 4-methylphenyl | 2,4-dichlorophenyl | 4-chlorophenyl | 146-152 | N/D | N/D |
| 73 | 4-methylphenyl | 2,4-difluorophenyl | 4-bromophenyl | 111-123 | − | − |
| 74 | 4-methylphenyl | 2-fluoro-5-nitrophenyl | 4-chlorophenyl | 158-164 | ++++ | +++ |

TABLE 1-continued

Compound Examples $$\underset{Ar^1S}{\overset{O}{\underset{}{\bigvee}}}\underset{Ar^2}{\overset{Ar^3}{}}$$

| Example | Ar¹ | Ar² | Ar³ | m.p. (° C.) | K 562 | DU 145 |
|---|---|---|---|---|---|---|
| 75 | 4-methylphenyl | 2-methoxyphenyl | 4-chlorophenyl | 133-138 | +++ | ++ |
| 76 | 4-methylphenyl | 2-pyrrolyl | 4-chlorophenyl | 122-124 | +++ | +++ |
| 77 | 4-methylphenyl | 3,4-dichlorophenyl | 4-bromophenyl | 112-115 | + | + |
| 78 | 4-methylphenyl | 3,5-dimethylphenyl | 4-chlorophenyl | 117-123 | ++ | + |
| 79 | 4-methylphenyl | 3-hydroxy-4-methoxyphenyl | 4-chlorophenyl | 132-138 | ++++ | ++++ |
| 80 | 4-methylphenyl | 3-indolyl | 4-bromophenyl | 160-164 | +++ | +++ |
| 81 | 4-methylphenyl | 3-indolyl | 4-chlorophenyl | 160-165 | ++++ | +++ |
| 82 | 4-methylphenyl | 3-methylthiophen-2-yl | 4-bromophenyl | 118-121 | + | − |
| 83 | 4-methylphenyl | 3-methylthiophen-2-yl | 4-bromophenyl | 98-101 | + | + |
| 84 | 4-methylphenyl | 3-methylthiophen-2-yl | 4-chlorophenyl | 108-112 | + | + |
| 85 | 4-methylphenyl | 3-quinolinyl | 4-chlorophenyl | 102-106 | − | − |
| 86 | 4-methylphenyl | 4-acetoxyphenyl | 4-chlorophenyl | 93-97 | ++++ | +++ |
| 87 | 4-methylphenyl | 4-acetylphenyl | 4-bromophenyl | 110-117 | + | + |
| 88 | 4-methylphenyl | 4-bromophenyl | 4-chlorophenyl | 130-139 | + | ++ |
| 89 | 4-methylphenyl | 4-bromophenyl | 4-chlorophenyl | 107-111 | N/D | N/D |
| 90 | 4-methylphenyl | 4-chlorophenyl | 4-bromophenyl | 108-112 | ++++ | +++ |
| 91 | 4-methylphenyl | 4-chlorophenyl | 4-chlorophenyl | 103-110 | ++++ | ++ |
| 92 | 4-methylphenyl | 4-ethoxy-3-methoxyphenyl | 4-bromophenyl | 114-121 | N/D | N/D |
| 93 | 4-methylphenyl | 4-ethoxy-3-methoxyphenyl | 4-chlorophenyl | 114-119 | +++ | ++ |
| 94 | 4-methylphenyl | 4-fluoro-2-trifluoromethoxyphenyl | 4-bromophenyl | 109-115 | ++ | ++ |
| 95 | 4-methylphenyl | 4-fluoro-3-methylphenyl | 4-bromophenyl | 105-109 | ++++ | ++ |
| 96 | 4-methylphenyl | 4-hydroxy-3-nitrophenyl | 4-chlorophenyl | 138-143 | ++ | +++ |
| 97 | 4-methylphenyl | 4-methanesulfenylphenyl | 4-bromophenyl | 121-130 | ++++ | ++ |
| 98 | 4-methylphenyl | 4-methanesulfenylphenyl | 4-bromophenyl | N/D | ++++ | + |
| 99 | 4-methylphenyl | 4-methoxyphenyl | 4-bromophenyl | 130-133 | +++ | + |
| 100 | 4-methylphenyl | 4-methoxyphenyl | 4-chlorophenyl | 110-119 | ++++ | ++++ |
| 101 | 4-methylphenyl | 4-N,N-dimethylaminophenyl | 4-bromophenyl | 107-109 | + | − |
| 102 | 4-methylphenyl | 4-N,N-dimethylaminophenyl | 4-chlorophenyl | 96-99 | − | − |
| 103 | 4-methylphenyl | 4-phenoxyphenyl | 4-bromophenyl | 134-137 | +++ | ++++ |
| 104 | 4-methylphenyl | 4-phenoxyphenyl | 4-chlorophenyl | 119-126 | +++ | +++ |
| 105 | 4-methylphenyl | 5-bromo-3-indolyl | 4-bromophenyl | 190-193 | +++ | ++++ |
| 106 | 4-methylphenyl | 5-bromo-3-indolyl | 4-chlorophenyl | 184-188 | ++++ | ++++ |
| 107 | 4-methylphenyl | 5-chloro-3-indolyl | 4-bromophenyl | 200-203 | ++++ | ++++ |
| 108 | 4-methylphenyl | 5-chloro-3-indolyl | 4-chlorophenyl | 197-200 | ++++ | ++++ |
| 109 | 4-methylphenyl | 5-methylthiophen-2-yl | 4-bromophenyl | 73-76 | + | − |
| 110 | 4-methylphenyl | biphenyl-4-yl | 4-bromophenyl | 106-109 | ++ | + |
| 111 | 4-methylphenyl | biphenyl-4-yl | 4-chlorophenyl | 78-82 | ++ | + |
| 112 | 2,3,4,5,6-pentafluorophenyl | 4-fluoro-3-nitrophenyl | 4-carboxyphenyl | 223-225 | +++++ | ++++ |
| 113 | 4-methylphenyl | 4-fluoro-3-nitrophenyl | 4-bromophenyl | ND | ++++ | ++++ |

Potencies (IC$_{50}$) of the compound in the K-562 and DU 145 assays are indicated as follows:

−: greater than 100 µM;
+ >50 to 100 µM;
++ >25 to 50 µM;
+++ >10 to 25 µM;
++++ >1 to 10 µM;
+++++ ≤1 µM

TABLE 2

Compound Examples $$\underset{Ar^1}{\overset{}{\bigvee}}\underset{S}{\overset{O}{\underset{}{\bigvee}}}\underset{Ar^2}{\overset{Ar^3}{}}$$

| Example | Ar¹ | Ar² | Ar³ | m.p. (° C.) | K 562 | DU 145 |
|---|---|---|---|---|---|---|
| 114 | 2,4-dichlorophenyl | 2,3-dichlorophenyl | 4-chlorophenyl | 103-106 | ++++ | ++++ |
| 115 | 2,4-dichlorophenyl | 2,4,6-trihydroxyphenyl | 4-chlorophenyl | 64-67 | − | ++ |
| 116 | 2,4-dichlorophenyl | 2,4,6-trimethoxyphenyl | 4-chlorophenyl | 89-92 | ++ | ++++ |
| 117 | 2,4-dichlorophenyl | 3-ethoxy-4-hydroxyphenyl | 4-chlorophenyl | 114-118 | ++++ | +++ |
| 118 | 2,4-dichlorophenyl | 3-indolyl | 4-chlorophenyl | 181-186 | +++ | +++ |
| 119 | 2,4-dichlorophenyl | 3-methylthiophen-2-yl | 4-chlorophenyl | 72-76 | + | +++ |
| 120 | 2,4-dichlorophenyl | 4-(N,N-dimethylamino)phenyl | 4-chlorophenyl | 106-111 | − | + |
| 121 | 2,4-dichlorophenyl | 4-benzyloxyphenyl | 4-chlorophenyl | 101-107 | +++ | ++++ |

TABLE 2-continued

Compound Examples

| Example | Ar¹ | Ar² | Ar³ | m.p. (° C.) | K 562 | DU 145 |
|---|---|---|---|---|---|---|
| 122 | 2,4-dichlorophenyl | 4-chlorophenyl | 4-chlorophenyl | 105-109 | ++++ | +++ |
| 123 | 2,4-dichlorophenyl | 5-bromo-3-indolyl | 4-chlorophenyl | 163-166 | ++++ | +++ |
| 124 | 2,4-dichlorophenyl | 5-methylthiophen-2-yl | 4-chlorophenyl | 88-92 | + | + |
| 125 | 2-chlorophenyl | 2,3,4-trimethoxyphenyl | 4-chlorophenyl | 78-95 | ++++ | +++ |
| 126 | 2-chlorophenyl | 2,4,6-trimethoxyphenyl | 4-chlorophenyl | 86-92 | +++ | + |
| 127 | 2-chlorophenyl | 4-(N,N-dimethylamino)phenyl | 4-chlorophenyl | 121-128 | + | − |
| 128 | 2-chlorophenyl | 4-benzyloxyphenyl | 2-chlorophenyl | 124-128 | ++++ | ++++ |
| 129 | 2-chlorophenyl | 4-bromophenyl | 4-chlorophenyl | 106-112 | ++++ | +++ |
| 130 | 2-chlorophenyl | 4-chlorophenyl | 4-chlorophenyl | 105-112 | ++++ | +++ |
| 131 | 2-chlorophenyl | 4-ethoxy-3-methoxyphenyl | 4-chlorophenyl | 101-105 | ++++ | + |
| 132 | 2-chlorophenyl | 4-hydroxy-3-nitrophenyl | 4-chlorophenyl | 123-131 | +++ | +++ |
| 133 | 2-fluorophenyl | 2-methoxyphenyl | 4-chlorophenyl | 72-76 | ++++ | +++ |
| 134 | 2-fluorophenyl | 3-methylthiophen-2-yl | 4-chlorophenyl | 98-107 | + | + |
| 135 | 2-fluorophenyl | 3-methylthiophen-2-yl | 4-chlorophenyl | 95-98 | + | + |
| 136 | 3,4-dichlorophenyl | 2,4,6-trihydroxyphenyl | 4-chlorophenyl | 58-61 | ++ | ++ |
| 137 | 3,4-dichlorophenyl | 2,4,6-trimethoxyphenyl | 4-chlorophenyl | 115-118 | +++ | +++ |
| 138 | 3,4-dichlorophenyl | 2,5-dimethoxyphenyl | 4-chlorophenyl | 135-138 | +++ | +++ |
| 139 | 3,4-dichlorophenyl | 2-benzyloxyphenyl | 4-chlorophenyl | 97-100 | +++ | +++ |
| 140 | 3,4-dichlorophenyl | 2-methoxyphenyl | 4-chlorophenyl | 109-112 | +++ | +++ |
| 140 | 3,4-dichlorophenyl | 3-methylthiophen-2-yl | 4-chlorophenyl | 99-103 | + | + |
| 142 | 3,4-dichlorophenyl | 4-(N,N-dimethylamino)phenyl | 4-chlorophenyl | 102-107 | + | + |
| 143 | 3,4-dichlorophenyl | 4-ethoxy-3-methoxyphenyl | 4-chlorophenyl | 72-74 | ++++ | ++ |
| 144 | 3,4-dichlorophenyl | 4-hydroxyphenyl | 4-chlorophenyl | 154-156 | ++++ | ++++ |
| 145 | 3-chlorophenyl | 2,4-dihydroxyphenyl | 4-bromophenyl | N/D | ++ | + |
| 146 | 3-chlorophenyl | 4-benzyloxyphenyl | 4-bromophenyl | 108-110 | ++++ | ++++ |
| 147 | 4-bromophenyl | 3,5-dibromo-4-hydroxyphenyl | 4-bromophenyl | N/D | +++ | ++++ |
| 148 | 4-bromophenyl | 3,5-dichloro-4-hydroxyphenyl | 4-bromophenyl | N/D | +++ | +++ |
| 149 | 4-bromophenyl | 3,5-dimethylphenyl | 4-chlorophenyl | 121-123 | +++ | +++ |
| 150 | 4-bromophenyl | 3-bromo-4-hydroxyphenyl | 4-carboxyphenyl | N/D | ++ | ++ |
| 151 | 4-bromophenyl | 3-carboxy-4-hydroxyphenyl | 4-bromophenyl | N/D | ++ | +++ |
| 152 | 4-bromophenyl | 3-hydroxy-4-nitrophenyl | 2,3,4,5,6-pentafluorophenyl | N/D | ++++ | +++ |
| 153 | 4-bromophenyl | 3-hydroxy-4-nitrophenyl | 3,4,5-trimethoxyphenyl | 95-98 | N/D | N/D |
| 154 | 4-bromophenyl | 3-hydroxy-4-nitrophenyl | 3-chloro-4-nitrophenyl | 142-144 | ++++ | ++++ |
| 155 | 4-bromophenyl | 3-hydroxy-4-nitrophenyl | 4-bromophenyl | 90-92 | ++++ | +++ |
| 156 | 4-bromophenyl | 3-hydroxy-4-nitrophenyl | 4-carboxyphenyl | 210-216 | ++++ | +++ |
| 157 | 4-bromophenyl | 3-hydroxy-4-nitrophenyl | 4-cyanophenyl | 160-164 | ++++ | ++++ |
| 158 | 4-bromophenyl | 3-hydroxy-4-nitrophenyl | 4-nitrophenyl | 96-98 | ++++ | ++++ |
| 159 | 4-bromophenyl | 3-hydroxy-4-nitrophenyl | 4-(1-pyrrolidino)phenyl | N/D | − | − |
| 160 | 4-bromophenyl | 3-hydroxy-4-nitrophenyl | 4-trifluoromethylphenyl | 110-112 | ++++ | ++++ |
| 161 | 4-bromophenyl | 3-hydroxy-4-nitrophenyl | 5-chloro-2-hydroxyphenyl | N/D | +++ | +++ |
| 162 | 4-bromophenyl | 4-(2-(N,N-diethylamino)ethyl-carbamoyl)-3,5-dimethyl-1H-pyrrol-2-yl | 4-bromophenyl | 99-101 | ++++ | ++++ |
| 163 | 4-bromophenyl | 4-(2-(N,N-diethylamino)ethyl-carbamoyl)-3,5-dimethyl-1H-pyrrol-2-yl | 4-carboxyphenyl | N/D | + | + |
| 164 | 4-bromophenyl | 4-(N,N-dimethylamino)phenyl | 4-carboxyphenyl | N/D | ++ | + |
| 165 | 4-bromophenyl | 4-bromo-3-nitrophenyl | 4-carboxyphenyl | 168-170 | ++++ | ++++ |
| 166 | 4-bromophenyl | 4-bromophenyl | 4-carboxyphenyl | 126-130 | ++++ | +++ |
| 167 | 4-bromophenyl | 4-carboxy-3,5-dimethyl-1H-pyrrol-2-yl | 4-bromophenyl | N/D | + | + |
| 168 | 4-bromophenyl | 4-chloro-3-nitrophenyl | 4-carboxyphenyl | 148-150 | +++++ | ++++ |
| 169 | 4-bromophenyl | 4-chlorophenyl | 2-chlorophenyl | 95-100 | ++++ | ++ |
| 170 | 4-bromophenyl | 4-ethoxycarbonyl-3,5-dimethyl-1H-pyrrol-2-yl | 4-bromophenyl | N/D | ++ | + |
| 171 | 4-bromophenyl | 4-fluoro-3-methoxyphenyl | 4-carboxyphenyl | 180-182 | N/D | N/D |
| 172 | 4-bromophenyl | 4-fluoro-3-nitrophenyl | 4-carboxyphenyl | 170-172 | ++++ | ++++ |
| 173 | 4-bromophenyl | 4-hydroxy-3,5-diiodophenyl | 4-bromophenyl | 158-160 | ++++ | +++ |
| 174 | 4-bromophenyl | 4-hydroxy-3-methoxy-5-nitrophenyl | 4-bromophenyl | N/D | ++ | ++ |
| 175 | 4-bromophenyl | 4-hydroxy-3-nitrophenyl | 2,3,4,5,6-pentafluorophenyl | N/D | +++ | +++ |
| 176 | 4-bromophenyl | 4-hydroxy-3-nitrophenyl | 2,4-dichlorophenyl | 88-90 | ++++ | +++ |
| 177 | 4-bromophenyl | 4-hydroxy-3-nitrophenyl | 2,4-dihydroxyphenyl | N/D | + | − |
| 178 | 4-bromophenyl | 4-hydroxy-3-nitrophenyl | 3,4,5-trimethoxyphenyl | 110-112 | ++++ | ++++ |
| 179 | 4-bromophenyl | 4-hydroxy-3-nitrophenyl | 3-chloro-4-nitrophenyl | 178-182 | ++++ | ++++ |
| 180 | 4-bromophenyl | 4-hydroxy-3-nitrophenyl | 4-bromophenyl | N/D | N/D | N/D |
| 181 | 4-bromophenyl | 4-hydroxy-3-nitrophenyl | 4-carboxyphenyl | N/D | + | + |
| 182 | 4-bromophenyl | 4-hydroxy-3-nitrophenyl | 4-cyanophenyl | N/D | +++ | +++ |
| 183 | 4-bromophenyl | 4-hydroxy-3-nitrophenyl | 4-methoxyphenyl | N/D | +++ | +++ |
| 184 | 4-bromophenyl | 4-hydroxy-3-nitrophenyl | 4-nitrophenyl | N/D | +++ | +++ |
| 185 | 4-bromophenyl | 4-hydroxy-3-nitrophenyl | 4-(1-pyrrolidino)phenyl | N/D | − | − |
| 186 | 4-bromophenyl | 4-hydroxy-3-nitrophenyl | 4-trifluoromethylphenyl | 114-116 | ++++ | +++ |

TABLE 2-continued

Compound Examples

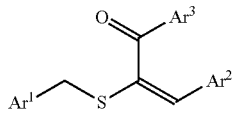

| Example | Ar¹ | Ar² | Ar³ | m.p. (° C.) | K 562 | DU 145 |
|---|---|---|---|---|---|---|
| 187 | 4-bromophenyl | 4-hydroxy-3-nitrophenyl | 5-chloro-2-hydroxy-phenyl | N/D | +++ | ++ |
| 188 | 4-bromophenyl | 4-methanesulfenylphenyl | 4-carboxyphenyl | N/D | ++ | ++ |
| 189 | 4-chlorophenyl | 2,3,5-trichlorophenyl | 4-bromophenyl | 147-152 | ++++ | ++++ |
| 190 | 4-chlorophenyl | 2,3-dichlorophenyl | 4-bromophenyl | 135-141 | +++ | +++ |
| 191 | 4-chlorophenyl | 2,3-dichlorophenyl | 4-chlorophenyl | 127-132 | ++++ | +++ |
| 192 | 4-chlorophenyl | 2,4,6-trihydroxyphenyl | 4-chlorophenyl | 107-110 | − | − |
| 193 | 4-chlorophenyl | 2,4,6-trimethoxyphenyl | 4-bromophenyl | 115-119 | +++ | ++++ |
| 194 | 4-chlorophenyl | 2,4,6-trimethoxyphenyl | 4-nitrophenyl | 144-148 | + | − |
| 195 | 4-chlorophenyl | 2,4-dichlorophenyl | 4-chlorophenyl | 104-106 | ++ | ++ |
| 196 | 4-chlorophenyl | 2,4-dihydroxyphenyl | 4-chlorophenyl | 160-164 | + | + |
| 197 | 4-chlorophenyl | 2,5-dimethylphenyl | 4-chlorophenyl | 119-123 | +++ | +++ |
| 198 | 4-chlorophenyl | 2-methoxyphenyl | 4-bromophenyl | 101-107 | +++ | ++++ |
| 199 | 4-chlorophenyl | 2-methoxyphenyl | 4-chlorophenyl | 102-108 | ++++ | ++++ |
| 200 | 4-chlorophenyl | 2-methoxyphenyl | 4-nitrophenyl | 109-113 | ++++ | +++ |
| 201 | 4-chlorophenyl | 2-pyrrolyl | 4-chlorophenyl | 128-135 | +++ | ++ |
| 202 | 4-chlorophenyl | 3,5-dimethylphenyl | 4-chlorophenyl | 122-127 | +++ | +++ |
| 203 | 4-chlorophenyl | 3-hydroxy-4-methoxyphenyl | 4-bromophenyl | 106-116 | ++++ | ++++ |
| 204 | 4-chlorophenyl | 3-hydroxy-4-methoxyphenyl | 4-chlorophenyl | 119-123 | +++++ | ++++ |
| 205 | 4-chlorophenyl | 3-methylthiophen-2-yl | 4-bromophenyl | 125-138 | ++ | ++ |
| 206 | 4-chlorophenyl | 3-methylthiophen-2-yl | 4-chlorophenyl | 121-127 | + | + |
| 207 | 4-chlorophenyl | 3-methylthiophen-2-yl | 4-nitrophenyl | 127-131 | − | − |
| 208 | 4-chlorophenyl | 4-(N,N-dimethylamino)phenyl | 4-bromophenyl | 109-114 | ++++ | +++ |
| 209 | 4-chlorophenyl | 4-(N,N-dimethylamino)phenyl | 4-carboxyphenyl | 168-170 | ++++ | ++++ |
| 210 | 4-chlorophenyl | 4-(N,N-dimethylamino)phenyl | 4-chlorophenyl | 111-118 | +++ | − |
| 211 | 4.chlorophenyl | 4-(N,N-dimethylamino)phenyl | 4-nitrophenyl | 135-141 | + | − |
| 212 | 4-chlorophenyl | 4-benzyloxyphenyl | 4-chlorophenyl | 116-118 | +++ | ++++ |
| 213 | 4-chlorophenyl | 4-bromo-3-nitrophenyl | 4-carboxyphenyl | 172-176 | +++++ | ++++ |
| 214 | 4-chlorophenyl | 4-bromophenyl | 4-bromophenyl | 132-137 | ++++ | ++++ |
| 215 | 4-chlorophenyl | 4-bromophenyl | 4-chlorophenyl | 104-109 | ++++ | ++++ |
| 216 | 4-chlorophenyl | 4-chloro-3-nitrophenyl | 4-carboxyphenyl | 180-184 | +++++ | ++++ |
| 217 | 4-chlorophenyl | 4-chlorophenyl | 2-chlorophenyl | 103-105 | ++++ | + |
| 218 | 4-chlorophenyl | 4-chlorophenyl | 4-bromophenyl | 99-102 | ++++ | +++ |
| 219 | 4-chlorophenyl | 4-fluoro-3-nitrophenyl | 4-carboxyphenyl | N/D | N/D | N/D |
| 220 | 4-chlorophenyl | 4-hydroxy-3-nitrophenyl | 4-chlorophenyl | 123-127 | +++ | +++ |
| 221 | 4-chlorophenyl | 4-hydroxyphenyl | 4-bromophenyl | 142-146 | ++++ | +++ |
| 222 | 4-chlorophenyl | 4-hydroxyphenyl | 4-chlorophenyl | 188-194 | ++++ | +++ |
| 223 | 4-chlorophenyl | 4-methanesulfenylphenyl | 4-carboxyphenyl | 150-154 | − | − |
| 224 | 4-chlorophenyl | 4-methanesulfenylphenyl | 4-chlorophenyl | 57-65 | ++++ | ++ |
| 225 | 4-chlorophenyl | 4-methoxyphenyl | 4-bromophenyl | 97-102 | ++++ | +++ |
| 226 | 4-chlorophenyl | 4-methoxyphenyl | 4-bromophenyl | 97-100 | ++++ | ++ |
| 227 | 4-chlorophenyl | 4-methoxyphenyl | 4-carboxyphenyl | N/D | ++ | ++ |
| 228 | 4-chlorophenyl | 4-methoxyphenyl | 4-chlorophenyl | 105-111 | ++++ | +++ |
| 229 | 4-chlorophenyl | 5-methylthiophen-2-yl | 4-bromophenyl | 116-118 | + | − |
| 230 | 4-chlorophenyl | 5-methylthiophen-2-yl | 4-chlorophenyl | 115-118 | + | + |
| 231 | 4-chlorophenyl | 5-methylthiophen-2-yl | 4-nitrophenyl | 136-139 | ++ | ++ |
| 232 | 4-fluorophenyl | 2,3,4-trimethoxyphenyl | 4-chlorophenyl | 87-93 | N/D | N/D |
| 233 | 4-fluorophenyl | 2,4,6-trimethoxyphenyl | 4-bromophenyl | 108-110 | ++++ | ++++ |
| 234 | 4-fluorophenyl | 2,4,6-trimethoxyphenyl | 4-chlorophenyl | N/D | +++ | +++ |
| 235 | 4-fluorophenyl | 2,5-dimethylphenyl | 4-bromophenyl | 138-141 | + | ++++ |
| 236 | 4-fluorophenyl | 2-benzyloxyphenyl | 4-bromophenyl | 124-129 | ++++ | ++++ |
| 237 | 4-fluorophenyl | 2-benzyloxyphenyl | 4-bromophenyl | 137-142 | N/D | N/D |
| 238 | 4-fluorophenyl | 2-benzyloxyphenyl | 4-chlorophenyl | 116-121 | N/D | N/D |
| 239 | 4-fluorophenyl | 2-methoxyphenyl | 4-bromophenyl | 102-106 | N/D | N/D |
| 240 | 4-fluorophenyl | 2-methoxyphenyl | 4-chlorophenyl | 101-104 | ++++ | +++ |
| 241 | 4-fluorophenyl | 2-quinolinyl | 4-bromophenyl | 129-134 | N/D | N/D |
| 242 | 4-fluorophenyl | 3,5-dimethylphenyl | 4-bromophenyl | 104-107 | ++++ | +++ |
| 243 | 4-fluorophenyl | 3-hydroxy-4-methoxyphenyl | 4-bromophenyl | 107-115 | N/D | N/D |
| 244 | 4-fluorophenyl | 3-hydroxy-4-methoxyphenyl | 4-carboxyphenyl | N/D | ++++ | +++ |
| 245 | 4-fluorophenyl | 3-indolyl | 4-chlorophenyl | 195-198 | N/D | N/D |
| 246 | 4-fluorophenyl | 3-methylthiophen-2-yl | 4-bromophenyl | 149-155 | − | + |
| 247 | 4-fluorophenyl | 3-methylthiophen-2-yl | 4-chlorophenyl | 134-145 | N/D | N/D |
| 248 | 4-fluorophenyl | 4-(2-(N,N-diethylamino)ethyl-carbamoyl)-3,5-dimethyl-1H-pyrrol-2-yl | 4-carboxyphenyl | N/D | + | + |
| 249 | 4-fluorophenyl | 4-(N,N-dimethylamino)phenyl | 4-bromophenyl | 79-83 | ++++ | ++ |
| 250 | 4-fluorophenyl | 4-(N,N-dimethylamino)phenyl | 4-carboxyphenyl | N/D | +++ | ++ |
| 251 | 4-fluorophenyl | 4-(N,N-dimethylamino)phenyl | 4-chlorophenyl | 95-101 | N/D | N/D |
| 252 | 4-fluorophenyl | 4-bromo-3-nitrophenyl | 4-carboxyphenyl | N/D | +++++ | ++++ |
| 253 | 4-fluorophenyl | 4-bromophenyl | 4-bromophenyl | 94-97 | ++++ | ++ |
| 254 | 4-fluorophenyl | 4-bromophenyl | 4-chlorophenyl | 82-84 | ++++ | +++ |

TABLE 2-continued

Compound Examples $$\text{Ar}^1\text{-CH}_2\text{-S-C(=Ar}^2\text{)-C(=O)-Ar}^3$$

| Example | Ar¹ | Ar² | Ar³ | m.p. (° C.) | K 562 | DU 145 |
|---|---|---|---|---|---|---|
| 255 | 4-fluorophenyl | 4-chloro-3-nitrophenyl | 4-carboxyphenyl | 164-166 | +++++ | ++++ |
| 256 | 4-fluorophenyl | 4-chlorophenyl | 4-chlorophenyl | 86-89 | ++++ | +++ |
| 257 | 4-fluorophenyl | 4-ethoxy-3-methoxyphenyl | 4-bromophenyl | 97-104 | ++++ | + |
| 258 | 4-fluorophenyl | 4-ethoxy-3-methoxyphenyl | 4-chlorophenyl | 97-102 | N/D | N/D |
| 259 | 4-fluorophenyl | 4-fluoro-2-methylphenyl | 4-bromophenyl | 85-91 | N/D | N/D |
| 260 | 4-fluorophenyl | 4-fluoro-2-trifluoromethylphenyl | 4-bromophenyl | 102-108 | +++ | +++ |
| 261 | 4-fluorophenyl | 4-fluoro-3-nitrophenyl | 4-carboxyphenyl | N/D | N/D | N/D |
| 262 | 4-fluorophenyl | 4-hydroxy-3-nitrophenyl | 4-carboxyphenyl | N/D | + | − |
| 263 | 4-fluorophenyl | 4-hydroxyphenyl | 4-bromophenyl | 187-192 | N/D | N/D |
| 264 | 4-fluorophenyl | 4-hydroxyphenyl | 4-chlorophenyl | 146-152 | N/D | N/D |
| 265 | 4-fluorophenyl | 4-methoxyphenyl | 4-bromophenyl | 84-90 | ++++ | ++ |
| 266 | 4-fluorophenyl | 5-bromo-3-indolyl | 4-chlorophenyl | 87-93 | N/D | N/D |
| 267 | 4-fluorophenyl | 5-chloro-3-indolyl | 4-bromophenyl | 131-135 | ++++ | ++++ |
| 268 | 4-fluorophenyl | 5-methylthiophen-2-yl | 4-chlorophenyl | 122-128 | N/D | N/D |
| 269 | 4-fluorophenyl | 5-phenylthiophen-2-yl | 4-bromophenyl | 125-131 | N/D | N/D |
| 270 | 4-methylphenyl | 2,3,4-trihydroxyphenyl | 4-chlorophenyl | 76-79 | + | + |
| 271 | 4-methylphenyl | 2,3-dichlorophenyl | 4-chlorophenyl | 92-107 | ++ | ++ |
| 272 | 4-methylphenyl | 2,4,6-trihydroxyphenyl | 4-chlorophenyl | 69-75 | + | + |
| 273 | 4-methylphenyl | 2,5-dimethylphenyl | 4-chlorophenyl | 98-106 | +++ | +++ |
| 274 | 4-methylphenyl | 2-benzyloxyphenyl | 4-chlorophenyl | 98-104 | ++++ | ++++ |
| 275 | 4-methylphenyl | 2-bromophenyl | 4-chlorophenyl | 100-102 | N/D | N/D |
| 276 | 4-methylphenyl | 2-fluoro-5-nitrophenyl | 4-chlorophenyl | 142-144 | ++++ | ++++ |
| 277 | 4-methylphenyl | 2-fluorophenyl | 4-bromophenyl | 96-98 | ++++ | +++ |
| 278 | 4-methylphenyl | 2-fluorophenyl | 4-chlorophenyl | 88-90 | N/D | N/D |
| 279 | 4-methylphenyl | 2-methoxyphenyl | 4-chlorophenyl | N/D | +++ | +++ |
| 280 | 4-methylphenyl | 2-pyrrolyl | 4-chlorophenyl | 69-70 | ++++ | ++ |
| 281 | 4-methylphenyl | 3,5-dichlorophenyl | 4-chlorophenyl | 104-110 | +++ | +++ |
| 282 | 4-methylphenyl | 3-indolyl | 4-chlorophenyl | 186-194 | N/D | N/D |
| 283 | 4-methylphenyl | 3-methylthiophen-2-yl | 4-chlorophenyl | 126-137 | +++ | +++ |
| 284 | 4-methylphenyl | 4-(2-(N,N-diethylamino)ethyl-carbamoyl)-3,5-dimethyl-1H-pyrrol-2-yl | 4-carboxyphenyl | N/D | + | + |
| 285 | 4-methylphenyl | 4-(N,N-dimethylamino)phenyl | 4-chlorophenyl | 62-67 | +++ | +++ |
| 286 | 4-methylphenyl | 4-bromophenyl | 4-chlorophenyl | 92-96 | ++++ | +++ |
| 287 | 4-methylphenyl | 4-chloro-3-nitrophenyl | 4-carboxyphenyl | 160-162 | +++++ | ++++ |
| 288 | 4-methylphenyl | 4-chlorophenyl | 4-chlorophenyl | 80-83 | ++++ | +++ |
| 289 | 4-methylphenyl | 4-ethoxy-3-methoxyphenyl | 4-chlorophenyl | 82-88 | ++ | ++ |
| 290 | 4-methylphenyl | 4-fluoro-2-trifluoromethylphenyl | 4-chlorophenyl | 96-103 | + | + |
| 291 | 4-methylphenyl | 4-fluoro-3-methylphenyl | 4-chlorophenyl | 57-61 | +++ | ++ |
| 292 | 4-methylphenyl | 4-hydroxyphenyl | 4-chlorophenyl | 162-164 | ++++ | +++ |
| 293 | 4-methylphenyl | 4-methanesulfenylphenyl | 4-bromophenyl | N/D | ++ | − |
| 294 | 4-methylphenyl | 4-methanesulfenylphenyl | 4-chlorophenyl | 85-91 | +++ | ++ |
| 295 | 4-methylphenyl | 5-bromo-3-indolyl | 4-chlorophenyl | 160-169 | ++++ | ++++ |
| 296 | 4-methylphenyl | 5-chloro-3-indolyl | 4-chlorophenyl | 167-178 | ++++ | ++++ |
| 297 | 4-methylphenyl | 5-chloro-3-indolyl | 4-chlorophenyl | 909-92 | ++++ | ++++ |
| 298 | 4-methylphenyl | 5-methylthiophen-2-yl | 4-chlorophenyl | 76-82 | + | + |
| 299 | 2,4-dichlorophenyl | 4-bromo-3-nitrophenyl | 4-carboxyphenyl | 160-162 | +++++ | ++++ |
| 300 | 2,4-dichlorophenyl | 4-chloro-3-nitrophenyl | 4-carboxyphenyl | 126-130 | +++++ | ++++ |
| 301 | 2,4-dichlorophenyl | 4-fluoro-3-nitrophenyl | 4-carboxyphenyl | 124-128 | +++++ | ++++ |
| 302 | 2-chlorophenyl | 4-bromo-3-nitrophenyl | 4-carboxyphenyl | 64-68 | ++++ | ++++ |
| 303 | 2-chlorophenyl | 4-fluoro-3-nitrophenyl | 4-carboxyphenyl | 198-200 | ++++ | ++++ |
| 304 | 2-fluorophenyl | 4-chloro-3-nitrophenyl | 4-carboxyphenyl | 138-140 | +++++ | ++++ |
| 305 | 4-bromophenyl | 2,4,5-trimethoxyphenyl | 4-nitrophenyl | ND | +++ | +++ |
| 306 | 4-bromophenyl | 2-fluorophenyl | 4-carboxyphenyl | 140-142 | +++ | +++ |
| 307 | 4-bromophenyl | 3-(3-(2,5-dimethyl-3,6-dioxocyclohexa-1,4-dienyl)-3-methylbutanoyloxy)-4-nitrophenyl | 4-bromophenyl | ND | ++++ | ++++ |
| 308 | 4-bromophenyl | 4-(4-methylpiperazin-1-yl)-3-nitrophenyl | 4-carboxyphenyl | 220-222 | ++++ | +++ |
| 309 | 4-bromophenyl | 4-(ethoxycarbonyl)-3,5-dimethyl-1H-pyrrol-2-yl | 4-((4-bromophenyl)methylsulfenyl)-3-nitrophenyl | 164-168 | − | − |
| 310 | 4-bromophenyl | 4-fluoro-3-nitrophenyl | 2,3,4,5,6-pentafluorophenyl | 280-284 | ++++ | ++++ |
| 311 | 4-bromophenyl | 4-fluoro-3-nitrophenyl | 4-(2-(4-methylpiperazin-1-yl)ethylcarbamoyl)phenyl | 60-62 | +++++ | ++++ |
| 312 | 4-bromophenyl | 4-fluoro-3-nitrophenyl | 4-(2-(morpholin-4-yl)ethylcarbamoyl)phenyl | 116-118 | ++++ | ++++ |
| 313 | 4-bromophenyl | 4-fluoro-3-nitrophenyl | 4-(2-(N,N-diethylamino)ethylcarbamoyl)phenyl | 60-61 | +++++ | ++++ |
| 314 | 4-bromophenyl | 4-fluoro-3-nitrophenyl | 4-(3-(4-methylpiperazin-1-yl)propylcarbamoyl)phenyl | 60-62 | ++++ | ++++ |

TABLE 2-continued

Compound Examples

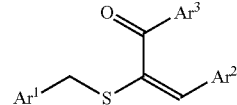

| Example | Ar¹ | Ar² | Ar³ | m.p. (° C.) | K 562 | DU 145 |
|---|---|---|---|---|---|---|
| 315 | 4-bromophenyl | 4-fluoro-3-nitrophenyl | 4-(4-(5-(trifluoromethyl)pyridin-2-yl)piperazine-1-carbonyl)phenyl | 86-89 | ++++ | ++++ |
| 316 | 4-bromophenyl | 4-fluoro-3-nitrophenyl | 4-[4-(2-hydroxyethyl)piperazine-1-carbonyl]phenyl | 117-119 | +++++ | +++++ |
| 317 | 4-bromophenyl | 4-fluoro-3-nitrophenyl | 4-chloro-3-nitrophenyl | 162-164 | − | − |
| 318 | 4-bromophenyl | 4-fluoro-3-nitrophenyl | 4-fluorophenyl | 108-110 | +++++ | +++++ |
| 319 | 4-bromophenyl | 4-fluorophenyl | 4-((4-bromophenyl)methylsulfenyl)-3-nitrophenyl | 140-142 | − | − |
| 320 | 4-bromophenyl | 4-nitrophenyl | 4-bromophenyl | 121-124 | ++++ | ++++ |
| 321 | 4-chlorophenyl | 3-pyridinyl | 4-bromophenyl | ND | ++++ | ++++ |
| 322 | 4-chlorophenyl | 3-pyridinyl | 4-chlorophenyl | ND | ++++ | ++++ |
| 323 | 4-chlorophenyl | 4-carboxyphenyl | 4-carboxyphenyl | 266-268 | − | − |
| 324 | 4-chlorophenyl | 4-chlorophenyl | 4-chlorophenyl | 92-94 | ++++ | +++ |
| 325 | 4-chlorophenyl | 4-methoxyphenyl | 4-chlorophenyl | 66-68 | ++++ | +++ |
| 326 | 4-chlorophenyl | 4-nitrophenyl | 4-chlorophenyl | 89-90 | ++++ | ++++ |
| 327 | 4-chlorophenyl | 4-trifluoromethylphenyl | 4-chlorophenyl | 50-51 | ++++ | ++++ |
| 328 | 4-fluorophenyl | 3-nitro-4-(4-(phenylmethyl)piperazin-1-yl)phenyl | 4-carboxyphenyl | 114-115 | ++++ | ++++ |
| 329 | 4-fluorophenyl | 4-(2-(4-methylpiperazin-1-yl)ethyl-amino)-3-nitrophenyl | 4-fluorophenyl | 120-121 | +++++ | ++++ |
| 330 | 4-fluorophenyl | 4-(4-(2-hydroxyethyl)piperazin-1-yl)-3-nitrophenyl | 4-fluorophenyl | LIQUID | +++++ | ++++ |
| 331 | 4-fluorophenyl | 4-[4-(2-hydroxyethyl)piperazine-1-carbonyl]phenyl | 4-fluoro-3-nitrophenyl | 68-70 | +++++ | ++++ |
| 332 | 4-fluorophenyl | 4-acetamido-3-nitrophenyl | 4-carboxyphenyl | 176-178 | ++++ | +++ |
| 333 | 4-fluorophenyl | 4-amino-3-nitrophenyl | 4-carboxyphenyl | 210-214 | +++ | +++ |
| 334 | 4-fluorophenyl | 4-bromophenyl | 4-carboxyphenyl | 144-146 | − | − |
| 335 | 4-fluorophenyl | 4-fluoro-3-nitrophenyl | 4-((4-fluorophenyl)methylsulfenyl)-3-nitrophenyl | 78-82 | ++++ | +++ |
| 336 | 4-fluorophenyl | 4-fluoro-3-nitrophenyl | 4-((4-methylphenyl)sulfonyloxy)phenyl | 120-121 | ++++ | ++++ |
| 337 | 4-fluorophenyl | 4-fluoro-3-nitrophenyl | 4-(2-(4-methylpiperazin-1-yl)ethylcarbamoyl)phenyl | 116-118 | +++ | +++ |
| 338 | 4-fluorophenyl | 4-fluoro-3-nitrophenyl | 4-(2-(N,N-diethylamino)ethoxy)phenyl | LIQUID | +++++ | ++++ |
| 339 | 4-fluorophenyl | 4-fluoro-3-nitrophenyl | 4-(3-(2,5-dimethyl-3,6-dioxocyclohexa-1,4-dienyl)-3-methylbutanoyloxy)phenyl | 62-64 | ++++ | ++++ |
| 340 | 4-fluorophenyl | 4-fluoro-3-nitrophenyl | 4-(3-(morpholin-4-yl)propoxy)phenyl | 64-66 | ++++ | ++++ |
| 341 | 4-fluorophenyl | 4-fluoro-3-nitrophenyl | 4-fluorophenyl | 88-90 | +++++ | ++++ |
| 342 | 4-fluorophenyl | 4-fluoro-3-nitrophenyl | 4-hydroxyphenyl | 160-166 | +++++ | +++++ |
| 343 | 4-fluorophenyl | 4-fluoro-3-nitrophenyl | 4-sulfamoylphenyl | 66-70 | ++++ | ++++ |
| 344 | 4-fluorophenyl | 4-fluoro-3-nitrophenyl | phenyl | 90-92 | +++++ | ++++ |
| 345 | 4-methoxyphenyl | 4-fluorophenyl | 4-chlorophenyl | 72-74 | ++++ | +++ |
| 346 | 4-methoxyphenyl | 4-methoxyphenyl | 4-chlorophenyl | 46-48 | ++++ | +++ |
| 347 | 4-methylphenyl | 4-fluoro-3-nitrophenyl | 4-carboxyphenyl | 148-150 | +++++ | ++++ |
| 348 | 4-methylphenyl | 4-fluoro-3-nitrophenyl | 4-carboxyphenyl | 120-124 | ++++ | +++ |
| 349 | 4-methylphenyl | 4-fluoro-3-nitrophenyl | 4-chloro-3-nitrophenyl | 122-124 | +++++ | ++++ |
| 350 | 4-trifluoromethyl-phenyl | 4-chloro-3-nitrophenyl | 4-carboxyphenyl | 126-130 | ++++ | ++++ |
| 351 | 4-trifluoromethyl-phenyl | 4-fluoro-3-nitrophenyl | 4-carboxyphenyl | 183-186 | +++++ | ++++ |
| 352 | 6-bromo-1H-benzo[d]imidazol-2-yl | 4-fluoro-3-nitrophenyl | 4-carboxyphenyl | 154-155 | ++++ | ++++ |
| 353 | phenyl | 4-fluoro-3-nitrophenyl | 4-carboxyphenyl | 154-158 | +++++ | ++++ |

Potencies (IC$_{50}$) of the compound in the K-562 and DU 145 assays are indicated as follows:

−: greater than 100 μM;

+ >50 to 100 μM;

++ >25 to 50 μM;

+++ >10 to 25 μM;

++++ >1 to 10 μM;

+++++ ≤1 μM

TABLE 3

Compound Examples

[Chemical structure: Ar¹-CH₂-S(O)-C(=CHAr²)-C(=O)-Ar³]

| Example | Ar¹ | Ar² | Ar³ | m.p. (° C.) | K 562 | DU 145 |
|---|---|---|---|---|---|---|
| 354 | 2-chlorophenyl | 2,4,6-trimethoxyphenyl | 4-chlorophenyl | 174-181 | + | +++ |
| 355 | 4-chlorophenyl | 4-fluoro-2-trifluoromethylphenyl | 4-chlorophenyl | 162-166 | + | + |

Potencies (IC$_{50}$) of the compound in the K-562 and DU 145 assays are indicated as follows:
−: greater than 100 μM;
+ >50 to 100 μM;
++ >25 to 50 μM;
+++ >10 to 25 μM;
++++ >1 to 10 μM;
+++++ ≤1 μM

TABLE 4

Compound Examples

[Chemical structure: Ar¹-CH₂-S(O)₂-C(=CHAr²)-C(=O)-Ar³]

| Example | Ar¹ | Ar² | Ar³ | m.p. (° C.) | K 562 | DU 145 |
|---|---|---|---|---|---|---|
| 356 | 2,4-dichlorophenyl | 5-methylthiophen-2-yl | 4-chlorophenyl | 115-117 | ++ | +++ |
| 357 | 2-chlorophenyl | 2,4,6-trimethoxyphenyl | 4-chlorophenyl | 185-192 | ++ | − |
| 358 | 2-chlorophenyl | 2-benzyloxyphenyl | 4-chlorophenyl | 137-148 | ++++ | ++++ |
| 359 | 2-chlorophenyl | 3,5-dimethoxyphenyl | 4-chlorophenyl | 133-138 | + | − |
| 360 | 2-chlorophenyl | 4-bromophenyl | 4-chlorophenyl | 186-192 | ++ | ++ |
| 361 | 2-chlorophenyl | 4-ethoxy-3-methoxyphenyl | 4-chlorophenyl | 123-128 | +++ | +++ |
| 362 | 2-chlorophenyl | 4-hydroxy-3-nitrophenyl | 4-chlorophenyl | 222-226 | N/D | N/D |
| 363 | 2-chlorophenyl | 4-methoxyphenyl | 4-chlorophenyl | 195-210 | N/D | N/D |
| 364 | 3,4-dichlorophenyl | 2-methoxyphenyl | 4-chlorophenyl | 154-157 | ++++ | ++++ |
| 365 | 3,4-dichlorophenyl | 4-fluoro-2-trifluoromethylphenyl | 4-chlorophenyl | N/D | N/D | N/D |
| 366 | 3,4-dichlorophenyl | 4-hydroxyphenyl | 4-chlorophenyl | 195-198 | +++ | +++ |
| 367 | 3,4-dichlorophenyl | 4-hydroxyphenyl | 4-chlorophenyl | N/D | N/D | N/D |
| 368 | 4-bromophenyl | 3,5-dibromo-4-hydroxyphenyl | 4-bromophenyl | N/D | ++ | ++ |
| 369 | 4-bromophenyl | 3,5-dichloro-4-hydroxyphenyl | 4-bromophenyl | N/D | ++ | ++ |
| 370 | 4-bromophenyl | 4-(2-(N,N-diethylamino)ethyl-carbamoyl)-3,5-dimethyl-1H-pyrrol-2-yl | 4-bromophenyl | 157-159 | ++++ | ++++ |
| 371 | 4-bromophenyl | 4-bromophenyl | 4-methoxyphenyl | 146-148 | ++++ | ++++ |
| 372 | 4-bromophenyl | 4-chloro-3-nitrophenyl | 4-carboxyphenyl | N/D | ++ | ++ |
| 373 | 4-bromophenyl | 4-hydroxy-3-nitrophenyl | 2,3,4,5,6-penta-fluorophenyl | N/D | + | + |
| 374 | 4-bromophenyl | 4-hydroxy-3-nitrophenyl | 4-bromophenyl | 110-112 | ++++ | +++ |
| 375 | 4-chlorophenyl | 2,3,4-trimethoxyphenyl | 4-chlorophenyl | 148-151 | ++++ | +++ |
| 376 | 4-chlorophenyl | 2,3,5-trichlorophenyl | 4-bromophenyl | 181-188 | ++++ | ++++ |
| 377 | 4-chlorophenyl | 2,4,6-trihydroxyphenyl | 4-chlorophenyl | 232-236 | − | − |
| 378 | 4-chlorophenyl | 2,4,6-trimethoxyphenyl | 4-bromophenyl | 207-210 | ++ | ++ |
| 379 | 4-chlorophenyl | 2,4,6-trimethoxyphenyl | 4-nitrophenyl | 62-64 | +++ | +++ |
| 380 | 4-chlorophenyl | 2,5-dimethylphenyl | 4-chlorophenyl | 129-136 | +++ | +++ |
| 381 | 4-chlorophenyl | 2-benzyloxyphenyl | 4-bromophenyl | 136-142 | ++++ | +++ |
| 382 | 4-chlorophenyl | 2-hydroxy-4-methoxyphenyl | 4-bromophenyl | 72-78 | +++ | +++ |
| 383 | 4-chlorophenyl | 2-methoxyphenyl | 4-chlorophenyl | 135-142 | ++ | ++ |
| 384 | 4-chlorophenyl | 2-methoxyphenyl | 4-nitrophenyl | 136-141 | +++ | +++ |
| 385 | 4-chlorophenyl | 3,5-dimethylphenyl | 4-chlorophenyl | 146-152 | ++++ | ++++ |
| 386 | 4-chlorophenyl | 3-ethoxy-4-hydroxyphenyl | 4-chlorophenyl | 134-139 | +++ | +++ |
| 387 | 4-chlorophenyl | 3-methoxythiophen-2-yl | 4-bromophenyl | 128-136 | ++ | + |
| 388 | 4-chlorophenyl | 3-methylthiophen-2-yl | 4-chlorophenyl | 130-139 | ++ | ++ |
| 389 | 4-chlorophenyl | 3-methylthiophen-2-yl | 4-nitrophenyl | 174-179 | ++++ | ++++ |
| 390 | 4-chlorophenyl | 4-(N,N-dimethylamino)phenyl | 4-carboxyphenyl | 176-180 | N/D | N/D |
| 391 | 4-chlorophenyl | 4-benzyloxyphenyl | 4-chlorophenyl | 91-99 | ++++ | ++++ |
| 392 | 4-chlorophenyl | 4-bromophenyl | 4-chlorophenyl | 100-103 | +++ | +++ |

TABLE 4-continued

Compound Examples

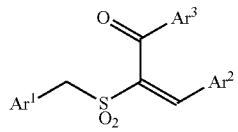

| Example | Ar¹ | Ar² | Ar³ | m.p. (° C.) | K 562 | DU 145 |
|---|---|---|---|---|---|---|
| 393 | 4-chlorophenyl | 4-hydroxy-3-nitrophenyl | 4-chlorophenyl | 72-74 | ++ | ++ |
| 394 | 4-chlorophenyl | 4-methanesulfenylphenyl | 4-chlorophenyl | 94-108 | +++ | +++ |
| 395 | 4-chlorophenyl | 4-methoxyphenyl | 4-bromophenyl | 152-155 | +++ | ++ |
| 396 | 4-chlorophenyl | 5-methylthiophen-2-yl | 4-chlorophenyl | 148-152 | ++++ | ++++ |
| 397 | 4-chlorophenyl | 5-methylthiophen-2-yl | 4-nitrophenyl | 180-182 | +++ | ++ |
| 398 | 4-chlorophenyl | biphenyl-4-yl | 4-chlorophenyl | 65-72 | ++ | ++ |
| 399 | 4-fluorophenyl | 2,4,6-trimethoxyphenyl | 4-bromophenyl | 176-182 | + | + |
| 400 | 4-fluorophenyl | 2,4,6-trimethoxyphenyl | 4-chlorophenyl | 134-138 | ++++ | ++ |
| 401 | 4-fluorophenyl | 2,5-dimethylphenyl | 4-bromophenyl | 167-173 | ++++ | ++++ |
| 402 | 4-fluorophenyl | 2-benzyloxyphenyl | 4-chlorophenyl | 139-145 | N/D | N/D |
| 403 | 4-fluorophenyl | 2-fluoro-5-nitrophenyl | 4-bromophenyl | 172-177 | + | − |
| 404 | 4-fluorophenyl | 2-methoxyphenyl | 4-bromophenyl | 145-151 | N/D | N/D |
| 405 | 4-fluorophenyl | 3,5-dimethylphenyl | 4-bromophenyl | 140-143 | +++ | +++ |
| 406 | 4-fluorophenyl | 3-indolyl | 4-chlorophenyl | >200 | + | + |
| 407 | 4-fluorophenyl | 3-methylthiophen-2-yl | 4-chlorophenyl | 146-158 | ++++ | +++ |
| 408 | 4-fluorophenyl | 4-(N,N-dimethylamino)phenyl | 4-bromophenyl | 155-162 | + | + |
| 409 | 4-fluorophenyl | 4-bromophenyl | 4-bromophenyl | 164-168 | +++ | ++ |
| 410 | 4-fluorophenyl | 4-bromophenyl | 4-chlorophenyl | N/D | + | − |
| 411 | 4-fluorophenyl | 4-ethoxy-3-methoxyphenyl | 4-bromophenyl | N/D | N/D | N/D |
| 412 | 4-fluorophenyl | 4-ethoxy-3-methoxyphenyl | 4-chlorophenyl | 145-149 | ++ | + |
| 413 | 4-fluorophenyl | 4-hydroxyphenyl | 4-bromophenyl | 188-192 | N/D | N/D |
| 414 | 4-fluorophenyl | 4-methanesulfenylphenyl | 4-bromophenyl | 157-161 | N/D | N/D |
| 415 | 4-fluorophenyl | 4-methoxyphenyl | 4-bromophenyl | 121-123 | N/D | N/D |
| 416 | 4-fluorophenyl | 5-methylthiophen-2-yl | 4-bromophenyl | 156-161 | N/D | N/D |
| 417 | 4-fluorophenyl | 5-methylthiophen-2-yl | 4-chlorophenyl | 116-120 | N/D | N/D |
| 418 | 4-iodophenyl | 4-bromophenyl | 4-bromophenyl | 168-170 | >50 | >50 |
| 419 | 4-iodophenyl | 4-bromophenyl | 4-iodophenyl | 180-182 | ++ | ++ |
| 420 | 4-iodophenyl | 4-iodophenyl | 4-bromophenyl | 160-162 | >50 | ++ |
| 421 | 4-iodophenyl | 4-iodophenyl | 4-iodophenyl | 175-177 | >50 | ++ |
| 422 | 4-methoxyphenyl | 2,4,6-trimethoxyphenyl | 4-methoxyphenyl | 60-62 | N/D | N/D |
| 423 | 4-methylphenyl | 2,3-dichlorophenyl | 4-chlorophenyl | 162-165 | ++++ | ++++ |
| 424 | 4-methylphenyl | 2,4,6-trihydroxyphenyl | 4-chlorophenyl | 167-180 | − | − |
| 425 | 4-methylphenyl | 2,5-dimethylphenyl | 4-chlorophenyl | 176-182 | ++++ | ++++ |
| 426 | 4-methylphenyl | 2-benzyloxyphenyl | 4-chlorophenyl | 112-129 | ++++ | ++++ |
| 427 | 4-methylphenyl | 2-bromophenyl | 4-chlorophenyl | N/D | N/D | N/D |
| 428 | 4-methylphenyl | 2-methoxyphenyl | 4-chlorophenyl | N/D | +++ | +++ |
| 429 | 4-methylphenyl | 3,5-dimethylphenyl | 4-chlorophenyl | 169-178 | +++ | +++ |
| 430 | 4-methylphenyl | 3-indolyl | 4-chlorophenyl | 160-165 | − | ++ |
| 431 | 4-methylphenyl | 3-methylthiophen-2-yl | 4-chlorophenyl | 98-105 | ++ | ++ |
| 432 | 4-methylphenyl | 4-(N,N-dimethylamino)phenyl | 4-chlorophenyl | 150-154 | + | + |
| 433 | 4-methylphenyl | 4-bromophenyl | 4-chlorophenyl | 160-165 | +++ | ++ |
| 434 | 4-methylphenyl | 4-chlorophenyl | 4-chlorophenyl | 128-133 | ++ | ++ |
| 435 | 4-methylphenyl | 4-ethoxy-3-methoxyphenyl | 4-chlorophenyl | 65-72 | +++ | +++ |
| 436 | 4-methylphenyl | 4-methanesulfenylphenyl | 4-bromophenyl | N/D | +++ | +++ |
| 437 | 4-methylphenyl | 4-methanesulfenylphenyl | 4-chlorophenyl | 140-152 | ++ | +++ |
| 438 | 4-methylphenyl | 4-methanesulfonylphenyl | 4-bromophenyl | 110-112 | ++++ | +++ |
| 439 | 4-methylphenyl | 5-bromo-3-indolyl | 4-chlorophenyl | 186-195 | +++ | +++ |
| 440 | 4-methylphenyl | 5-methylthiophen-2-yl | 4-chlorophenyl | 171-178 | ++ | ++ |

Potencies (IC$_{50}$) of the compound in the K-562 and DU 145 assays are indicated as follows:

−: greater than 100 μM;

+ >50 to 100 μM;

++ >25 to 50 μM;

+++ >10 to 25 μM;

++++ >1 to 10 μM;

+++++ ≤1 μM

TABLE 5

Compound Example

O
‖
Ar¹—S—C(=C(H)—Ar²)—C(=O)—Ar³

| Example | Ar¹ | Ar² | Ar³ | m.p. (° C.) | K 562 | DU 145 |
|---|---|---|---|---|---|---|
| 441 | 4-bromophenyl | 4-fluoro-3-nitrophenyl | methyl 4-benzoate | 109-110 | +++++ | +++++ |

Potencies (IC$_{50}$) of the compound in the K-562 and DU 145 assays are indicated as follows:
−: greater than 100 μM;
+ >50 to 100 μM;
++ >25 to 50 μM;
+++ >10 to 25 μM;
++++ >1 to 10 μM;
+++++ ≤1 μM All references cited herein are incorporated by reference. The present invention may be embodied in other specific forms without departing from the spirit or essential attributes thereof and, accordingly, reference should be made to the appended claims, rather than to the foregoing specification, as indicating the scope of the invention.

What is claimed is:
1. A compound of formula I, or a salt thereof:

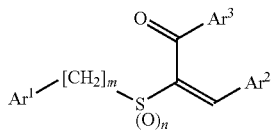

I wherein:
m is 0 or 1;
n is 0, 1, or 2, provided that when m is 0, n is 0 or 1;
Ar¹ is selected from the group consisting of unsubstituted aryl other than unsubstituted phenyl, and substituted aryl; wherein said substituted aryl is aryl substituted with one or more substituents independently selected from the group consisting of —R¹; —Ar⁴; —(C$_1$-C$_3$) alkylene-Ar⁴; (C$_2$-C$_6$)alkenyl; (C$_2$-C$_6$)alkynyl; halogen; —C≡N; —NO$_2$; —C(=O)R³; —C(=O)OR³; —C(=O)NR⁴$_2$; —C(=NR³)NR⁴$_2$; —OR²; —OC(=O)(C$_1$-C$_6$)alkyl; —OC(=O)(C$_1$-C$_6$)alkylene-R⁵; —OC(=O)O(C$_1$-C$_6$)alkyl; —OC(=O)NR⁴$_2$; —NR⁴$_2$; —NR⁴C(=O)R³; —NR⁴C(=O)Ar⁴; —NR⁴C(=O)O(C$_1$-C$_6$)alkyl; —NR⁴C(=O)NR⁴$_2$; —NR⁴SO$_2$R³; —NR⁴SO$_2$Ar⁴; —P(=O)(OR³)$_2$; —OP(=O)(OR³)$_2$; —S(O)$_a$R²; —OSO$_2$(C$_1$-C$_6$)alkyl; —OSO$_2$Ar⁴; —SO$_2$NR⁴$_2$; and (C$_1$-C$_3$)Perfluoroalkyl;
Ar² is selected from the group consisting of unsubstituted aryl and substituted aryl; wherein, when Ar² is substituted aryl, said substituted aryl is aryl substituted with one or more substituents independently selected from the group consisting of —R¹; —Ar⁴; —(C$_1$-C$_3$)alkylene-Ar⁴; (C$_2$-C$_6$)alkenyl; (C$_2$-C$_6$)alkynyl; halogen; —C≡N; —NO$_2$; —C(=O)R³; —C(=O)OR³; —C(=O)NR⁴$_2$; —C(=NR³)NR⁴$_2$; —OR²; —OC(=O)(C$_1$-C$_6$)alkyl; —OC(=O)(C$_1$-C$_6$)alkylene-R⁵; —OC(=O)O(C$_1$-C$_6$)alkyl; —OC(=O)NR⁴$_2$; —NR⁴$_2$; —NR⁴C(=O)R³; —NR⁴C(=O)Ar⁴; —NR⁴C(=O)O(C$_1$-C$_6$)alkyl; —NR⁴C(=O)NR⁴$_2$; —NR⁴SO$_2$R³; —NR⁴SO$_2$Ar⁴; —P(=O)(OR³)$_2$; —OP(=O)(OR³)$_2$; —S(O)$_a$R²; —OSO$_2$(C$_1$-C$_6$)alkyl; —OSO$_2$Ar⁴; —SO$_2$NR⁴$_2$; and (C$_1$-C$_3$)perfluoroalkyl;
Ar³ is aryl substituted with one or more substituents independently selected from the group consisting of —R¹; —Ar⁴; —(C$_1$-C$_3$)alkylene-Ar⁴; (C$_2$-C$_6$)alkenyl; (C$_2$-C$_6$)alkynyl; halogen; —C≡N; —NO$_2$; —C(=O)R³; —C(=O)OR³; —C(=O)NR⁴$_2$; —C(=NR³)NR⁴$_2$; —OR²; —OC(=O)(C$_1$-C$_6$)alkyl; —OC(=O)(C$_1$-C$_6$)alkylene-R⁵; —OC(=O)O(C$_1$-C$_6$)alkyl; —OC(=O)NR⁴$_2$; —NR⁴$_2$; —NR⁴C(=O)R³; —NR⁴C(=O)Ar⁴; —NR⁴C(=O)O(C$_1$-C$_6$)alkyl; —NR⁴C(=O)NR⁴$_2$; —NR⁴SO$_2$R³; —NR⁴SO$_2$Ar⁴; —P(=O)(OR³)$_2$; —OP(=O)(OR³)$_2$; —S(O)$_a$R²; —OSO$_2$(C$_1$-C$_6$)alkyl; —OSO$_2$Ar⁴; —SO$_2$NR⁴$_2$; and (C$_1$-C$_3$)perfluoroalkyl;
each R¹ is independently unsubstituted (C$_1$-C$_6$)alkyl or (C$_1$-C$_6$)alkyl substituted with up to five halogen atoms and up to two substituents selected from the group consisting of —C≡N; —C(=O)R³; —C(=O)OR³; —C(=O)NR⁴$_2$; —OR³; —OC(=O)(C$_1$-C$_6$)alkyl; —OC(=O)O(C$_1$-C$_6$)alkyl; —OC(=O)NR⁴$_2$; —NR⁴$_2$; —NR³C(=O)R³; —NR³C(=O)NR⁴$_2$; and —S(O)$_a$(C$_1$-C$_6$)alkyl;
each R² is independently selected from the group consisting of hydrogen, R¹, Ar⁴ and (C$_1$-C$_3$)alkylene-Ar⁴;
each R³ is independently hydrogen or (C$_1$-C$_6$)alkyl;
each R⁴ is independently hydrogen; (C$_1$-C$_6$)alkyl; —(C$_2$-C$_6$)alkylene-OR³; —(C$_1$-C$_6$)alkylene-C(=O)OR³; —(C$_1$-C$_6$)alkylene-OC(=O)R³; —(C$_2$-C$_6$)alkylene-NR⁶$_2$; —(C$_1$-C$_6$)alkylene-C(=O)NR⁶$_2$; —(C$_1$-C$_6$)alkylene-NR³C(=O)R³; —(C$_1$-C$_6$)alkylene-NR³C(=O)NR⁶$_2$; Ar⁴; or —(C$_1$-C$_3$)-alkyleneAr⁴; or, optionally, within any occurrence of NR⁴$_2$, independently of any other occurrence of NR⁴$_2$, the two R⁴ groups in combination are —(CH$_2$)$_b$— or —(CH$_2$)$_c$A(CH$_2$)$_2$—;
each R⁵ is independently Ar⁴ or 1,4-benzoquinon-2-yl optionally substituted with 0, 1, 2, or 3 alkyl groups;
each R⁶ is independently hydrogen; (C$_1$-C$_6$)alkyl; —(C$_2$-C$_6$)alkylene-OR³; —(C$_1$-C$_6$)alkylene-C(=O)OR³; —(C$_1$-C$_6$)alkylene-OC(=O)R³; —(C$_2$-C$_6$)alkylene-NR³$_2$; —(C$_1$-C$_6$)alkylene-C(=O)NR³$_2$; —(C$_1$-C$_6$)alkylene-NR³C(=O)R³; —(C$_1$-C$_6$)alkyleneNR³C(=O)NR³$_2$; —Ar⁴; or —(C$_1$-C$_3$)alkylene-Ar⁴; or, optionally, within any occurrence of NR⁶$_2$, independently of any other occurrence of NR⁶$_2$, the two R⁶ groups in combination are —(CH$_2$)$_b$— or —(CH$_2$)A(CH$_2$)$_2$—;

each a is independently selected from the group consisting of 0, 1, and 2;

each b is independently selected from the group consisting of 4, 5, and 6;

each c is independently selected from the group consisting of 2 and 3;

each A is independently selected from the group consisting of O, S, NR$^3$; NC(=O)R$^3$; NSO$_2$R$^3$; N(C$_2$-C$_6$)alkylene-OR$^3$; N(C$_1$-C$_6$)alkylene-C(=O)OR$^3$; N(C$_1$-C$_6$)alkylene-OC(=O)R$^3$; N(C$_2$-C$_6$)alkylene-NR$^3_2$; N(C$_1$-C$_6$)alkylene-C(=O)NR$^3_2$; N(C$_1$-C$_6$)alkylene-NR$^3$C(=O)R$^3$; N(C$_1$-C$_6$)alkylene-NR$^3$C(=O)NR$^3_2$; NAr$^4$; N(C$_1$-C$_3$)alkylene-Ar$^4$; and NC(=O)Ar$^4$;

each Ar$^4$ is independently selected from the group consisting of unsubstituted aryl, unsubstituted heteroaryl, and aryl or heteroaryl substituted with one or more substituents independently selected from the group consisting of (C$_1$-C$_6$)alkyl; (C$_2$-C$_6$)alkenyl; (C$_2$-C$_6$)alkynyl; halogen; —C≡N; —NO$_2$; —C(=O)R$^3$; —C(=O)OR$^3$; —C(=O)NR$^3_2$; —C(=NR$^3$)NR$^3_2$; —OR$^3$; —OC(=O)(C$_1$-C$_6$)alkyl; —OC(=O)O(C$_1$-C$_6$)alkyl; —OC(=O)NR$^3_2$; —NR$^3_2$; —NR$^3$C(=O)R$^3$; —NR$^3$C(=O)O(C$_1$-C$_6$)alkyl; —NR$^3$C(=O)NR$^3_2$; —P(=O)(OR$^3$)$_2$; —OP(=O)(OR$^3$)$_2$; —S(O)$_a$(C$_1$-C$_6$)alkyl; —SO$_2$NR$^3_2$; and (C$_1$-C$_3$)perfluoroalkyl;

with the proviso that:
if Ar$^1$ is substituted phenyl, then Ar$^3$ is other than 4-methylphenyl.

2. A compound according to claim 1 of formula I, or a salt thereof:

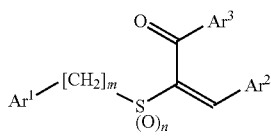

wherein:
m is 0 or 1;

n is 0, 1, or 2, provided that when m is 0, n is 0 or 1;

wherein substituents on Ar$^1$, Ar$^2$, and Ar$^3$ are independently selected from the group consisting of —R$^1$; (C$_2$-C$_6$)alkenyl; (C$_2$-C$_6$)alkynyl; halogen; —C≡N; —NO$_2$; —C(=O)R$^3$; —C(=O)OR$^3$; —C(=O)NR$^4_2$; —C(=NR$^3$)NR$^4_2$; —OR$^2$; —OC(=O)(C$_1$-C$_6$)alkyl; —OC(=O)O(C$_1$-C$_6$)alkyl; —OC(=O)NR$^4_2$; —NR$^4_2$; —NR$^3$C(=O)R$^3$; —NR$^3$C(=O)Ar$^4$; —NR$^3$C(=O)O(C$_1$-C$_6$)alkyl; —NR$^3$C(=O)NR$^4_2$; —P(=O)(OR$^3$)$_2$; —OP(=O)(OR$^3$)$_2$; —S(O)$_a$(C$_1$-C$_6$)alkyl; —SO$_2$NR$^4_2$; and (C$_1$-C$_3$)perfluoroalkyl;

each R$^1$ is independently unsubstituted (C$_1$-C$_6$)alkyl or (C$_1$-C$_6$)alkyl substituted with up to five halogen atoms and up to two substituents selected from the group consisting of —C≡N; —C(=O)R$^3$; —C(=O)OR$^3$; —C(=O)NR$^4_2$; —OR$^3$; —OC(=O)(C$_1$-C$_6$)alkyl; —OC(=O)O(C$_1$-C$_6$)alkyl; —OC(=O)NR$^4_2$; —NR$^4_2$; —NR$^3$C(=O)R$^3$; —NR$^3$C(=O)NR$^4_2$; and —S(O)$_a$(C$_1$-C$_6$)alkyl;

each R$^2$ is independently selected from the group consisting of hydrogen, R$^1$, Ar$^4$ and (C$_1$-C$_3$)alkylene-Ar$^4$;

each R$^3$ is independently hydrogen or (C$_1$-C$_6$)alkyl;

each R$^4$ is independently hydrogen or (C$_1$-C$_6$)alkyl; or, optionally, within any occurrence of NR$^4_2$, independently of any other occurrence of NR$^4_2$, the two R$^4$ groups in combination are —(CH$_2$)$_b$— or —(CH$_2$)$_c$A(CH$_2$)$_2$—;

each a is independently selected from the group consisting of 0, 1, and 2;

each b is independently selected from the group consisting of 4, 5, and 6;

each c is independently selected from the group consisting of 2 and 3;

each A is independently selected from the group consisting of O, S, NR$^3$; and NC(=O)R$^3$; and each Ar$^4$ is independently selected from the group consisting of unsubstituted aryl, unsubstituted heteroaryl, and aryl or heteroaryl substituted with one or more substituents independently selected from the group consisting of (C$_1$-C$_6$)alkyl; (C$_2$-C$_6$)alkenyl; (C$_2$-C$_6$)alkynyl; halogen; —C≡N; —NO$_2$; —C(=O)R$^3$; —C(=O)OR$^3$; —C(=O)NR$^4_2$; —C(=NR$^3$)NR$^4_2$; —OR$^3$; —OC(=O)(C$_1$-C$_6$)alkyl; —OC(=O)O(C$_1$-C$_6$)alkyl; —OC(=O)NR$^4_2$; —NR$^4_2$; —NR$^3$C(=O)R$^3$; —NR$^3$C(=O)O(C$_1$-C$_6$)alkyl; —NR$^3$C(=O)NR$^4_2$; —P(=O)(OR$^3$)$_2$; —OP(=O)(OR$^3$)$_2$; —S(O)$_a$(C$_1$-C$_6$)alkyl; —SO$_2$NR$^4_2$; and (C$_1$-C$_3$)perfluoroalkyl;

with the proviso that:
if Ar$^1$ is substituted phenyl, then Ar$^3$ is other than 4-methylphenyl.

3. A compound according to claim 1, or a salt thereof, wherein Ar$^1$ is substituted phenyl.

4. A compound according to claim 1, wherein Ar$^3$ is phenyl substituted at the 4-position with —C(=O)OH, or a salt of such a compound.

5. A compound according to claim 1, or a salt thereof, wherein Ar$^2$ is selected from the group consisting of unsubstituted and substituted phenyl; and unsubstituted and substituted biphenyl.

6. A compound according to claim 1, or a salt thereof, wherein Ar$^2$ is other than unsubstituted phenyl.

7. A compound according to claim 1, or a salt thereof, wherein m is 0.

8. A compound according to claim 7, or a salt thereof, wherein n is 0.

9. A compound according to claim 8, or a salt thereof, wherein Ar$^1$ is substituted phenyl.

10. A compound according to claim 9, wherein Ar$^3$ is phenyl substituted at the 4-position with —C(=O)OH, or a salt of such a compound.

11. A compound according to claim 8 selected from the group consisting of (E)-1-(4-bromophenyl)-2-(2-bromophenylsulfenyl)-3-(4-bromophenyl)prop-2-en-1-one; (E)-1-(4-bromophenyl)-2-(4-bromophenylsulfenyl)-3-(2,4-dichlorophenyl)prop-2-en-1-one; (E)-1-(4-bromophenyl)-2-(4-bromophenylsulfenyl)-3-(2,4-difluorophenyl)prop-2-en-1-one; (E)-1-(4-chlorophenyl)-2-(4-bromophenylsulfenyl)-3-(2,4-difluorophenyl)prop-2-en-1-one; (E)-1-(4-bromophenyl)-2-(4-bromophenylsulfenyl)-3-(2-chloro-4-fluorophenyl)prop-2-en-1-one; (E)-1-(2,3,4,5,6-pentafluorophenyl)-2-(4-bromophenylsulfenyl)-3-(3-bromo-4-hydroxyphenyl)prop-2-en-1-one; (E)-1-(2,3,4,5,6-pentafluorophenyl)-2-(4-bromophenylsulfenyl)-3-(3-hydroxy-4-nitrophenyl)prop-2-en-1-one; (E)-1-(4-bromophenyl)-2-(4-bromophenylsulfenyl)-3-(4-bromo-3-hydroxyphenyl)prop-2-en-1-one; (E)-1-(4-bromophenyl)-2-(4-bromophenylsulfenyl)-3-(4-bromo-3-nitrophenyl)prop-2-en-1-one; (E)-1-(4-bromophenyl)-2-(4-bromophenylsulfenyl)-3-(4-bromophenyl)prop-2-en-1-one; (E)-1-(4-chlorophenyl)-2-(4-bromophenylsulfenyl)-3-(4-bromophenyl)prop-2-en-1-one; (E)-1-(4-bromophenyl)-2-

(4-bromophenylsulfenyl)-3-(4-chloro-3-nitrophenyl)prop-2-en-1-one; (E)-1-(4-bromophenyl)-2-(4-bromophenylsulfenyl)-3-(4-chlorophenyl)prop-2-en-1-one; (E)-1-(4-bromophenyl)-2-(4-bromophenylsulfenyl)-3-(4-hydroxy-3-methoxyphenyl)prop-2-en-1-one; (E)-1-(2,3,4,5,6-pentafluorophenyl)-2-(4-bromophenylsulfenyl)-3-(4-hydroxy-3-nitrophenyl)prop-2-en-1-one; (E)-1-(4-bromophenyl)-2-(4-bromophenylsulfenyl)-3-(4-hydroxy-3-nitrophenyl)prop-2-en-1-one; (E)-1-(4-bromophenyl)-2-(4-bromophenylsulfenyl)-3-(4-iodophenyl)prop-2-en-1-one; (E)-1-(4-bromophenyl)-2-(4-bromophenylsulfenyl)-3-(4-trifluoromethoxyphenyl)prop-2-en-1-one; (E)-1-(4-chlorophenyl)-2-(4-chlorophenylsulfenyl)-3-(4-chlorophenyl)prop-2-en-1-one; (E)-1-(4-chlorophenyl)-2-(4-fluorophenylsulfenyl)-3-(2-benzyloxyphenyl)prop-2-en-1-one; (E)-1-(4-bromophenyl)-2-(4-methoxyphenylsulfenyl)-3-(2,4-dichlorophenyl)prop-2-en-1-one; (E)-1-(4-chlorophenyl)-2-(4-methoxyphenylsulfenyl)-3-(2-benzyloxyphenyl)prop-2-en-1-one; (E)-1-(4-chlorophenyl)-2-(4-methylphenylsulfenyl)-3-(3-hydroxy-4-methoxyphenyl)prop-2-en-1-one; (E)-1-(4-chlorophenyl)-2-(4-methylphenylsulfenyl)-3-(4-methoxyphenyl)prop-2-en-1-one; (E)-1-(4-bromophenyl)-2-(2,3,4,5,6-pentafluorophenylsulfenyl)-3-(3-hydroxy-4-nitrophenyl)prop-2-en-1-one; (E)-1-(4-bromophenyl)-2-(2-bromophenylsulfenyl)-3-(4-hydroxy-3-nitrophenyl)prop-2-en-1-one; (E)-1-(4-bromophenyl)-2-(4-bromophenylsulfenyl)-3-(2-fluoro-4-methoxyphenyl)prop-2-en-1-one; (E)-1-(4-chlorophenyl)-2-(4-bromophenylsulfenyl)-3-(2-fluorophenyl)prop-2-en-1-one; (E)-1-(4-chlorophenyl)-2-(4-bromophenylsulfenyl)-3-(3,5-dimethylphenyl)prop-2-en-1-one; (E)-1-(4-bromophenyl)-2-(4-bromophenylsulfenyl)-3-(4-fluoro-3-methoxyphenyl)prop-2-en-1-one; (E)-1-(4-bromophenyl)-2-(4-bromophenylsulfenyl)-3-(4-fluorophenyl)prop-2-en-1-one; (E)-1-(4-chlorophenyl)-2-(4-bromophenylsulfenyl)-3-(4-methanesulfenylphenyl)prop-2-en-1-one; (E)-1-(4-methoxyphenyl)-2-(4-fluorophenylsulfenyl)-3-(3-hydroxy-4-methoxyphenyl)prop-2-en-1-one; (E)-1-(4-chlorophenyl)-2-(4-methylphenylsulfenyl)-3-(2-fluoro-5-nitrophenyl)prop-2-en-1-one; (E)-1-(4-chlorophenyl)-2-(4-methylphenylsulfenyl)-3-(4-acetoxyphenyl)prop-2-en-1-one; (E)-1-(4-bromophenyl)-2-(4-methylphenylsulfenyl)-3-(4-chlorophenyl)prop-2-en-1-one; (E)-1-(4-bromophenyl)-2-(4-methylphenylsulfenyl)-3-(4-phenoxyphenyl)prop-2-en-1-one; (E)-1-(4-bromophenyl)-2-(2,3,4,5,6-pentafluorophenylsulfenyl)-3-(4-hydroxy-3-nitrophenyl)prop-2-en-1-one; (E)-1-(4-chlorophenyl)-2-(4-bromophenylsulfenyl)-3-(2,5-dimethylphenyl)prop-2-en-1-one; (E)-1-(4-chlorophenyl)-2-(4-bromophenylsulfenyl)-3-(2-benzyloxyphenyl)prop-2-en-1-one; (E)-1-(4-chlorophenyl)-2-(4-bromophenylsulfenyl)-3-(2-methoxyphenyl)prop-2-en-1-one; (E)-1-(4-bromophenyl)-2-(4-bromophenylsulfenyl)-3-(4-methoxyphenyl)prop-2-en-1-one; (E)-1-(4-methoxyphenyl)-2-(4-fluorophenylsulfenyl)-3-(4-methoxyphenyl)prop-2-en-1-one; (E)-1-(4-bromophenyl)-2-(4-methoxyphenylsulfenyl)-3-(4-bromophenyl)prop-2-en-1-one; (E)-1-(4-chlorophenyl)-2-(4-methylphenylsulfenyl)-3-(2,4-dichlorophenyl)prop-2-en-1-one; (E)-1-(4-chlorophenyl)-2-(4-methylphenylsulfenyl)-3-(4-chlorophenyl)prop-2-en-1-one; (E)-1-(4-bromophenyl)-2-(4-methylphenylsulfenyl)-3-(4-fluoro-3-methylphenyl)prop-2-en-1-one; (E)-1-(4-bromophenyl)-2-(4-methylphenylsulfenyl)-3-(4-methanesulfenylphenyl)prop-2-en-1-one; (E)-1-(4-chlorophenyl)-2-(4-methylphenylsulfenyl)-3-(4-phenoxyphenyl)prop-2-en-1-one; (E)-1-(4-chlorophenyl)-2-(2-bromophenylsulfenyl)-3-(4-hydroxy-3-nitrophenyl)prop-2-en-1-one; (E)-1-(4-chlorophenyl)-2-(4-bromophenylsulfenyl)-3-(4-methoxyphenyl)prop-2-en-1-one; (E)-1-(4-chlorophenyl)-2-(4-methylphenylsulfenyl)-3-(2-methoxyphenyl)prop-2-en-1-one; (E)-1-(4-chlorophenyl)-2-(4-methylphenylsulfenyl)-3-(4-ethoxy-3-methoxyphenyl)prop-2-en-1-one; (E)-1-(4-chlorophenyl)-2-(4-methylphenylsulfenyl)-3-(4-hydroxy-3-nitrophenyl)prop-2-en-1-one; (E)-1-(4-bromophenyl)-2-(4-methylphenylsulfenyl)-3-(4-methanesulfenylphenyl)prop-2-en-1-one; (E)-1-(2,3,4,5,6-pentafluorophenyl)-2-(4-bromophenylsulfenyl)-3-(3-carboxy-4-hydroxyphenyl)prop-2-en-1-one; (E)-1-(4-bromophenyl)-2-(4-bromophenylsulfenyl)-3-(4-hydroxy-3-nitrophenyl)prop-2-en-1-one; (E)-1-(4-chlorophenyl)-2-(4-methylphenylsulfenyl)-3-(2,3,4,5,6-pentafluorophenyl)prop-2-en-1-one; (E)-1-(4-bromophenyl)-2-(4-methylphenylsulfenyl)-3-(4-fluoro-2-trifluoromethoxyphenyl)prop-2-en-1-one; (E)-1-(4-bromophenyl)-2-(4-methylphenylsulfenyl)-3-(4-methoxyphenyl)prop-2-en-1-one; (E)-1-(4-bromophenyl)-2-(4-methylphenylsulfenyl)-3-(4-fluoro-3-nitrophenyl)prop-2-en-1-one; and (E)-1-(4-carboxyphenyl)-2-(2,3,4,5,6-pentafluorophenylsulfenyl)-3-(4-fluoro-3-nitrophenyl)prop-2-en-1-one; or salts thereof.

12. A compound according to claim 7, or a salt thereof, wherein n is 1.

13. A compound according to claim 12, or a salt thereof, wherein $Ar^1$ is substituted phenyl.

14. A compound according to claim 13, wherein $Ar^3$ is phenyl substituted at the 4-position with —C(=O)OH, or a salt of such a compound.

15. A compound according to claim 1, or a salt thereof, wherein m is 1.

16. A compound according to claim 15, or a salt thereof, wherein n is 0.

17. A compound according to claim 16, or a salt thereof, wherein $Ar^1$ is substituted phenyl.

18. A compound according to claim 17, wherein $Ar^3$ is phenyl substituted at the 4-position with —C(=O)OH, or a salt of such a compound.

19. A compound according to claim 16 selected from the group consisting of (E)-1-(4-carboxyphenyl)-2-(4-bromophenylmethylsulfenyl)-3-(4-chloro-3-nitrophenyl)prop-2-en-1-one; (E)-1-(4-carboxyphenyl)-2-(4-chlorophenylmethylsulfenyl)-3-(4-bromo-3-nitrophenyl)prop-2-en-1-one; (E)-1-(4-carboxyphenyl)-2-(4-chlorophenylmethylsulfenyl)-3-(4-chloro-3-nitrophenyl)prop-2-en-1-one; (E)-1-(4-carboxyphenyl)-2-(4-fluorophenylmethylsulfenyl)-3-(4-bromo-3-nitrophenyl)prop-2-en-1-one; (E)-1-(4-carboxyphenyl)-2-(4-fluorophenylmethylsulfenyl)-3-(4-chloro-3-nitrophenyl)prop-2-en-1-one; (E)-1-(4-carboxyphenyl)-2-(4-methylphenylmethylsulfenyl)-3-(4-chloro-3-nitrophenyl)prop-2-en-1-one; (E)-1-(4-chlorophenyl)-2-(4-chlorophenylmethylsulfenyl)-3-(3-hydroxy-4-methoxyphenyl)prop-2-en-1-one; (E)-1-(2-chlorophenyl)-2-(2-chlorophenylmethylsulfenyl)-3-(4-benzyloxyphenyl)prop-2-en-1-one; (E)-1-(3,4,5-trimethoxyphenyl)-2-(4-bromophenylmethylsulfenyl)-3-(4-hydroxy-3-nitrophenyl)prop-2-en-1-one; (E)-1-(3-chloro-4-nitrophenyl)-2-(4-bromophenylmethylsulfenyl)-3-(3-hydroxy-4-nitrophenyl)prop-2-en-1-one; (E)-1-(3-chloro-4-nitrophenyl)-2-(4-bromophenylmethylsulfenyl)-3-(4-hydroxy-3-nitrophenyl)prop-2-en-1-one; (E)-1-(4-bromophenyl)-2-(3-chlorophenylmethylsulfenyl)-3-(4-benzyloxyphenyl)prop-2-en-1-one; (E)-1-(4-bromophenyl)-2-(4-bromophenylmethylsulfenyl)-3-(4-hydroxy-3,5-diiodophenyl)prop-2-en-1-one; (E)-1-(4-bromophenyl)-2-(4-chlorophenylmethylsulfenyl)-3-(2,3,5-trichlorophenyl)prop-2-en-1-one; (E)-1-(4-bromophenyl)-2-(4-chlorophenylmethylsulfenyl)-3-(3-hydroxy-4-methoxyphenyl)prop-2-en-1-one; (E)-1-(4-bromophenyl)-2-

(4-chlorophenylmethylsulfenyl)-3-(4-bromophenyl)prop-2-en-1-one; (E)-1-(4-bromophenyl)-2-(4-fluorophenylmethylsulfenyl)-3-(2,4,6-trimethoxyphenyl)prop-2-en-1-one; (E)-1-(4-bromophenyl)-2-(4-fluorophenylmethylsulfenyl)-3-(2-benzyloxyphenyl)prop-2-en-1-one; (E)-1-(4-carboxyphenyl)-2-(4-bromophenylmethylsulfenyl)-3-(4-bromo-3-nitrophenyl)prop-2-en-1-one; (E)-1-(4-carboxyphenyl)-2-(4-bromophenylmethylsulfenyl)-3-(4-bromophenyl)prop-2-en-1-one; (E)-1-(4-carboxyphenyl)-2-(4-bromophenylmethylsulfenyl)-3-(4-fluoro-3-nitrophenyl)prop-2-en-1-one; (E)-1-(4-carboxyphenyl)-2-(4-chlorophenylmethylsulfenyl)-3-(4-(N,N-dimethylamino)phenyl)prop-2-en-1-one; (E)-1-(4-chlorophenyl)-2-(2,4-dichlorophenylmethylsulfenyl)-3-(2,3-dichlorophenyl)prop-2-en-1-one; (E)-1-(4-chlorophenyl)-2-(3,4-dichlorophenylmethylsulfenyl)-3-(4-hydroxyphenyl)prop-2-en-1-one; (E)-1-(4-chlorophenyl)-2-(4-chlorophenylmethylsulfenyl)-3-(2-methoxyphenyl)prop-2-en-1-one; (E)-1-(4-chlorophenyl)-2-(4-chlorophenylmethylsulfenyl)-3-(4-bromophenyl)prop-2-en-1-one; (E)-1-(4-chlorophenyl)-2-(4-methylphenylmethylsulfenyl)-3-(2-benzyloxyphenyl)prop-2-en-1-one; (E)-1-(4-chlorophenyl)-2-(4-methylphenylmethylsulfenyl)-3-(2-fluoro-5-nitrophenyl)prop-2-en-1-one; (E)-1-(4-cyanophenyl)-2-(4-bromophenylmethylsulfenyl)-3-(3-hydroxy-4-nitrophenyl)prop-2-en-1-one; (E)-1-(4-nitrophenyl)-2-(4-bromophenylmethylsulfenyl)-3-(3-hydroxy-4-nitrophenyl)prop-2-en-1-one; (E)-1-(4-trifluoromethylphenyl)-2-(4-bromophenylmethylsulfenyl)-3-(3-hydroxy-4-nitrophenyl)prop-2-en-1-one; (E)-1-(2,3,4,5,6-pentafluorophenyl)-2-(4-bromophenylmethylsulfenyl)-3-(3-hydroxy-4-nitrophenyl)prop-2-en-1-one; (E)-1-(2,4-dichlorophenyl)-2-(4-bromophenylmethylsulfenyl)-3-(4-hydroxy-3-nitrophenyl)prop-2-en-1-one; (E)-1-(4-bromophenyl)-2-(4-bromophenylmethylsulfenyl)-3-(3,5-dibromo-4-hydroxyphenyl)prop-2-en-1-one; (E)-1-(4-bromophenyl)-2-(4-bromophenylmethylsulfenyl)-3-(3-hydroxy-4-nitrophenyl)prop-2-en-1-one; (E)-1-(4-bromophenyl)-2-(4-chlorophenylmethylsulfenyl)-3-(2,4,6-trimethoxyphenyl)prop-2-en-1-one; (E)-1-(4-bromophenyl)-2-(4-chlorophenylmethylsulfenyl)-3-(2-methoxyphenyl)prop-2-en-1-one; (E)-1-(4-bromophenyl)-2-(4-chlorophenylmethylsulfenyl)-3-(4-(N,N-dimethylamino)phenyl)prop-2-en-1-one; (E)-1-(4-bromophenyl)-2-(4-chlorophenylmethylsulfenyl)-3-(4-chlorophenyl)prop-2-en-1-one; (E)-1-(4-bromophenyl)-2-(4-chlorophenylmethylsulfenyl)-3-(4-hydroxyphenyl)prop-2-en-1-one; (E)-1-(4-bromophenyl)-2-(4-chlorophenylmethylsulfenyl)-3-(4-methoxyphenyl)prop-2-en-1-one; (E)-1-(4-bromophenyl)-2-(4-fluorophenylmethylsulfenyl)-3-(3,5-dimethylphenyl)prop-2-en-1-one; (E)-1-(4-bromophenyl)-2-(4-methylphenylmethylsulfenyl)-3-(2-fluorophenyl)prop-2-en-1-one; (E)-1-(4-carboxyphenyl)-2-(4-bromophenylmethylsulfenyl)-3-(3-hydroxy-4-nitrophenyl)prop-2-en-1-one; (E)-1-(4-carboxyphenyl)-2-(4-fluorophenylmethylsulfenyl)-3-(3-hydroxy-4-methoxyphenyl)prop-2-en-1-one; (E)-1-(4-chlorophenyl)-2-(2,4-dichlorophenylmethylsulfenyl)-3-(3-ethoxy-4-hydroxyphenyl)prop-2-en-1-one; (E)-1-(4-chlorophenyl)-2-(2,4-dichlorophenylmethylsulfenyl)-3-(4-benzyloxyphenyl)prop-2-en-1-one; (E)-1-(4-chlorophenyl)-2-(2,4-dichlorophenylmethylsulfenyl)-3-(4-chlorophenyl)prop-2-en-1-one; (E)-1-(4-chlorophenyl)-2-(2-chlorophenylmethylsulfenyl)-3-(2,3,4-trimethoxyphenyl)prop-2-en-1-one; (E)-1-(4-chlorophenyl)-2-(2-chlorophenylmethylsulfenyl)-3-(4-bromophenyl)prop-2-en-1-one; (E)-1-(4-chlorophenyl)-2-(2-chlorophenylmethylsulfenyl)-3-(4-chlorophenyl)prop-2-en-1-one; (E)-1-(4-chlorophenyl)-2-(2-fluorophenylmethylsulfenyl)-3-(2-methoxyphenyl)prop-2-en-1-one; (E)-1-(4-chlorophenyl)-2-(4-chlorophenylmethylsulfenyl)-3-(2,3-dichlorophenyl)prop-2-en-1-one; (E)-1-(4-chlorophenyl)-2-(4-chlorophenylmethylsulfenyl)-3-(4-benzyloxyphenyeprop-2-en-1-one; (E)-1-(4-chlorophenyl)-2-(4-chlorophenylmethylsulfenyl)-3-(4-hydroxyphenyl)prop-2-en-1-one; (E)-1-(4-chlorophenyl)-2-(4-chlorophenylmethylsulfenyl)-3-(4-methoxyphenyl)prop-2-en-1-one; (E)-1-(4-chlorophenyl)-2-(4-fluorophenylmethylsulfenyl)-3-(2-methoxyphenyl)prop-2-en-1-one; (E)-1-(4-chlorophenyl)-2-(4-fluorophenylmethylsulfenyl)-3-(4-bromophenyl)prop-2-en-1-one; (E)-1-(4-chlorophenyl)-2-(4-fluorophenylmethylsulfenyl)-3-(4-chlorophenyl)prop-2-en-1-one; (E)-1-(4-chlorophenyl)-2-(4-methylphenylmethylsulfenyl)-3-(4-bromophenyl)prop-2-en-1-one; (E)-1-(4-chlorophenyl)-2-(4-methylphenylmethylsulfenyl)-3-(4-chlorophenyl)prop-2-en-1-one; (E)-1-(4-chlorophenyl)-2-(4-methylphenylmethylsulfenyl)-3-(4-hydroxyphenyl)prop-2-en-1-one; (E)-1-(4-nitrophenyl)-2-(4-chlorophenylmethylsulfenyl)-3-(2-methoxyphenyl)prop-2-en-1-one; (E)-1-(4-trifluoromethylphenyl)-2-(4-bromophenylmethylsulfenyl)-3-(4-hydroxy-3-nitrophenyl)prop-2-en-1-one; (E)-1-(2,3,4,5,6-pentafluorophenyl)-2-(4-bromophenylmethylsulfenyl)-3-(4-hydroxy-3-nitrophenyl)prop-2-en-1-one; (E)-1-(2-chlorophenyl)-2-(4-bromophenylmethylsulfenyl)-3-(4-chlorophenyl)prop-2-en-1-one; (E)-1-(4-bromophenyl)-2-(4-bromophenylmethylsulfenyl)-3-(3,5-dichloro-4-hydroxyphenyl)prop-2-en-1-one; (E)-1-(4-bromophenyl)-2-(4-chlorophenylmethylsulfenyl)-3-(2,3-dichlorophenyl)prop-2-en-1-one; (E)-1-(4-bromophenyl)-2-(4-chlorophenylmethylsulfenyl)-3-(4-methoxyphenyl)prop-2-en-1-one; (E)-1-(4-bromophenyl)-2-(4-fluorophenylmethylsulfenyl)-3-(4-(N,N-dimethylamino)phenyl)prop-2-en-1-one; (E)-1-(4-bromophenyl)-2-(4-fluorophenylmethylsulfenyl)-3-(4-bromophenyl)prop-2-en-1-one; (E)-1-(4-bromophenyl)-2-(4-fluorophenylmethylsulfenyl)-3-(4-fluoro-2-trifluoromethylphenyl)prop-2-en-1-one; (E)-1-(4-bromophenyl)-2-(4-fluorophenylmethylsulfenyl)-3-(4-methoxyphenyl)prop-2-en-1-one; (E)-1-(4-chlorophenyl)-2-(2,4-dichlorophenylmethylsulfenyl)-3-(2,4,6-trimethoxyphenyl)prop-2-en-1-one; (E)-1-(4-chlorophenyl)-2-(2-chlorophenylmethylsulfenyl)-3-(4-hydroxy-3-nitrophenyl)prop-2-en-1-one; (E)-1-(4-chlorophenyl)-2-(3,4-dichlorophenylmethylsulfenyl)-3-(2,4,6-trimethoxyphenyl)prop-2-en-1-one; (E)-1-(4-chlorophenyl)-2-(3,4-dichlorophenylmethylsulfenyl)-3-(2,5-dimethoxyphenyl)prop-2-en-1-one; (E)-1-(4-chlorophenyl)-2-(3,4-dichlorophenylmethylsulfenyl)-3-(2-benzyloxyphenyl)prop-2-en-1-one; (E)-1-(4-chlorophenyl)-2-(3,4-dichlorophenylmethylsulfenyl)-3-(2-methoxyphenyl)prop-2-en-1-one; (E)-1-(4-chlorophenyl)-2-(3,4-dichlorophenylmethylsulfenyl)-3-(4-ethoxy-3-methoxyphenyl)prop-2-en-1-one; (E)-1-(4-chlorophenyl)-2-(4-bromophenylmethylsulfenyl)-3-(3,5-dimethylphenyl)prop-2-en-1-one; (E)-1-(4-chlorophenyl)-2-(4-chlorophenylmethylsulfenyl)-3-(2,5-dimethylphenyl)prop-2-en-1-one; (E)-1-(4-chlorophenyl)-2-(4- chlorophenylmethylsulfenyl)-3-(3,5-dimethylphenyl)prop-2-en-1-one; (E)-1-(4-chlorophenyl)-2-(4-chlorophenylmethylsulfenyl)-3-(4-hydroxy-3-nitrophenyl)prop-2-en-1-one; (E)-1-(4-chlorophenyl)-2-(4-chlorophenylmethylsulfenyl)-3-(4-methanesulfenylphenyl)prop-2-en-1-one; (E)-1-(4-chlorophenyl)-2-(4-fluorophenylmethylsulfenyl)-3-(2,4,6-trimethoxyphenyl)prop-2-en-1-one; (E)-1-(4-chlorophenyl)-2-(4-methylphenylmethylsulfenyl)-3-(2,5-dimethylphenyl)prop-2-en-1-one; (E)-1-(4-chlorophenyl)-2-(4-methylphenylmethylsulfenyl)-3-(2-methoxyphenyl)prop-2-en-1-one; (E)-1-(4-chlorophenyl)-2-(4-methylphenylmethylsulfenyl)-3-(3,5-dichlorophenyl)prop-2-en-1-one; (E)-1-(4-chlorophenyl)-2-(4-methylphenylmethylsulfenyl)-3-(4-(N,N-dimethylamino)phenyl)prop-2-en-1-one; (E)-1-(4-cyanophenyl)-2-(4-bromophenylmethylsulfenyl)-3-(4-hydroxy-3-nitrophenyl)prop-2-en-1-one; (E)-1-(4-methoxyphenyl)-2-(4-bromophenylmethylsulfenyl)-3-(4-hydroxy-3-nitrophenyl)prop-2-en-1-one; (E)-1-(4-nitrophenyl)-2-(4-bromophenylmethylsulfenyl)-3-(4-hydroxy-3-nitrophenyl)prop-2-en-1-one; (E)-1-(5-chloro-2-hydroxy-phenyl)-2-(4-bromophenylmethylsulfenyl)-3-(3-hydroxy-4-nitrophenyl)prop-2-en-1-one; (E)-1-(2-chlorophenyl)-2-(4-chlorophenylmethylsulfenyl)-3-(4-chlorophenyl)prop-2-en-1-one; (E)-1-(4-bromophenyl)-2-(4-bromophenylmethylsulfenyl)-3-(3-carboxy-4-hydroxyphenyl)prop-2-en-1-one; (E)-1-(4-bromophenyl)-2-(4-fluorophenylmethylsulfenyl)-3-(2,5-dimethylphenyl)prop-2-en-1-one; (E)-1-(4-bromophenyl)-2-(4-fluorophenylmethylsulfenyl)-3-(4-ethoxy-3-methoxyphenyl)prop-2-en-1-one; (E)-1-(4-carboxyphenyl)-2-(4-fluorophenylmethylsulfenyl)-3-(4-(N,N-dimethylamino)phenyl)prop-2-en-1-one; (E)-1-(4-chlorophenyl)-2-(2-chlorophenylmethylsulfenyl)-3-(4-ethoxy-3-methoxyphenyl)prop-2-en-1-one; (E)-1-(4-chlorophenyl)-2-(4-methylphenylmethylsulfenyl)-3-(4-fluoro-3-methylphenyl)prop-2-en-1-one; (E)-1-(4-chlorophenyl)-2-(4-methylphenylmethylsulfenyl)-3-(4-methanesulfenylphenyl)prop-2-en-1-one; (E)-1-(5-chloro-2-hydroxy-phenyl)-2-(4-bromophenylmethylsulfenyl)-3-(4-hydroxy-3-nitrophenyl)prop-2-en-1-one; (E)-1-(4-carboxyphenyl)-2-(2,4-dichlorophenylmethylsulfenyl)-3-(4-bromo-3-nitrophenyl)prop-2-en-1-one; (E)-1-(4-carboxyphenyl)-2-(2,4-dichlorophenylmethylsulfenyl)-3-(4-chloro-3-nitrophenyl)prop-2-en-1-one; (E)-1-(4-carboxyphenyl)-2-(2,4-dichlorophenylmethylsulfenyl)-3-(4-fluoro-3-nitrophenyl)prop-2-en-1-one; (E)-1-(4-carboxyphenyl)-2-(2-chlorophenylmethylsulfenyl)-3-(4-bromo-3-nitrophenyl)prop-2-en-1-one; (E)-1-(4-carboxyphenyl)-2-(2-chlorophenylmethylsulfenyl)-3-(4-fluoro-3-nitrophenyl)prop-2-en-1-one; (E)-1-(4-carboxyphenyl)-2-(2-fluorophenylmethylsulfenyl)-3-(4-chloro-3-nitrophenyl)prop-2-en-1-one; (E)-1-(4-nitrophenyl)-2-(4-bromophenylmethylsulfenyl)-3-(2,4,5-trimethoxyphenyl)prop-2-en-1-one; (E)-1-(4-carboxyphenyl)-2-(4-bromophenylmethylsulfenyl)-3-(2-fluorophenyl)prop-2-en-1-one; (E)-1-(4-bromophenyl)-2-(4-bromophenylmethylsulfenyl)-3-(3-(3-(2,5-dimethyl-3,6-dioxocyclohexa-1,4-dienyl)-3-methylbutanoyloxy)-4-nitrophenyl)prop-2-en-1-one; (E)-1-(4-carboxyphenyl)-2-(4-bromophenylmethylsulfenyl)-3-(4-(4-methylpiperazin-1-yl)-3-nitrophenyl)prop-2-en-1-one; (E)-1-(2,3,4,5,6-pentafluorophenyl)-2-(4-bromophenylmethylsulfenyl)-3-(4-fluoro-3-nitrophenyl)prop-2-en-1-one; (E)-1-(4-(2-(4-methylpiperazin-1-yl)ethylcarbamoyl)phenyl)-2-(4-bromophenylmethylsulfenyl)-3-(4-fluoro-3-nitrophenyl)prop-2-en-1-one; (E)-1-(4-(2-(morpholin-4-yl)ethylcarbamoyl)phenyl)-2-(4-bromophenylmethylsulfenyl)-3-(4-fluoro-3-nitrophenyl)prop-2-en-1-one; (E)-1-(4-(2-(N,N-diethylamino)ethylcarbamoyl)phenyl)-2-(4-bromophenylmethylsulfenyl)-3-(4-fluoro-3-nitrophenyl)prop-2-en-1-one; (E)-1-(4-(3-(4-methylpiperazin-1-yl)propylcarbamoyl)phenyl)-2-(4-bromophenylmethylsulfenyl)-3-(4-fluoro-3-nitrophenyl)prop-2-en-1-one; (E)-1-(4-(4-(5-(trifluoromethyl)pyridin-2-yl)piperazine-1-carbonyl)phenyl)-2-(4-bromophenylmethylsulfenyl)-3-(4-fluoro-3-nitrophenyl)prop-2-en-1-one; (E)-1-(4-[4-(2-hydroxyethyl)piperazine-1-carbonyl]phenyl)-2-(4-bromophenylmethylsulfenyl)-3-(4-fluoro-3-nitrophenyl)prop-2-en-1-one; (E)-1-(4-fluorophenyl)-2-(4-bromophenylmethylsulfenyl)-3-(4-fluoro-3-nitrophenyl)prop-2-en-1-one; (E)-1-(4-bromophenyl)-2-(4-bromophenylmethylsulfenyl)-3-(4-nitrophenyl)prop-2-en-1-one; (E)-1-(4-chlorophenyl)-2-(4-chlorophenylmethylsulfenyl)-3-(4-chlorophenyl)prop-2-en-1-one; (E)-1-(4-chlorophenyl)-2-(4-chlorophenylmethylsulfenyl)-3-(4-methoxyphenyl)prop-2-en-1-one; (E)-1-(4-chlorophenyl)-2-(4-chlorophenylmethylsulfenyl)-3-(4-nitrophenyl)prop-2-en-1-one; (E)-1-(4-chlorophenyl)-2-(4-chlorophenylmethylsulfenyl)-3-(4-trifluoromethylphenyl)prop-2-en-1-one; (E)-1-(4-carboxyphenyl)-2-(4-fluorophenylmethylsulfenyl)-3-(3-nitro-4-(4-(phenylmethyl)piperazin-1-yl)phenyl)prop-2-en-1-one; (E)-1-(4-fluorophenyl)-2-(4-fluorophenylmethylsulfenyl)-3-(4-(2-(4-methylpiperazin-1-yl)ethylamino)-3-nitrophenyl)prop-2-en-1-one; (E)-1-(4-fluorophenyl)-2-(4-fluorophenylmethylsulfenyl)-3-(4-(4-(2-hydroxyethyl)piperazin-1-yl)-3-nitrophenyl)prop-2-en-1-one; (E)-1-(4-fluoro-3-nitrophenyl)-2-(4-fluorophenylmethylsulfenyl)-3-(4-[4-(2-hydroxyethyl)piperazine-1-carbonyl]phenyl)prop-2-en-1-one; (E)-1-(4-carboxyphenyl)-2-(4-fluorophenylmethylsulfenyl)-3-(4-acetamido-3-nitrophenyl)prop-2-en-1-one; (E)-1-(4-carboxyphenyl)-2-(4-fluorophenylmethylsulfenyl)-3-(4-amino-3-nitrophenyl)prop-2-en-1-one; (E)-1-(4-((4-fluorophenyl)methylsulfenyl)-3-nitrophenyl)-2-(4-fluorophenylmethylsulfenyl)-3-(4-fluoro-3-nitrophenyl)prop-2-en-1-one; (E)-1-(4-((4-methylphenyl)sulfonyloxy)phenyl)-2-(4-fluorophenylmethylsulfenyl)-3-(4-fluoro-3-nitrophenyl)prop-2-en-1-one; (E)-1-(4-(2-(4-methylpiperazin-1-yl)ethylcarbamoyl)phenyl)-2-(4-fluorophenylmethylsulfenyl)-3-(4-fluoro-3-nitrophenyl)prop-2-en-1-one; (E)-1-(4-(2-(N,N-diethylamino)ethoxy)phenyl)-2-(4-fluorophenylmethylsulfenyl)-3-(4-fluoro-3-nitrophenyl)prop-2-en-1-one; (E)-1-(4-(3-(2,5-dimethyl-3,6-dioxocyclohexa-1,4-dienyl)-3-methylbutanoyloxy)phenyl)-2-(4-fluorophenylmethylsulfenyl)-3-(4-fluoro-3-nitrophenyl)prop-2-en-1-one; (E)-1-(4-(3-(morpholin-4-yl)propoxy)phenyl)-2-(4-fluorophenylmethylsulfenyl)-3-(4-fluoro-3-nitrophenyl)prop-2-en-1-one; (E)-1-(4-fluorophenyl)-2-(4-fluorophenylmethylsulfenyl)-3-(4-fluoro-3-nitrophenyl)prop-2-en-1-one; (E)-1-(4-hydroxyphenyl)-2-(4-fluorophenylmethylsulfenyl)-3-(4-fluoro-3-nitrophenyl)prop-2-en-1-one; (E)-1-(4-sulfamoylphenyl)-2-(4-fluorophenylmethylsulfenyl)-3-(4-fluoro-3-nitrophenyl)prop-2-en-1-one; (E)-1-(4-chlorophenyl)-2-(4-methoxyphenylmethylsulfenyl)-3-(4-fluorophenyl)prop-2-en-1-one; (E)-1-(4-chlorophenyl)-2-(4-methoxyphenylmethylsulfenyl)-3-(4-methoxyphenyl)prop-2-en-1-one; (E)-1-(4-carboxyphenyl)-2-(4-methylphenylmethylsulfenyl)-3-(4-fluoro-3-nitrophenyl)prop-2-en-1-one; (E)-1-(4-carboxyphenyl)-2-(4-methylphenylmethylsulfenyl)-3-(4-fluoro-3-nitrophenyl)

prop-2-en-1-one; (E)-1-(4-chloro-3-nitrophenyl)-2-(4-methylphenylmethylsulfenyl)-3-(4-fluoro-3-nitrophenyl)prop-2-en-1-one; (E)-1-(4-carboxyphenyl)-2-(4-trifluoromethylphenylmethylsulfenyl)-3-(4-chloro-3-nitrophenyl)prop-2-en-1-one; and (E)-1-(4-carboxyphenyl)-2-(4-trifluoromethylphenylmethylsulfenyl)-3-(4-fluoro-3-nitrophenyl)prop-2-en-1-one; or salts thereof.

20. A compound according to claim 16, which is (E)-methyl-4-(2-(4-bromobenzylthio)-3-(4-fluoro-3-nitrophenyl)acryloyl)benzoate, or a salt thereof.

21. A compound according to claim 15, or a salt thereof, wherein n is 1.

22. A compound according to claim 21, or a salt thereof, wherein Ar$^1$ is substituted phenyl.

23. A compound according to claim 22, wherein Ar$^3$ is phenyl substituted at the 4-position with —C(=O)OH, or a salt of such a compound.

24. A compound according to claim 21 selected from the group consisting of (E)-1-(4-chlorophenyl)-2-(2-chlorophenylmethylsulfinyl)-3-(2,4,6-trimethoxyphenyl)prop-2-en-1-one and (E)-1-(4-chlorophenyl)-2-(4-chlorophenylmethylsulfinyl)-3-(4-fluoro-2-trifluoromethylphenyl)prop-2-en-1-one.

25. A compound according to claim 15, or a salt thereof, wherein n is 2.

26. A compound according to claim 25, or a salt thereof, wherein Ar$^1$ is substituted phenyl.

27. A compound according to claim 26, wherein Ar$^3$ is phenyl substituted at the 4-position with —C(=O)OH, or a salt of such a compound.

28. A compound according to claim 25 selected from the group consisting of (E)-1-(4-bromophenyl)-2-(4-fluorophenylmethylsulfonyl)-3-(2,5-dimethylphenyl)prop-2-en-1-one; (E)-1-(4-chlorophenyl)-2-(2-chlorophenylmethylsulfonyl)-3-(2-benzyloxyphenyl)prop-2-en-1-one; (E)-1-(4-chlorophenyl)-2-(3,4-dichlorophenylmethylsulfonyl)-3-(2-methoxyphenyl)prop-2-en-1-one; (E)-1-(4-chlorophenyl)-2-(4-chlorophenylmethylsulfonyl)-3-(3,5-dimethylphenyl)prop-2-en-1-one; (E)-1-(4-chlorophenyl)-2-(4-chlorophenylmethylsulfonyl)-3-(4-benzyloxyphenyl)prop-2-en-1-one; (E)-1-(4-chlorophenyl)-2-(4-methylphenylmethylsulfonyl)-3-(2,3-dichlorophenyl)prop-2-en-1-one; (E)-1-(4-chlorophenyl)-2-(4-methylphenylmethylsulfonyl)-3-(2,5-dimethylphenyl)prop-2-en-1-one; (E)-1-(4-chlorophenyl)-2-(4-methylphenylmethylsulfonyl)-3-(2-benzyloxyphenyl)prop-2-en-1-one; (E)-1-(4-methoxyphenyl)-2-(4-bromophenylmethylsulfonyl)-3-(4-bromophenyl)prop-2-en-1-one; (E)-1-(4-bromophenyl)-2-(4-bromophenylmethylsulfonyl)-3-(4-hydroxy-3-nitrophenyl)prop-2-en-1-one; (E)-1-(4-bromophenyl)-2-(4-chlorophenylmethylsulfonyl)-3-(2-benzyloxyphenyl)prop-2-en-1-one; (E)-1-(4-bromophenyl)-2-(4-methylphenylmethylsulfonyl)-3-(4-methanesulfonylphenyl)prop-2-en-1-one; (E)-1-(4-chlorophenyl)-2-(4-chlorophenylmethylsulfonyl)-3-(2,3,4-trimethoxyphenyl)prop-2-en-1-one; (E)-1-(4-bromophenyl)-2-(4-chlorophenylmethylsulfonyl)-3-(2-hydroxy-4-methoxyphenyl)prop-2-en-1-one; (E)-1-(4-bromophenyl)-2-(4-fluorophenylmethylsulfonyl)-3-(3,5-dimethylphenyl)prop-2-en-1-one; (E)-1-(4-bromophenyl)-2-(4-methylphenylmethylsulfonyl)-3-(4-methanesulfenylphenyl)prop-2-en-1-one; (E)-1-(4-chlorophenyl)-2-(2-chlorophenylmethylsulfonyl)-3-(4-ethoxy-3-methoxyphenyl)prop-2-en-1-one; (E)-1-(4-chlorophenyl)-2-(3,4-dichlorophenylmethylsulfonyl)-3-(4-hydroxyphenyl)prop-2-en-1-one; (E)-1-(4-chlorophenyl)-2-(4-chlorophenylmethylsulfonyl)-3-(2,5-dimethylphenyl)prop-2-en-1-one; (E)-1-(4-chlorophenyl)-2-(4-chlorophenylmethylsulfonyl)-3-(3-ethoxy-4-hydroxyphenyl)prop-2-en-1-one; (E)-1-(4-chlorophenyl)-2-(4-chlorophenylmethylsulfonyl)-3-(4-bromophenyl)prop-2-en-1-one; (E)-1-(4-chlorophenyl)-2-(4-chlorophenylmethylsulfonyl)-3-(4-methanesulfenylphenyl)prop-2-en-1-one; (E)-1-(4-chlorophenyl)-2-(4-fluorophenylmethylsulfonyl)-3-(2,4,6-trimethoxyphenyl)prop-2-en-1-one; (E)-1-(4-chlorophenyl)-2-(4-methylphenylmethylsulfonyl)-3-(2-methoxyphenyl)prop-2-en-1-one; (E)-1-(4-chlorophenyl)-2-(4-methylphenylmethylsulfonyl)-3-(3,5-dimethylphenyl)prop-2-en-1-one; (E)-1-(4-chlorophenyl)-2-(4-methylphenylmethylsulfonyl)-3-(4-ethoxy-3-methoxyphenyl)prop-2-en-1-one; (E)-1-(4-nitrophenyl)-2-(4-chlorophenylmethylsulfonyl)-3-(2,4,6-trimethoxyphenyl)prop-2-en-1-one; (E)-1-(4-nitrophenyl)-2-(4-chlorophenylmethylsulfonyl)-3-(2-methoxyphenyl)prop-2-en-1-one; (E)-1-(4-bromophenyl)-2-(4-chlorophenylmethylsulfonyl)-3-(4-methoxyphenyl)prop-2-en-1-one; (E)-1-(4-bromophenyl)-2-(4-fluorophenylmethylsulfonyl)-3-(4-bromophenyl)prop-2-en-1-one; (E)-1-(4-chlorophenyl)-2-(4-methylphenylmethylsulfonyl)-3-(4-bromophenyl)prop-2-en-1-one; (E)-1-(4-chlorophenyl)-2-(4-methylphenylmethylsulfonyl)-3-(4-methanesulfenylphenyl)prop-2-en-1-one; (E)-1-(4-bromophenyl)-2-(4-bromophenylmethylsulfonyl)-3-(3,5-dibromo-4-hydroxyphenyl)prop-2-en-1-one; (E)-1-(4-bromophenyl)-2-(4-bromophenylmethylsulfonyl)-3-(3,5-dichloro-4-hydroxyphenyl)prop-2-en-1-one; (E)-1-(4-bromophenyl)-2-(4-chlorophenylmethylsulfonyl)-3-(2,4,6-trimethoxyphenyl)prop-2-en-1-one; (E)-1-(4-carboxyphenyl)-2-(4-bromophenylmethylsulfonyl)-3-(4-chloro-3-nitrophenyl)prop-2-en-1-one; (E)-1-(4-chlorophenyl)-2-(2-chlorophenylmethylsulfonyl)-3-(4-bromophenyl)prop-2-en-1-one; (E)-1-(4-chlorophenyl)-2-(4-chlorophenylmethylsulfonyl)-3-(2-methoxyphenyl)prop-2-en-1-one; (E)-1-(4-chlorophenyl)-2-(4-chlorophenylmethylsulfonyl)-3-(4-hydroxy-3-nitrophenyl)prop-2-en-1-one; (E)-1-(4-chlorophenyl)-2-(4-chlorophenylmethylsulfonyl)-3-(biphenyl-4-yl)prop-2-en-1-one; (E)-1-(4-chlorophenyl)-2-(4-methylphenylmethylsulfonyl)-3-(4-chlorophenyl)prop-2-en-1-one; and (E)-1-(4-iodophenyl)-2-(4-iodophenylmethylsulfonyl)-3-(4-bromophenyl)prop-2-en-1-one; or salts thereof.

29. A process for preparing compound according to claim 1, comprising condensing a compound of formula II,

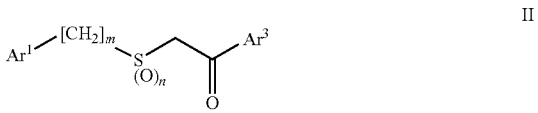

or a salt thereof, with an aromatic aldehyde of formula III:

or a salt thereof,
wherein $Ar^1$, $Ar^2$, $Ar^3$, m and n are as defined in claim 1, and
isolating from the reaction mixture the compound according to claim 1, or a salt thereof.

30. An antibody conjugate of the formula:

I-L-Ab, or a salt thereof, wherein
I is a compound according to formula I as defined in claim 1,
Ab is an antibody; and
-L- is a single bond or a linking group covalently linking said compound of formula I to said antibody.

31. The antibody conjugate of claim 30, or a salt thereof, wherein the antibody is a monoclonal antibody or a monospecific polyclonal antibody.

32. The antibody conjugate of claim 31, or a salt thereof, wherein the antibody is a tumor-specific antibody.

33. A pharmaceutical composition comprising a pharmaceutically acceptable carrier and a compound according to claim 1, or a pharmaceutically acceptable salt thereof.

34. A pharmaceutical composition comprising a pharmaceutically acceptable carrier and an antibody conjugate according to claim 30, or a pharmaceutically acceptable salt thereof.

35. A method of treating an individual suffering from a cellular proliferative disorder selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellularisorder post transplantation lymphocellular proliferative disorder, macular degeneration, retinopathies, proliferative vitreoretinopathy, non-cancerous lymphocellular proliferative disorders, ovarian cancer, cervical cancer, breast cancer, prostate cancer, testicular cancer, lung cancer, renal cancer, colorectal cancer, skin cancer, brain cancer and leukemia, comprising administering to the individual an effective amount of at least one compound according to claim 1, or a pharmaceutically acceptable salt thereof.

36. A method according to claim 35, wherein the cancer is selected from the group consisting of acute myeloid leukemia, chronic myeloid leukemia, acute lymphoid leukemia, and chronic lymphoid leukemia.

37. A method of inducing apoptosis of cancer cells in an individual afflicted with cancer wherein the cancer cells are tumor cells selected from the group consisting of ovarian, cervical, breast, prostate, testicular, lung, renal, colorectal, skin and brain tumor cells, comprising administering to the individual an effective amount of at least one compound according to claim 1, or a pharmaceutically acceptable salt thereof.

38. A method of treating an individual suffering from a cellular proliferative disorder selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy, non-cancerous lymphocellular proliferative disorders, ovarian cancer, cervical cancer, breast cancer, prostate cancer, testicular cancer, lung cancer, renal cancer, colorectal cancer, skin cancer, brain cancer and leukemia, comprising administering to the individual an effective amount of at least one antibody conjugate according to claim 30, or a pharmaceutically acceptable salt thereof.

39. A method of inducing apoptosis of cancer cells in an individual afflicted with cancer wherein the cancer cells are tumor cells selected from the group consisting of ovarian, cervical, breast, prostate, testicular, lung, renal, colorectal, skin and brain tumor cells, comprising administering to the individual an effective amount of at least one antibody conjugate according to claim 30, or a pharmaceutically acceptable salt thereof.

40. The compound (E)-1-(4-carboxyphenyl)-2-(phenylmethylsulfenyl)-3-(4-fluoro-3-nitrophenyl)prop-2-en-1-one, or salt thereof.

\* \* \* \* \*